(12) United States Patent
Ferrari et al.

(10) Patent No.: US 9,526,824 B2
(45) Date of Patent: Dec. 27, 2016

(54) NANOCHANNELED DEVICE AND RELATED METHODS

(71) Applicants: The Board of Regents of the University of Texas System, Austin, TX (US); The Ohio State University Research Foundation, Columbus, OH (US)

(72) Inventors: Mauro Ferrari, Houston, TX (US); Xuewu Liu, Sugar Land, TX (US); Alessandro Grattoni, Houston, TX (US); Daniel Fine, Austin, TX (US); Randy Goodall, Austin, TX (US); Sharath Hosali, Austin, TX (US); Ryan Medema, Pflugerville, TX (US); Lee Hudson, Elgin, TX (US)

(73) Assignees: The Board of Regents of the University of Texas System, Austin, TX (US); The Ohio State University Research Foundation, Columbus, OH (US)

( * ) Notice: Subject to any disclaimer, the term of this patent is extended or adjusted under 35 U.S.C. 154(b) by 784 days.

(21) Appl. No.: 13/875,871

(22) Filed: May 2, 2013

(65) Prior Publication Data
US 2013/0240483 A1 Sep. 19, 2013

Related U.S. Application Data

(63) Continuation of application No. 12/618,233, filed on Nov. 13, 2009, now Pat. No. 8,480,637.
(Continued)

(51) Int. Cl.
*C23F 1/00* (2006.01)
*A61M 5/00* (2006.01)
(Continued)

(52) U.S. Cl.
CPC .............. *A61M 5/00* (2013.01); *A61K 9/0097* (2013.01); *A61M 37/00* (2013.01);
(Continued)

(58) Field of Classification Search
CPC .............. B81C 1/00444; B81C 1/00476; B81C 1/00119; B01D 67/0034; Y10S 148/05
(Continued)

(56) References Cited

U.S. PATENT DOCUMENTS

| 3,731,681 A | 5/1973 | Blackshear et al. |
| 3,921,636 A | 11/1975 | Zaffaroni |

(Continued)

FOREIGN PATENT DOCUMENTS

| CN | 1585627 | 2/2005 |
| DE | 10 2006 014476 | 7/2007 |

(Continued)

OTHER PUBLICATIONS

"The Economic Costs of Drug Abuse in the United States," www.whitehousedrugpolicy.gov, Sep. 2001.
(Continued)

*Primary Examiner* — Binh X Tran
(74) *Attorney, Agent, or Firm* — Parker Highlander PLLC

(57) ABSTRACT

A nanochannel delivery device and method of manufacturing and use. The nanochannel delivery device comprises an inlet, an outlet, and a nanochannel. The nanochannel may be oriented parallel to the primary plane of the nanochannel delivery device. The inlet and outlet may be in direct fluid communication with the nanochannel.

22 Claims, 35 Drawing Sheets

Related U.S. Application Data

(60) Provisional application No. 61/168,844, filed on Apr. 13, 2009, provisional application No. 61/114,687, filed on Nov. 14, 2008.

(51) Int. Cl.
| | | |
|---|---|---|
| *A61K 9/00* | (2006.01) | |
| *A61M 37/00* | (2006.01) | |
| *B81C 1/00* | (2006.01) | |
| *B82Y 5/00* | (2011.01) | |
| *A61M 5/142* | (2006.01) | |

(52) U.S. Cl.
CPC ............ *B81C 1/00119* (2013.01); *B82Y 5/00* (2013.01); *A61M 5/14276* (2013.01); *B81B 2201/058* (2013.01); *B81B 2203/0338* (2013.01); *Y10T 137/8593* (2015.04); *Y10T 156/1064* (2015.01)

(58) Field of Classification Search
USPC .......................................... 216/2, 39, 41, 56
See application file for complete search history.

(56) References Cited

U.S. PATENT DOCUMENTS

| | | | |
|---|---|---|---|
| 4,834,704 | A | 5/1989 | Reinicke |
| 4,955,861 | A | 9/1990 | Enegren et al. |
| 5,085,656 | A | 2/1992 | Polaschegg |
| 5,395,324 | A | 3/1995 | Hinrichs et al. |
| 5,651,900 | A | 7/1997 | Keller et al. |
| 5,728,396 | A | 3/1998 | Peery et al. |
| 5,769,823 | A | 6/1998 | Otto |
| 5,770,076 | A | 6/1998 | Chu et al. |
| 5,798,042 | A | 8/1998 | Chu et al. |
| 5,893,974 | A | 4/1999 | Keller et al. |
| 5,938,923 | A | 8/1999 | Tu et al. |
| 5,948,164 | A | 9/1999 | Iida et al. |
| 5,948,255 | A | 9/1999 | Keller et al. |
| 5,985,164 | A | 11/1999 | Chu et al. |
| 5,985,328 | A | 11/1999 | Chu et al. |
| 6,044,981 | A | 4/2000 | Chu et al. |
| 6,592,519 | B1 | 7/2003 | Martinez |
| 7,025,871 | B2 | 4/2006 | Broadley et al. |
| 7,135,144 | B2 | 11/2006 | Christel et al. |
| 7,326,561 | B2 | 2/2008 | Goodman et al. |
| 7,413,846 | B2 | 8/2008 | Maloney et al. |
| 7,955,614 | B2 | 6/2011 | Martin et al. |
| 8,480,637 | B2 | 7/2013 | Ferrari et al. |
| 8,632,510 | B2 | 1/2014 | Ferrari et al. |
| 9,005,185 | B2 | 4/2015 | Ferrari et al. |
| 2002/0087120 | A1 | 7/2002 | Rogers et al. |
| 2002/0156462 | A1 | 10/2002 | Stultz |
| 2003/0010638 | A1 | 1/2003 | Hansford et al. |
| 2003/0064095 | A1 | 4/2003 | Martin et al. |
| 2004/0038260 | A1 | 2/2004 | Martin et al. |
| 2004/0082908 | A1 | 4/2004 | Whitehurst et al. |
| 2004/0116905 | A1 | 6/2004 | Pedersen et al. |
| 2004/0260418 | A1 | 12/2004 | Staats |
| 2004/0262159 | A1 | 12/2004 | Martin et al. |
| 2005/0118229 | A1 | 6/2005 | Boiarski |
| 2006/0180469 | A1 | 8/2006 | Han et al. |
| 2006/0191831 | A1 | 8/2006 | Hansford et al. |
| 2006/0259015 | A1 | 11/2006 | Steinbach |
| 2006/0270983 | A1 | 11/2006 | Lord et al. |
| 2007/0066138 | A1 | 3/2007 | Ferrari et al. |
| 2007/0077273 | A1 | 4/2007 | Martin et al. |
| 2007/0286773 | A1 | 12/2007 | Schlautmann et al. |
| 2008/0073506 | A1 | 3/2008 | Lazar |
| 2009/0181200 | A1* | 7/2009 | Borenstein .......... B81C 1/00119 428/36.9 |
| 2009/0214392 | A1 | 8/2009 | Kameoka et al. |
| 2010/0003143 | A1* | 1/2010 | Toonder .............. B01F 13/0059 417/53 |
| 2010/0077515 | A1* | 3/2010 | Espinosa ............. B81C 1/00071 850/40 |
| 2010/0170796 | A1* | 7/2010 | Bhatia ................... B01L 3/5027 204/453 |
| 2010/0212762 | A1* | 8/2010 | Den Toonder ...... B01F 13/0059 137/803 |
| 2011/0137596 | A1 | 6/2011 | Grattoni et al. |

FOREIGN PATENT DOCUMENTS

| | | |
|---|---|---|
| EP | 1 977 775 | 10/2008 |
| WO | WO 00/74751 | 12/2000 |
| WO | WO 2004/036623 | 4/2004 |
| WO | WO 2005/079387 | 9/2005 |
| WO | WO 2006/113860 | 10/2006 |
| WO | WO 2007/047539 | 4/2007 |
| WO | WO 2007/089483 | 8/2007 |
| WO | WO 2008/019886 | 9/2008 |
| WO | WO 2009/149362 | 12/2009 |
| WO | WO 2010/056986 | 5/2010 |
| WO | WO 2010/120817 | 10/2010 |

OTHER PUBLICATIONS

"Under the Counter: The Diversion and Abuse of Controlled Prescription Drugs in the US," *The National Center on Addiction and Substance Abuse (CASA) at Columbia University*, New York, NY, CASA, Jul. 2005.

Extended European Search Report issued in European Application No. 09826831, mailed Jul. 12, 2012.

Nath et al., "Buprenorphine pharmacokinetics: relative bioavailability of sublingual tablet and liquid formulations," *J. Clin. Pharmacol.*, 39:619-623, 1999.

Report Stakeholder Workshop on a National Buprenorphine Program Health Canada Nov. 18, 2004.

Samhsa, "Overview of Findings from the 2002 National Survey on Drug Use and Health," Rockville, MD, DHHS publication, SMA 03-3774.

Samhsa, "Results from the 2003 National Survey on Drug Use and Health: National Findings," Rockeville, MD, DHHS publication, SMA 3-3964.

Samhsa, "The DAWN Report: oxycodaone, hydrocodone, and polydrug use," 2002. Jul. 2004 http://oas.samhsa.gov/2k4/oxycodone/oxycodone.cfm.

Office Action issued in Chinese Application No. 200980154070.X, dated Jan. 7, 2013. (English Translation).

Office Action issued in European Application No. 09826831, dated Jul. 11, 2013.

Office Action issued in U.S. Appl. No. 12/618,233, mailed Apr. 27, 2012.

Office Action issued in U.S. Appl. No. 12/618,233, mailed Oct. 16, 2012.

PCT International Preliminary Report on Patentability issued in International Application No. PCT/US2009/064376, mailed May 26, 2011.

PCT International Search Report and Written Opinion issued in International Application No. PCT/US2009/064376, mailed Aug. 23, 2010.

Christensen et al., "Tantalum oxide thin films as protective coatings for sensors," *J. Micromech. Microeng.*, 9:113-118, 1999.

Extended European Search Report issued in European Application No. 10765046, mailed Oct. 1, 2012.

Extended European Search Report issued in European Application No. 11784219.5, mailed Jul. 8, 2014.

Fine et al., "A robust nanofluidic membrane with tunable zero-order release for implantable dose specific drug delivery," *Lab on a Chip*, 10(2): 3074-3083, 2010.

Hammerle et al., "Biostability of micro-photodiode arrays for subretinal implantation," *Biomaterials*, 23:797-804, 2002.

Hess et al., "PECVD silicon carbide as a thin film packaging material for microfabricated neural electrodes," *Mater. Res. Soc. Symp. Proc.*, 1009-U04-03, 2007.

(56) References Cited

OTHER PUBLICATIONS

Narayan et al., "Mechanical and biological properties of nanoporous carbon membranes," *Biomed. Mater.,* 3:034107, 2008.
Nath et al., "Buprenorphine pharmacokinetics: relative bioavailability of sub lingual tablet and liquid formulations," *J. Clin. Pharmacol.,* 39:619-623, 1999.
Nurdin et al., "Haemocompatibility evaluation of DLC-and SIC-coated surfaces," *Eur Cells Mat.,* 5: 17-28, 2003.
Office Action issued in European Application No. 10765046, mailed Jul. 11, 2013.
Office Action issued in U.S. Appl. No. 13/111,368, mailed Apr. 21, 2015.
Office Action issued in U.S. Appl. No. 13/111,368, mailed Oct. 17, 2014.
Office Action issued in U.S. Appl. No. 13/264,069, mailed Feb. 22, 2013.
Office Action issued in U.S. Appl. No. 13/264,069, mailed Oct. 29, 2012.
PCT International Search Report and Written Opinion issued in International Application No. PCT/US2011/037094, dated Jan. 13, 2012.
PCT International Search Report and Written Opinion issued in International Application No. PCT/US2010/030937, dated Feb. 21, 2011.
Report: Stakeholder Workshop on a National Buprenorphine Program, Health Canada, Nov. 18, 2004.
Samhsa, "Results from the 2003 National Survey on Drug Use and Health: National Findings," Rockeville, MD, DHHS publication, SMA 04-3964.
Schmitt et al., "Passivation and corrosion of microelectrode arrays," *Electrochimica Acta,* 44:3865-3883, 1999.
Voskerician et al., "Biocompatibility and biofouling of MEMS drug delivery devices," *Biomaterials,* 24:1959-1967, 2003.
Yakimova et al., "Surface functionalization and biomedical applications base on SiC," *J Physics D*, 40: 6435-6442, 2007.
Zorman et al., "Silicon carbide as a material for biomedical Microsystems," *DIT*, Apr. 1-3, 2009.

\* cited by examiner

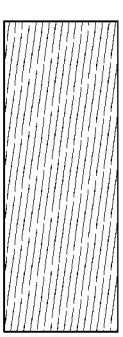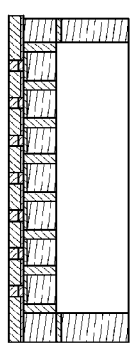
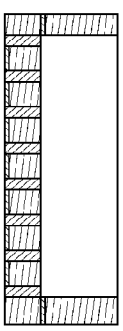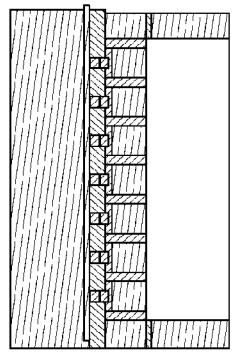
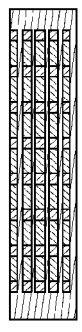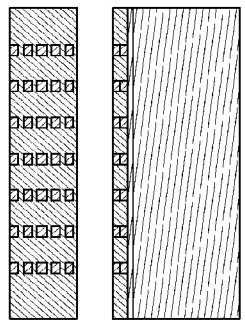
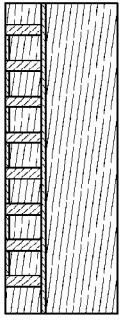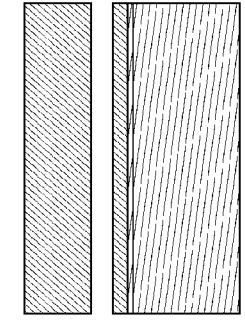
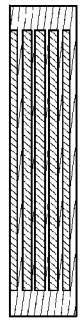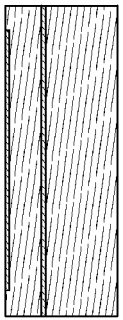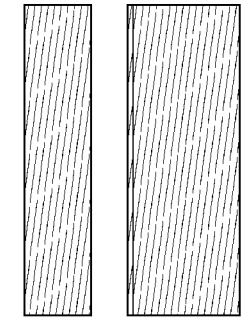
FIG. 1A  FIG. 1B  FIG. 1C  FIG. 1D  FIG. 1E
FIG. 1F  FIG. 1G  FIG. 1H  FIG. 1I  FIG. 1J

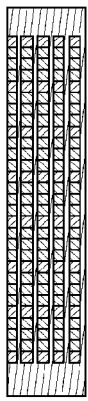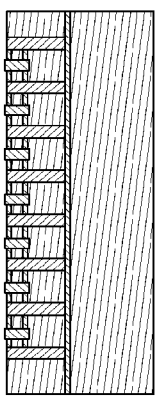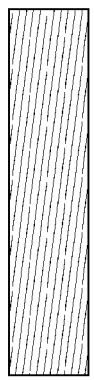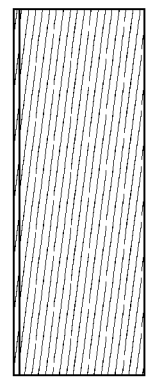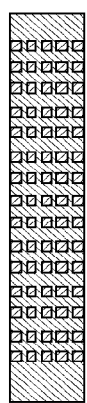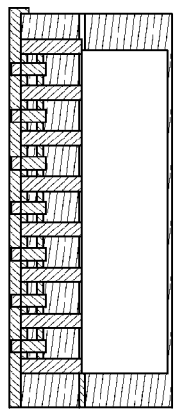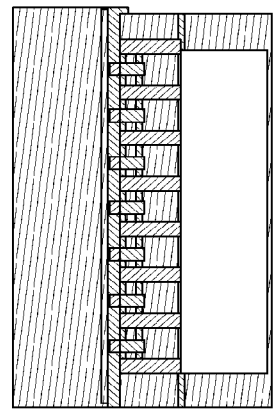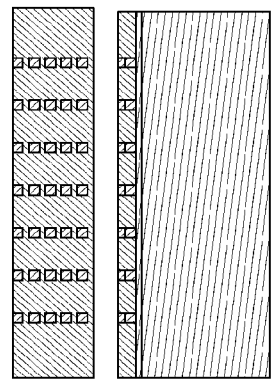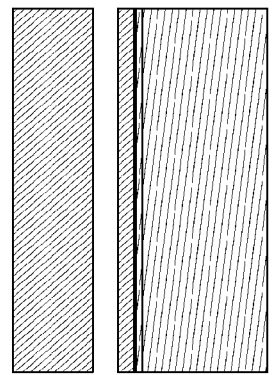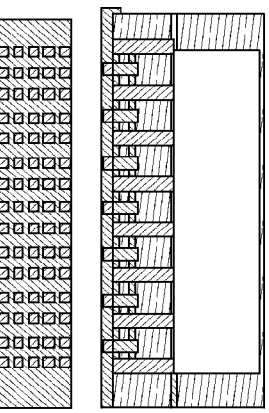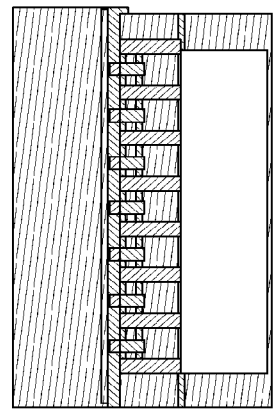

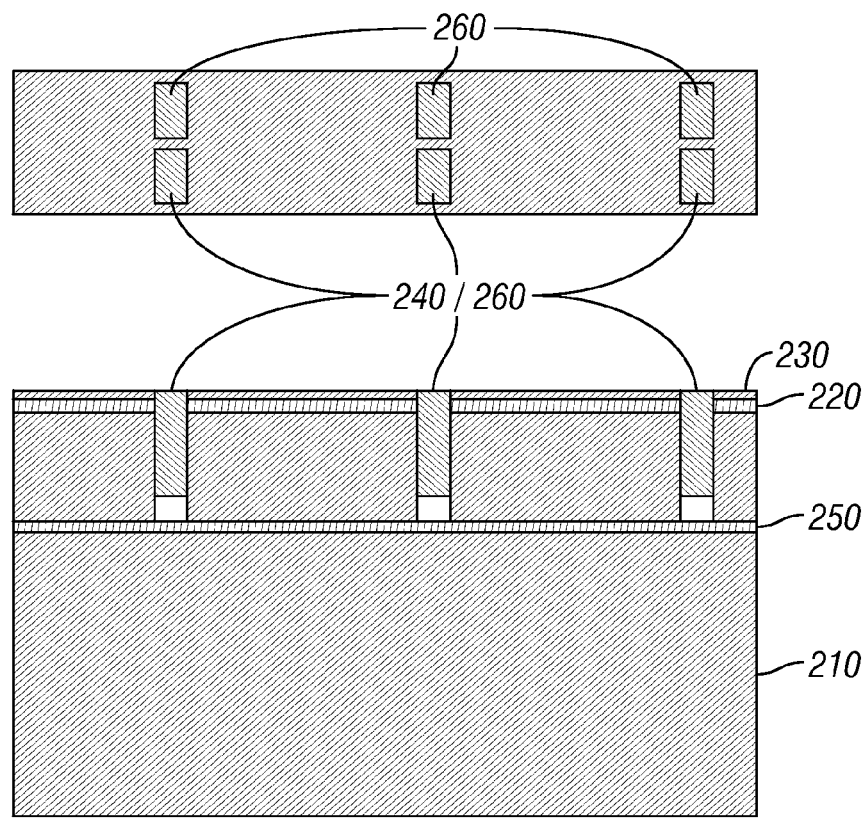
FIG. 5C
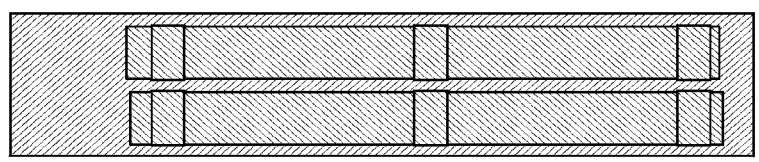
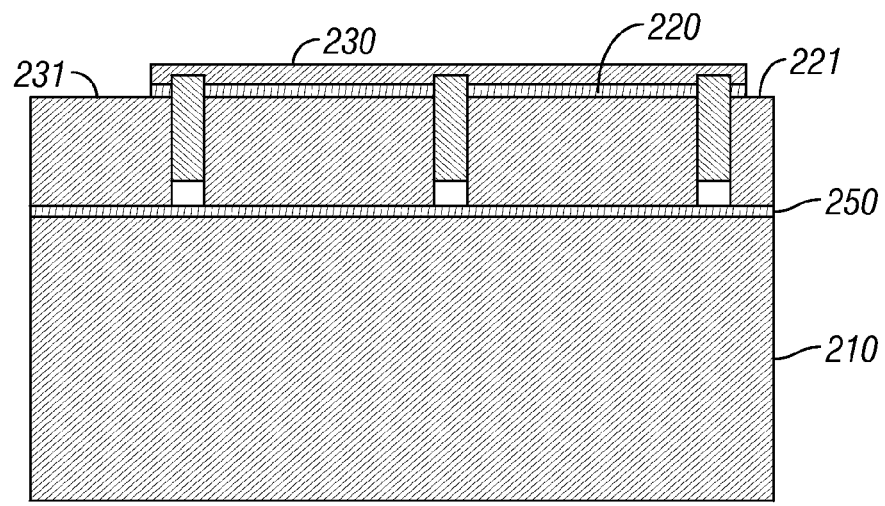
FIG. 5D

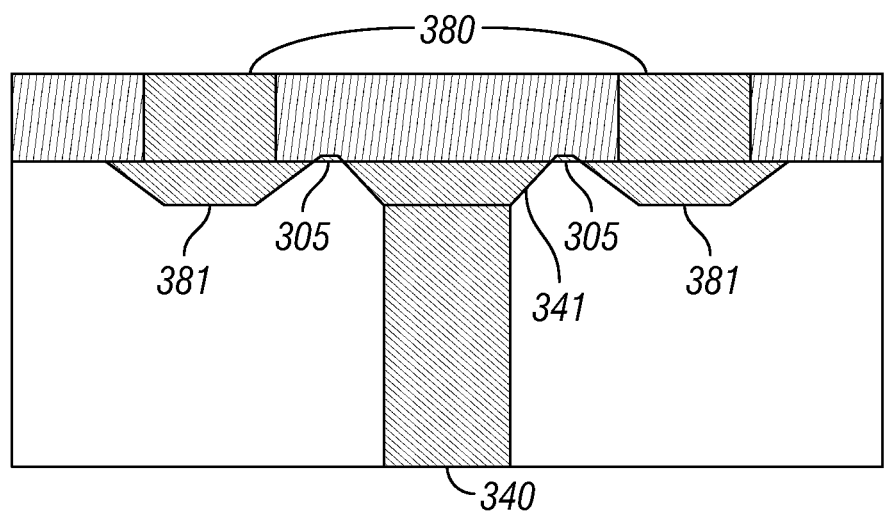
FIG. 7
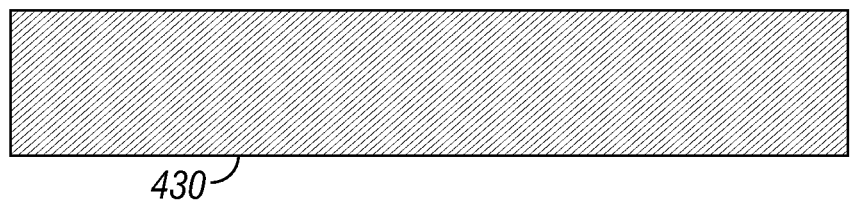
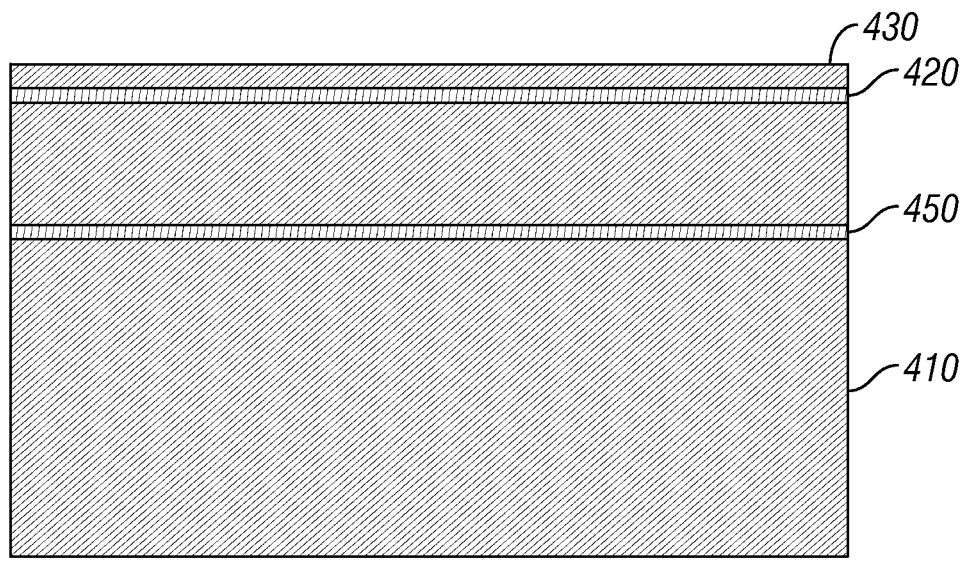
FIG. 8A

SEM image of deep etched 190umx190um openings.

Optical image of front surface of nDS device after anodic bonding.

*Optical image of inlet channel openings under bonded and lapped glass film.*

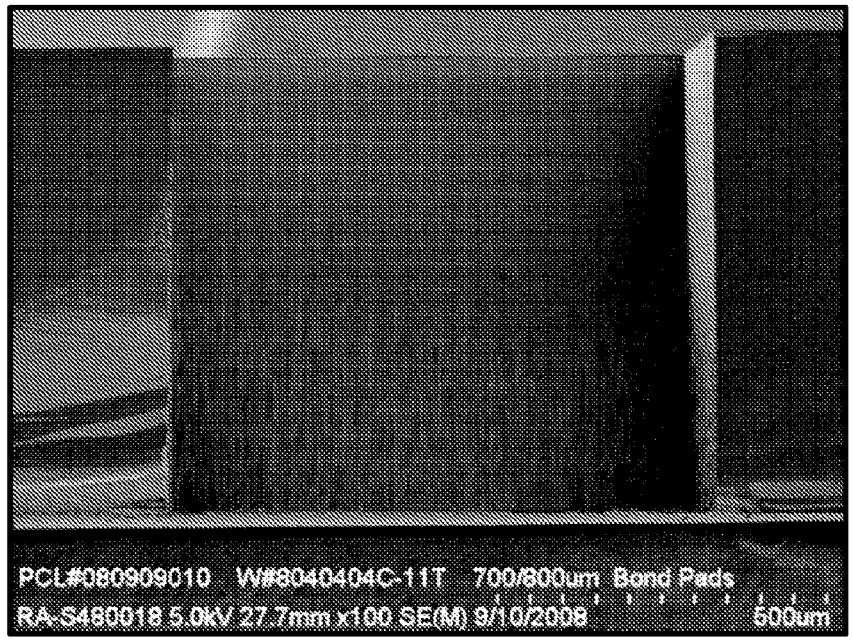

FIG. 17

| Nanochannel Placeholder | Ceiling & Floor (substrate & capping layer) | Removal Solvent/Etchant |
|---|---|---|
| Tungsten | $SiO_2$, $Si_3N_4$, Si, SiC, SiCN, Au, BCB | Warm $H_2O_2$ |
| Ge | $SiO_2$, $Si_3N_4$, Si, SiC, SiCN, Au, BCB | Warm $H_2O_2$ |
| Cu | $SiO_2$, $Si_3N_4$, Si, SiC, SiCN | Piranha |
| Au | $SiO_2$, $Si_3N_4$, Si, SiC, SiCN, BCB | Aqua Regia |
| Cr | $SiO_2$, $Si_3N_4$, Si, SiC, SiCN, BCB | Chrome Etchant |
| TiN | $SiO_2$, $Si_3N_4$, Si, SiC, SiCN, BCB | Ammonia/Peroxide mix |
| Al | $SiO_2$, $Si_3N_4$, Si, SiC, SiCN | $H_3PO_4/HNO_3$ |
| Al | $SiO_2$, $Si_3N_4$, SiC, SiCN, BCB | KOH |
| Phosphosilicate glass | $Si_3N_4$, W, SiC, SiCN, Si, Au, BCB | Dilute HF |
| $SiO_2$ | $Si_3N_4$, W, SiC, Si, SiCN, Au, BCB | BOE |
| Polymers | Si, $Si_3N_4$, SiC, SiCN, Oxide, Metal | Organic Solvents, Piranha |
| $Si_3N_4$ | Si, $SiO_2$, SiC, SiCN | Hot $H_3PO_4$ |
| Si | $Si_3N_4$, $SiO_2$, SiC, SiCN | Hot KOH |

FIG. 18

NANOCHANNELED DEVICE AND RELATED METHODS

CROSS-REFERENCE TO RELATED APPLICATIONS

This application is a Continuation of U.S. patent application Ser. No. 12/618,233, filed Nov. 13, 2009, now U.S. Pat. No. 8,480,637, entitled "Nanochanneled Device and Related Methods", U.S. Provisional Patent Application Ser. No. 61/114,687, filed Nov. 14, 2008, entitled "Nanochanneled Device and Method of Use", and U.S. Provisional Patent Application Ser. No. 61/168,844, filed Apr. 13, 2009, entitled "Nanochanneled Device and Method of Use", the entire disclosures of which are specifically incorporated herein by reference.

This invention was made with government support under contract NNJ06HE06A awarded by NASA. The government has certain rights in this invention.

BACKGROUND INFORMATION

Considerable advances have been made in the field of therapeutic agent (e.g. drug) delivery technology over the last three decades, resulting in many breakthroughs in clinical medicine. The creation of therapeutic agent delivery devices that are capable of delivering therapeutic agents in controlled ways is still a challenge. One of the major requirements for an implantable drug delivery device is controlled release of therapeutic agents, ranging from small drug molecules to larger biological molecules. It is particularly desirable to achieve a continuous passive drug release profile consistent with zero order kinetics whereby the concentration of drug in the bloodstream remains constant throughout an extended delivery period.

These devices have the potential to improve therapeutic efficacy, diminish potentially life-threatening side effects, improve patient compliance, minimize the intervention of healthcare personnel, reduce the duration of hospital stays, and decrease the diversion of regulated drugs to abusive uses.

Nanochannel delivery devices may be used in drug delivery products for the effective administration of drugs. In addition, nanochannel delivery devices can be used in other applications where controlled release of a substance over time is needed.

SUMMARY

Embodiments of this invention comprise a nanochannel delivery device having nanochannels within a structure configured to yield high mechanical strength and high flow rates. Various fabrication protocols may be used to form the nanochannel delivery device. Embodiments of the fabricated devices feature horizontal nanochannel lay-out (e.g., the nanochannel is parallel to the primary plane of the device), high molecule transport rate, high mechanical strength, optional multilayered lay-out, amenability to select channel lining materials, and possible transparent top cover. Based on silicon microfabrication technology, the dimensions of the nanochannel area as well as concomitant microchannel areas can be precisely controlled, thus providing a predictable, reliable, constant release rate of drug (or other) molecules over an extended time period. In certain embodiments, the nanochannel delivery device can be used to build a multilayered nanochannel structure. Multilayered nanochannel structures can extend the limit of release rate range of a single layer nanochannel delivery device or system, and allow a wide range of pre-defined porosity to achieve an arbitrary release rate using any preferred nanochannel size.

In certain embodiments, the nanochannel delivery device is made of a "sandwich" of materials, composed of a thin top layer, the horizontal nanochannels, and a thicker bottom wafer. The thin top layer can house an array of microchannels that offer an inlet or outlet for diffusing molecules. It can also serve as the lid or ceiling for the nanochannels by providing the channels' top surface. The thicker bottom wafer can house an array of microchannels that offer a collateral outlet or inlet. Note that in the following, inlets are indicated in the bottom wafer and outlets are indicated in the top layer, but this is not a limit of the invention. In certain embodiments, the nanochannels are fabricated by a sacrificial layer technique that provides smooth surfaces and precisely controlled dimensions. The nanochannels can be formed in between the two layers and connect the outlet microchannels with the array of inlet microchannels formed in the bottom wafer, additionally allowing thin surface layers to be applied to both the top and the bottom surfaces independently, in order to optimize channel properties such as surface charge, hydrophobicity, wetting and conductivity. Each inlet and outlet microchannel can be connected to one, two, or more nanochannels. The height, width, and length of the nanochannel can be used to maintain a constant (zero-order) delivery. By the help of nanofabrication, a nanochannel length of 10 nm or less is feasible.

In certain embodiments, the nanochannel delivery device is designed to yield high strength. This can be achieved by a supporting structure obtained in the bottom side of the thick wafer. The structure can be composed by a regular mesh of micrometric walls which create the side surfaces of larger inlet macrochannels. Moreover, the top portion of the bottom wafer (in or on which nanochannels may be fabricated) can be engineered to provide good mechanical stability.

The thickness of the supporting layer underneath the nanochannels can be optimized, and can be realized by controlling the depth of the inlet microchannels and outlet macrochannels or by selecting an SOI wafer with appropriate depth of buried oxide layer. The materials and thickness of top layers is also optimized for the attributes noted above.

Certain embodiments include a nanochannel delivery device comprising: an inlet microchannel; a nanochannel; and an outlet microchannel, wherein the inlet microchannel and the outlet microchannel are in direct fluid communication with the nanochannel. In specific embodiments, the nanochannel is oriented parallel to the primary plane of the nanochannel delivery device. In particular embodiments, a flow path from the inlet microchannel to the nanochannel to the outlet microchannel requires a maximum of two changes in direction.

In specific embodiments, the inlet microchannel has a length, a width, and a depth; the outlet microchannel has a length, a width, and a depth; and the nanochannel has a length, a width, and a depth. In certain embodiments, the ratio of the nanochannel length to the inlet microchannel length is between 0.01 and 10.0, and the ratio of the nanochannel length to the outlet microchannel length is between 0.01 and 10.0. In particular embodiments, the nanochannel length is greater than the inlet microchannel length and the nanochannel length is greater than the outlet microchannel length. In specific embodiments, the ratio of the nanochannel length to either the inlet microchannel length or the outlet microchannel length is between 0.2 and 5.0, between 0.3 and 3.0, between 0.4 and 2.0, or between 0.5 and 1.0. In certain embodiments, the nanochannel length is greater than the length, width, and depth of the outlet microchannel. In particular embodiments, the inlet microchannel is in direct fluid communication with the outlet microchannel via a single nanochannel.

Certain embodiments include a nanochannel delivery device comprising: an inlet microchannel; a nanochannel; an outlet microchannel; and a fluid flow path from the inlet microchannel to the outlet microchannel, where the fluid flow path requires a maximum of two changes in direction. In specific embodiments, the nanochannel is oriented parallel to the primary plane of the nanochannel delivery device. In particular embodiments, the inlet microchannel and the outlet microchannel are in direct fluid communication with the nanochannel.

Certain embodiments include a nanochannel delivery comprising: a substantially planar body comprising a first surface and a second surface opposing the first surface; a nanochannel disposed within the substantially planar body; an inlet microchannel in fluid communication with the nanochannel; and an outlet microchannel in fluid communication with the nanochannel. In particular embodiments, the inlet microchannel extends from the nanochannel to the first surface and wherein the outlet microchannel extends from the nanochannel to second surface.

Certain embodiments include a nanochannel delivery device comprising: a plurality of inlet microchannels; a plurality of nanochannels; and a plurality of outlet microchannels, where each inlet microchannel is in direct fluid communication with an outlet microchannel via a single nanochannel. In particular embodiments, the nanochannel is oriented parallel to the primary plane of the nanochannel delivery device, and/or an inlet microchannel and an outlet microchannel are in direct fluid communication with a common nanochannel. In particular embodiments, individual inlet and outlet microchannels are arranged perpendicular to a primary plane of the nanochannel delivery device; the plurality of inlet microchannels form a first array; the plurality of outlet microchannels form a second array; and the first array and the second array are overlapping so that individual inlet microchannels are distributed between individual outlet microchannels when viewed along a section taken perpendicular to the primary plane.

Certain embodiments include a nanochannel delivery device comprising: a substantially planar body including: a length, a width, and a thickness, wherein the length and the width are each greater than the thickness; an inlet surface on a first side of the substantially planar body, wherein the inlet surface is bounded by the length and the width of the substantially planar body; and an outlet surface on a second side of the substantially planar body. In particular embodiments, the outlet surface is bounded by the length and the width of the substantially planar body, and the inlet surface is substantially parallel with the outlet surface. Specific embodiments comprise a nanochannel disposed within the substantially planar body, where the nanochannel comprises an inlet end and an outlet end; an inlet microchannel in fluid communication with the nanochannel; and an outlet microchannel in fluid communication with the nanochannel, where the inlet microchannel and nanochannel are configured such that a first linear axis can extend between the inlet surface and the inlet end of the nanochannel. In particular embodiments, the outlet microchannel and nanochannel are configured such that a second linear axis can extend between the outlet surface and the outlet end of the nanochannel. In certain embodiments, a primary axis of the inlet microchannel is perpendicular to a plane that is parallel to the substantially planar body. Particular embodiments comprise an inlet macrochannel between the inlet surface and the inlet microchannel, where the inlet macrochannel comprises boundary walls that are generally perpendicular to the inlet surface. In specific embodiments, the inlet macrochannel is formed by deep reactive-ion etching. In particular embodiments, a primary axis of the outlet microchannel is perpendicular to a plane that is parallel to the substantially planar body.

Certain embodiments comprise an apparatus comprising a first nanochannel delivery device inserted into a capsule. In particular embodiments, the first nanochannel delivery device is installed perpendicular to the primary axis of the capsule. In particular embodiments, the capsule comprises a septum. In certain embodiments, the septum comprises a self-sealing material. In specific embodiments, the septum comprises silicone rubber. In certain embodiments, the septum is configured to receive an injection of a therapeutic agent.

Particular embodiments comprise a cap covering the septum. In certain embodiments, the cap comprises an orifice configured to guide a needle towards the septum. In specific embodiments, the capsule comprises a cover extending over the first nanochannel delivery device. In particular embodiments, the cover comprises one or more orifices. In certain embodiments, the one or more orifices are sized so that they do not limit diffusion of a therapeutic agent from the capsule during use. In certain embodiments, the cover is configured to protect the first nanochannel delivery device from mechanical damage. In particular embodiments, the cover is configured to protect the first nanochannel delivery device from incursion by biological tissue structures after the capsule has been implanted in a living body. In certain embodiments, the capsule comprises a first inner reservoir. In specific embodiments, the first nanochannel delivery device is in fluid communication with the first inner reservoir.

In specific embodiments, the capsule comprises a second inner reservoir in fluid communication with a second nanochannel delivery device. In certain embodiments, the first and second inner reservoir are not in fluid communication with each other. In particular embodiments, the first and second inner reservoir are separated by a wall. In specific embodiments, the first inner reservoir contains a first therapeutic agent and the second inner reservoir comprises a second therapeutic agent. In particular embodiments, the first nanochannel delivery is configured to diffuse a first therapeutic agent at a first diffusion rate and the second nanochannel delivery device is configured to diffuse the second therapeutic agent a second diffusion rate.

In certain embodiments the volume of the first inner reservoir can be modified by replacing a first removable component of the capsule with a larger removable component. In particular embodiments, the first inner reservoir comprises a coating compatible with a therapeutic substance. In specific embodiments, the capsule comprises an outer coating configured to prevent deleterious tissue encapsulation. In particular embodiments, the capsule comprises a cylindrical shape. In certain embodiments, the capsule comprises a disc shape. In certain embodiments, the capsule comprises a rectangular surface and an arched surface. In specific embodiments, the capsule comprises a uniform cross-section.

In certain embodiments, the capsule comprises one or more of the following materials: stainless steel, titanium, polyetheretherkeytone, polysulfone, epoxy, silicone rubber, polyetherketoneketone, and thermoplastic polyurethane. In particular embodiments, the capsule comprises an anchor member. In certain embodiments, the anchor member is configured to receive a suture. In specific embodiments, the capsule comprises a color coding to indicate a characteristic of the capsule or the nanochannel delivery device. In particular embodiments, the color coding indicates a characteristic of a therapeutic agent contained within the capsule. In specific embodiments the capsule comprises a translucent or transparent cover extending over the first nanochannel delivery device.

Certain embodiments include a method of fabricating a nanochannel delivery device. In particular embodiments, the method comprises: providing a first substrate; forming a plurality of nanochannels in the first substrate; forming a plurality of inlet microchannels in the nanochannels of the first substrate; providing a second substrate; forming a plurality of outlet microchannels in the second substrate; and coupling the second substrate to the first substrate, wherein each inlet microchannel is in direct fluid communication with a nanochannel.

In particular embodiments of the method, the first substrate comprises a silicon-on-insulator wafer. In certain embodiments, the height of each nanochannel is between approximately one and ten nanometers. In specific embodiments, the height of each nanochannel is between approximately ten and twenty nanometers, between approximately twenty and thirty nanometers, between approximately thirty and fifty nanometers, between approximately fifty and one hundred nanometers, or between approximately one hundred and two hundred nanometers. In certain embodiments the second substrate comprises a sacrificial release layer of indium tin oxide film on silicon. Particular embodiments further comprise depositing a glass film on the second substrate prior to forming the plurality of inlet microchannels in the second substrate. In specific embodiments, the second substrate comprises a glass wafer and the glass wafer is bonded to the first substrate and the glass wafer is ground to reduce the thickness prior to forming the plurality of outlet microchannels.

Certain embodiments include a method of fabricating a nanochannel delivery device where the method comprises: providing first substrate; forming a plurality of nanochannels on the first substrate; filling in the plurality of nanochannels with a first sacrificial material; forming a plurality of inlet microchannels in the first substrate; filling in the plurality of inlet microchannels with a second sacrificial material; forming a capping layer that covers the plurality of nanochannels; forming a plurality of outlet microchannels in the capping layer; removing the first sacrificial material from the plurality of nanochannels; and removing the second sacrificial material from the plurality of inlet microchannels.

In particular embodiments of the method, an inlet microchannel is arranged perpendicular to a primary plane of the first substrate. In specific embodiments, an outlet microchannel is arranged perpendicular to a primary plane of the first substrate. In certain embodiments of the method, an inlet microchannel is in direct fluid communication with a nanochannel. In particular embodiments, an outlet microchannel is in direct fluid communication with a nanochannel.

In certain embodiments of the method, the first substrate comprises a silicon-on-insulator wafer comprising an internal oxide layer. In particular embodiments, the inlet and outlet microchannels are patterned using a photolithography process. In certain embodiments, forming the plurality of inlet microchannels comprises etching material from the first substrate, and the etching is terminated at the internal oxide layer. In particular embodiments of the method, forming a plurality of inlet macrochannels comprises etching material from a back side of the first substrate, and the etching is terminated at the internal oxide layer.

In certain embodiments the removal of the internal oxide layer after etching material to form the inlet microchannel and inlet macrochannels opens a pathway between the inlet microchannels and inlet macrochannels. In particular embodiments of the method, each nanochannel is between approximately one and ten nanometers deep, between approximately ten and twenty nanometers deep, between approximately twenty and thirty nanometers deep, between approximately thirty and forty nanometers deep, or between approximately forty and two hundred nanometers deep.

In certain embodiments of the method, the first sacrificial material can be subsequently removed by selective etching. In particular embodiments, the first sacrificial material is tungsten. In specific embodiments, the second sacrificial material can be subsequently removed by selective etching. In certain embodiments of the method, the second sacrificial material is selected from the group consisting of: tungsten, copper, doped glass, and undoped glass. In particular embodiments, the second sacrificial material is filled into the plurality of inlet microchannels so that the second sacrificial material extends above the top of the inlet microchannels and is planarized by chemical-mechanical planarization (CMP).

In particular embodiments of the method, the capping layer is selected from silicon nitride, silicon oxide, silicon carbonitride, silicon carbide, and silicon. In certain embodiments, the capping layer comprises multiple depositions of materials comprising tensile and compressive stresses such that the net capping layer stress is tensile. In certain embodiments of the method, the capping layer is between approximately 0.5 and 1.0 microns thick, between approximately 1.0 and 2.0 microns thick, between approximately 2.0 and 4.0 microns thick, or between approximately 4.0 and 10.0 microns thick. In specific embodiments, the capping layer is greater than 10.0 microns thick.

Particular embodiments comprise a method of fabricating a nanochannel delivery device, where the method comprises: providing a first substrate; forming a plurality of nanochannels on a first side of the first substrate; filling in the plurality of nanochannels with a sacrificial material; coupling an initial capping layer to the first side of the first substrate; forming a plurality of inlet microchannels in the capping layer; preparing a second substrate with a bonding layer; coupling the second substrate to a second side of the first substrate; removing a first portion of the second substrate; providing an additional capping layer to the second substrate; forming a plurality of outlet microchannels in the second substrate; and removing the sacrificial material to open the plurality of nanochannels.

In certain embodiments of the method, the second substrate comprises a release layer, and the release layer can be selectively removed to cause separation of the second substrate from the first substrate. In particular embodiments of the method, an outlet microchannel is in direct fluid communication with the a nanochannel. In certain embodiments, the first substrate comprises a silicon-on-insulator wafer comprising an internal oxide layer. In specific embodiments, forming the plurality of inlet microchannels comprises etching material from the capping layer, and the etching is terminated at the internal oxide layer.

In certain embodiments, forming a plurality of inlet macrochannels comprises etching material from a back side of the first substrate, and the etching is terminated at the internal oxide layer. In particular embodiments, the removal of the internal oxide layer after etching material to form the inlet microchannel and inlet macrochannels opens a pathway between the inlet microchannels and inlet macrochannels.

In certain embodiments, each nanochannel is formed between approximately one and ten nanometers deep, between approximately ten and twenty nanometers deep, between approximately twenty and thirty nanometers deep, between approximately thirty and forty nanometers deep, or between approximately forty and two hundred nanometers deep.

In particular embodiments, the sacrificial material can be subsequently removed by selective etching. In specific embodiments, the sacrificial material is tungsten. In certain embodiments, the initial capping layer is silicon nitride deposited by plasma enhanced chemical vapor deposition. In certain embodiments of the method, the initial capping layer is between approximately 0.01 and 0.5 microns thick, between approximately 0.5 and 1.0 microns thick, between approximately 1.0 and 2.0 microns thick, between approximately 2.0 and 4.0 microns thick, or between approximately 4.0 and 10.0 microns thick. In specific embodiments of the method, the initial capping layer is greater than 10.0 microns thick. In certain embodiments of the method, the initial capping layer is selected from silicon nitride, silicon oxide, silicon carbonitride, silicon carbide, and silicon. In particular embodiments, the initial capping layer comprises multiple depositions of materials comprising tensile and compressive stresses such that the net capping layer stress is tensile. In certain embodiments of the method, the bonding layer is selected from the group consisting of benzocyclobutene, silicon oxide, copper, doped glass, gold and gold alloys.

In certain embodiments, the method of coupling the second substrate to the first substrate is selected from the group consisting of anodic bonding, fusion bonding, and thermocompression bonding.

Particular embodiments include a nanochannel delivery device comprising: a plurality of inlet microchannels, where each of the inlet microchannels has a length, a width, and a depth, and where the inlet microchannel length is greater than the inlet microchannel width and depth; a plurality of outlet microchannels, where each of the outlet microchannels has a length, a width, and a depth; and a plurality of nanochannels in fluid communication with the plurality of inlet microchannels and outlet microchannels. In certain embodiments, the plurality of inlet microchannels are arranged so that the inlet microchannel width and depth define a first plane that is parallel to the primary plane of the nanochannel delivery device; and the plurality of outlet micro channels are arranged so that the outlet micro channel width and depth define a second plane that is parallel to the primary plane of the nanochannel delivery device.

Particular embodiments include a method of treating a condition of a person, the method comprising: providing a nanochannel delivery device as described herein; providing a reservoir in fluid communication with the nanochannel delivery device; providing a substance in the reservoir, where the substance is configured to treat the condition; and administering the substance to the person via the nanochannel delivery device. In particular embodiments of the method, the substance is selected from the group consisting of: leuprolide, letrozole, laptinib, buprenorphine, interferon, and zidovudine. In certain embodiments, the condition is selected from the group consisting of: prostate cancer, breast cancer, opiate dependencey, giant cell angioblastoma and HIV. In particular embodiments of the method, administering the substance to the person via the nanochannel delivery device comprises subcutaneously inserting the nanochannel delivery device into the person.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The term "inlet microchannel" is defined as a microchannel through which a molecule travels prior to entering a nanochannel in a nanochanneled delivery device.

The term "outlet microchannel" is defined as a microchannel through which a molecule travels immediately prior to exiting a nanochanneled delivery device.

The term "nanochannel" is defined as a channel with a cross-section having at least one dimension (e.g. height, width, diameter, etc.) that is less than 200 nm.

The term "macrochannel" is defined as a channel with a cross-section having a maximum dimension (e.g. height, width, diameter, etc.) that is greater than about 10 μm.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

FIGS. 1A-1J are schematic views of a manufacturing process according to an exemplary embodiment.

FIG. 4A-4L are schematic views of a manufacturing process according to an exemplary embodiment.

FIGS. 5A-5H are schematic cross-section views of a nanochannel delivery device during the manufacturing process according to an exemplary embodiment.

FIG. 7 is a cross-sectional side view of a schematic of an exemplary embodiment of a nanochannel delivery device.

FIGS. 8A-8I are schematic views of a manufacturing process according to an exemplary embodiment.

FIG. 17 is scanning electron microscope image of a portion of a nanochannel delivery device according to an exemplary embodiment.

FIG. 18 is a table of materials that may be used in exemplary embodiments of manufacturing processes.

DETAILED DESCRIPTION OF ILLUSTRATIVE EMBODIMENTS

Protocol 1: Bonded Capping Layer

FIGS. 1a-1j, 2A-2E, and 3A-3G provide illustrations of steps performed in an exemplary first method of manufacturing a nanochannel delivery device. Specific dimensions are provided for purposes of illustration only, and it is understood that other exemplary embodiments may comprise different dimensions.

In one exemplary embodiment manufactured according to this protocol, the top layer is a cover of a 5 µm thick evaporated glass layer and the bottom wafer is a 4 inch SOI wafer with a 30 µm device layer, and a 500 µm bulk layer, so that the supporting layer under the nanochannels has 30 µm thickness. In this exemplary structure, the inlet and outlet microchannels are 5 µm by 5 µm, and the in-plane dimension of each nanochannel is 5 µm by 5 µm. The space between adjacent openings (e.g., the distance between adjacent nanochannels) is 2 µm. The inlet macrochannel under the support network is approximately 200 µm by 200 µm up through the 500 µm thick bulk layer.

A general overview of this method of manufacturing will first be presented, followed by a more detailed discussion of the features comprised in the nanochannel delivery device. In this embodiment, fabrication of the nanochannel delivery device does not utilize chemical mechanical polishing (CMP), and the microfabrication protocol comprises the following steps. Starting with a SOI (silicon on insulator) wafer (see FIG. 2A), a hard mask layer such as silicon nitride film or LTO (low temperature oxidation) film that will protect underneath silicon during thermal oxidation process is deposited. If silicon nitride is used, a silicon dioxide pad layer may be deposited before nitride deposition. As an alternative, the bottom substrate can also be a silicon wafer instead of SOI if the etching process rates are well characterized. In this case, the etching depth is controlled by timing.

The nanochannel areas can then be patterned on the mask layer using photolithography process. (see FIGS. 1(a) and 2B), and the mask materials on nanochannel areas are selectively removed but do not affect underneath silicon. A combination of dry etching, and short time wet etching may be applied for this purpose. Then a silicon dioxide film (with a thickness that is well-controlled) can be deposited on bare silicon area by thermal oxidation. In this embodiment, the thickness of the oxidation layer is used to define the height of nanochannels, and the mask layer is stripped.

A mask layer suitable for deep silicon etching can then be deposited. The mask layer should be able to be patterned, and have a high selectivity to silicon during deep silicon etching process. Depending on the technique for deep silicon etching, a layer of silicon oxide, photoresist, or metal film may be used.

Figure 2A:
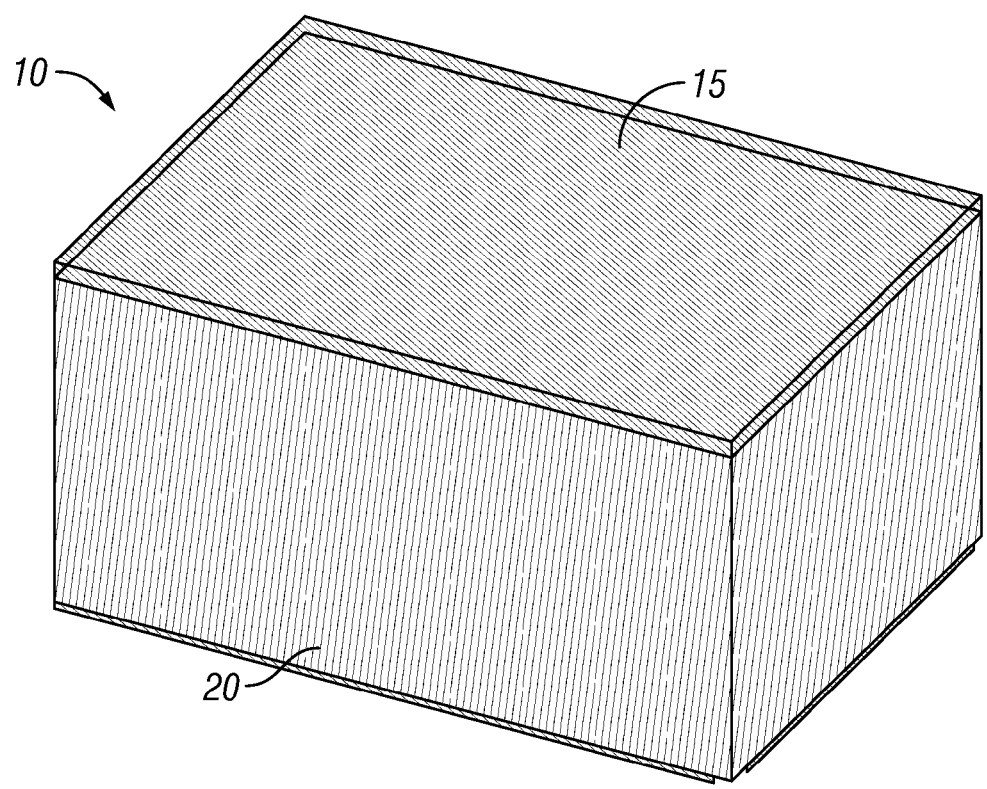
FIGS. 2A-2E are perspective views of a first portion of a nanochannel delivery device during the manufacturing process.
Figure 2B:
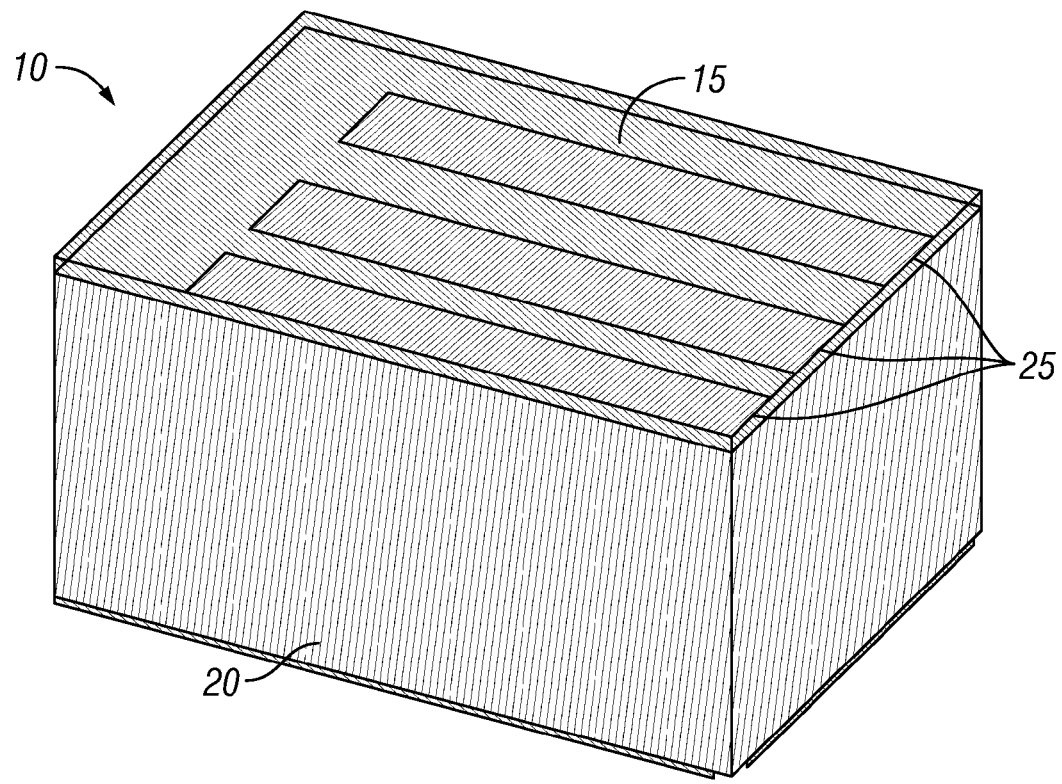
Figure 2C:
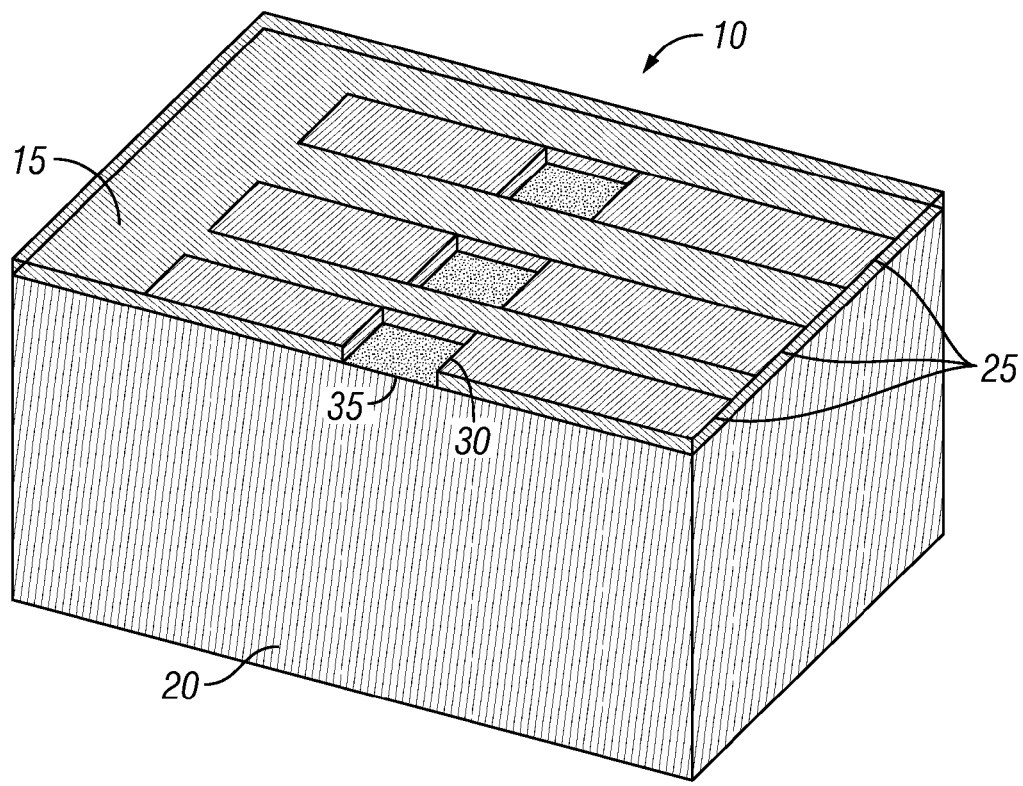

In this embodiment, the inlet microchannels are patterned on the mask layer, and the inlet microchannels are etched down to the oxide layer of the SOI wafer by deep RIE (Reactive Ion Etch) or ICP (Inductive Coupled Plasma) technique, as shown FIGS. 1(b) and 2C. If a silicon wafer is used, the etching depth is determined by etching rate and time.

Figure 2D:
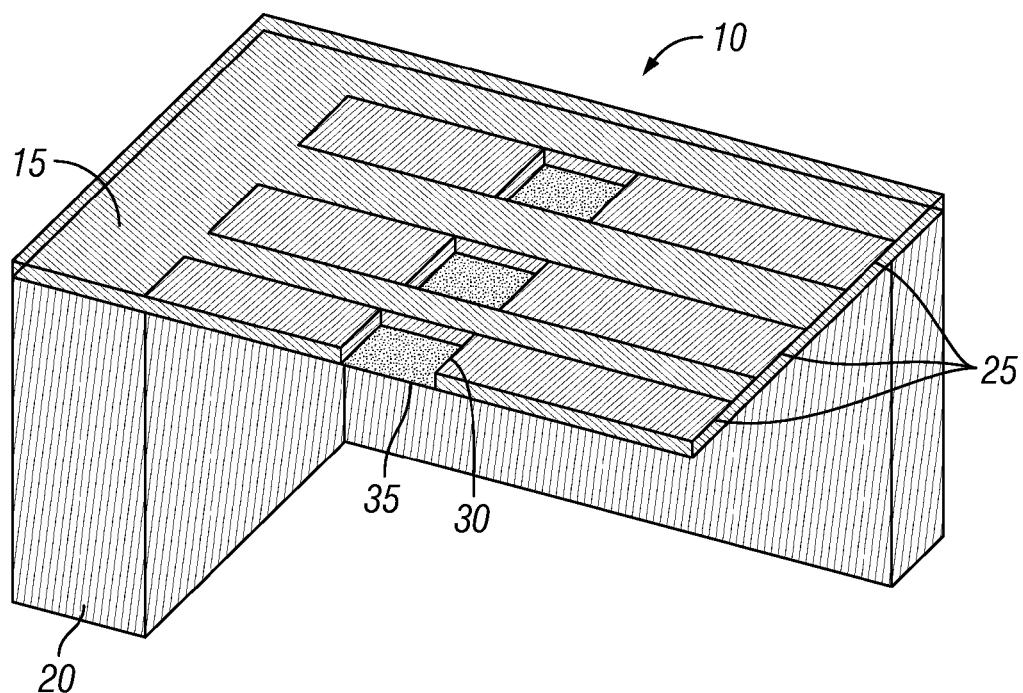

The inlet macrochannels (the large openings from the back) are laid out and etched to the oxide layer of SOI wafer, as shown in FIGS. 1(c) and 2D, and the exposed oxide areas are cleaned by HF solution. (see FIGS. 1(d) and 2E). To fabricate the top cover of the nanochannel delivery devices in this embodiment, starting with a support wafer (e.g., a silicon wafer), a sacrificial layer is deposited. (see FIGS. 1(e), 1(f) and 3A). This sacrificial layer (e.g., indium tin oxide (ITO)), is selected so that it can be removed in a solution that is safe for silicon and top cover materials.

Figure 3A:
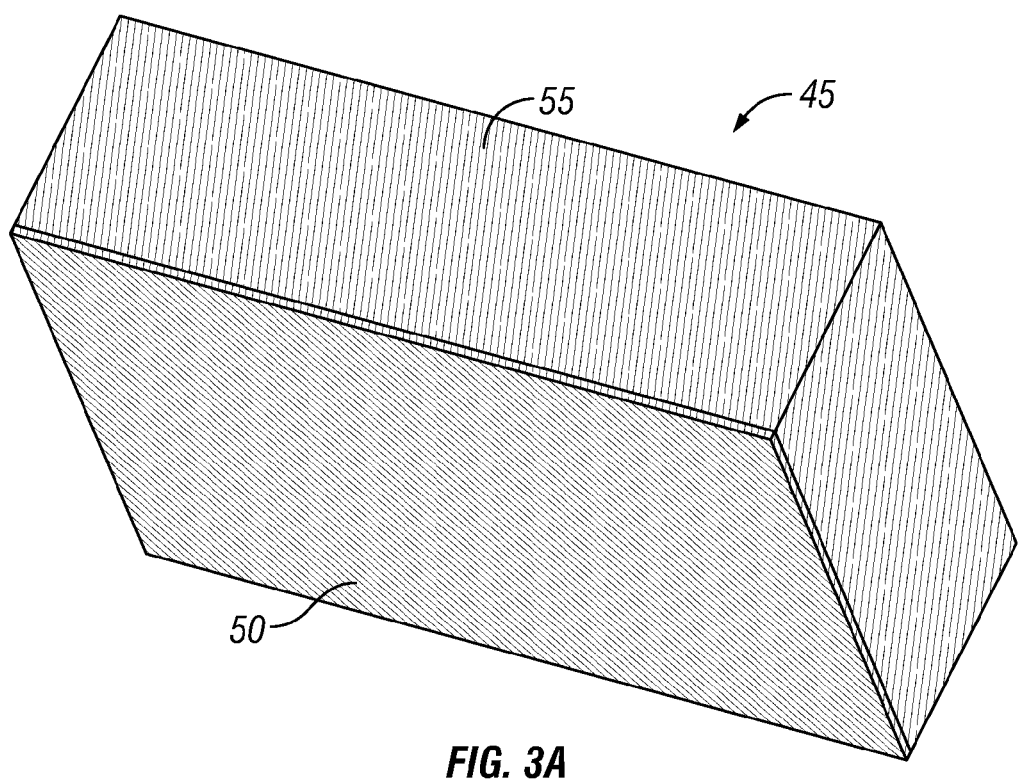
FIGS. 3A-3F are perspective views of a second portion of a nanochannel delivery device during the manufacturing process.
Figure 3B:
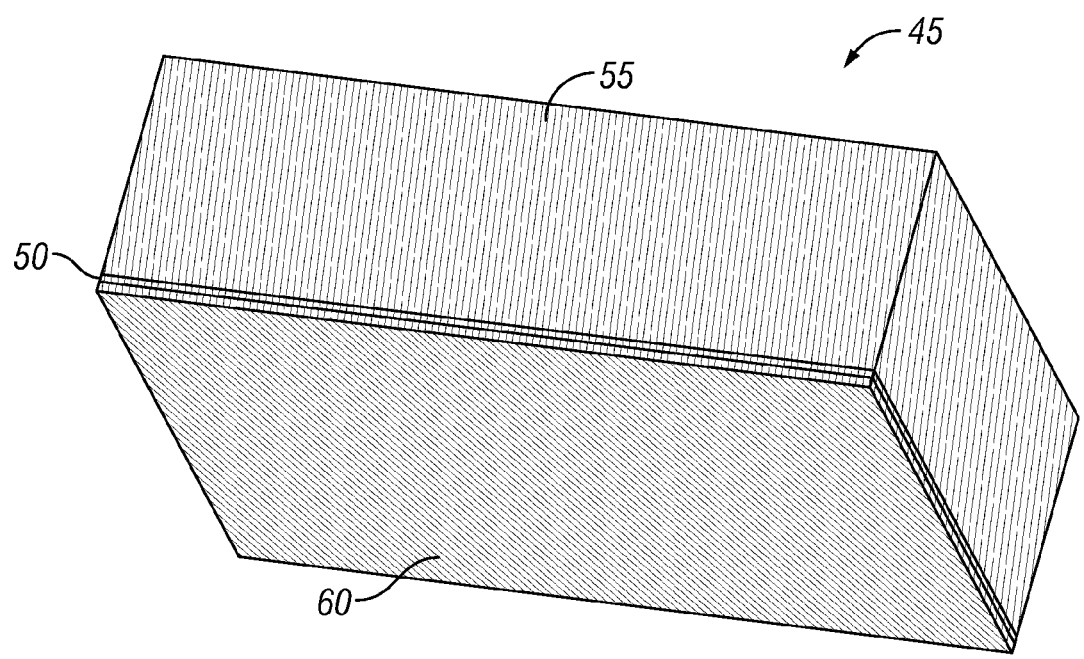
Figure 3C:
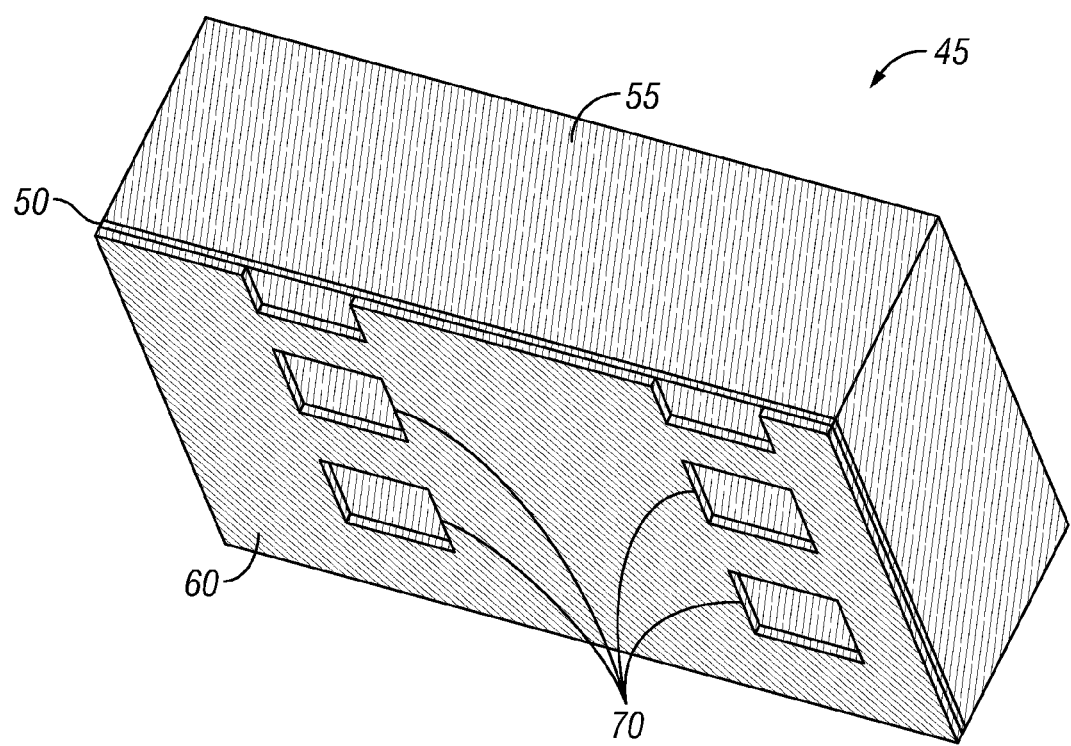

The top cover of the nanochannel delivery devices is deposited on the sacrificial layer (see FIGS. 1(g) and 3B), and the outlets are patterned on the structure, as shown in FIGS. 1(h) and 3C. As an alternative, a lift-off technique may be applied for the cases of sputtered glass or e-beam evaporated glass. The materials may be any suitable material, e.g. spin-on-glass, sputtered glass, e-beam evaporated glass, ITO-glass sandwich, silicon, polymer, etc. The materials may include glass and glass materials known to those skilled in the art to bond to silicon by specific means, e.g., anodic bonding or fusion bonding. The materials should be able to bond to silicon by certain means. For instance of glass, anodic bonding can be applied. A spin-on-glass layer may also applicable. Depending on the surface quality, a planarization process may be needed.

Figure 3D:
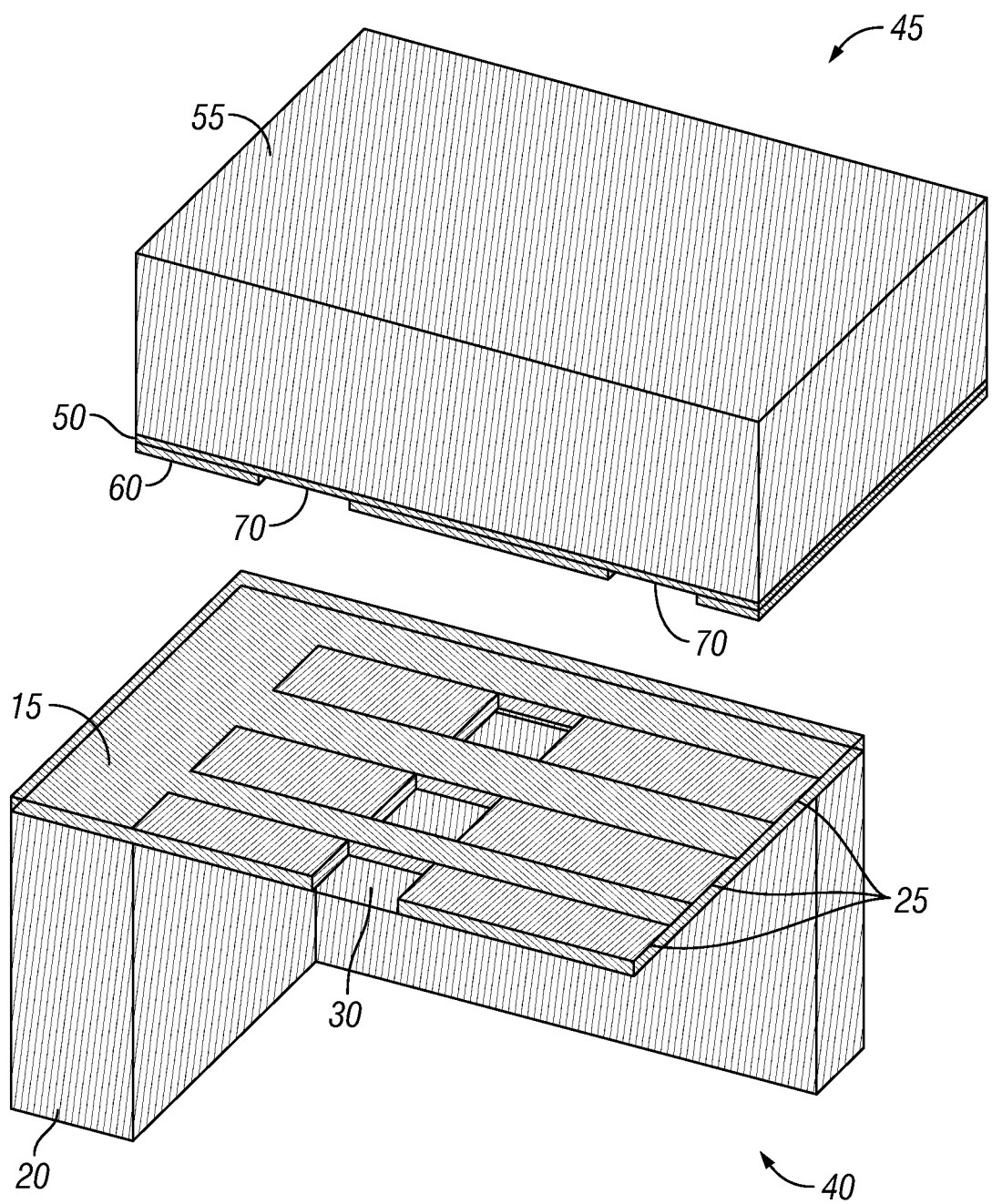
Figure 3E:
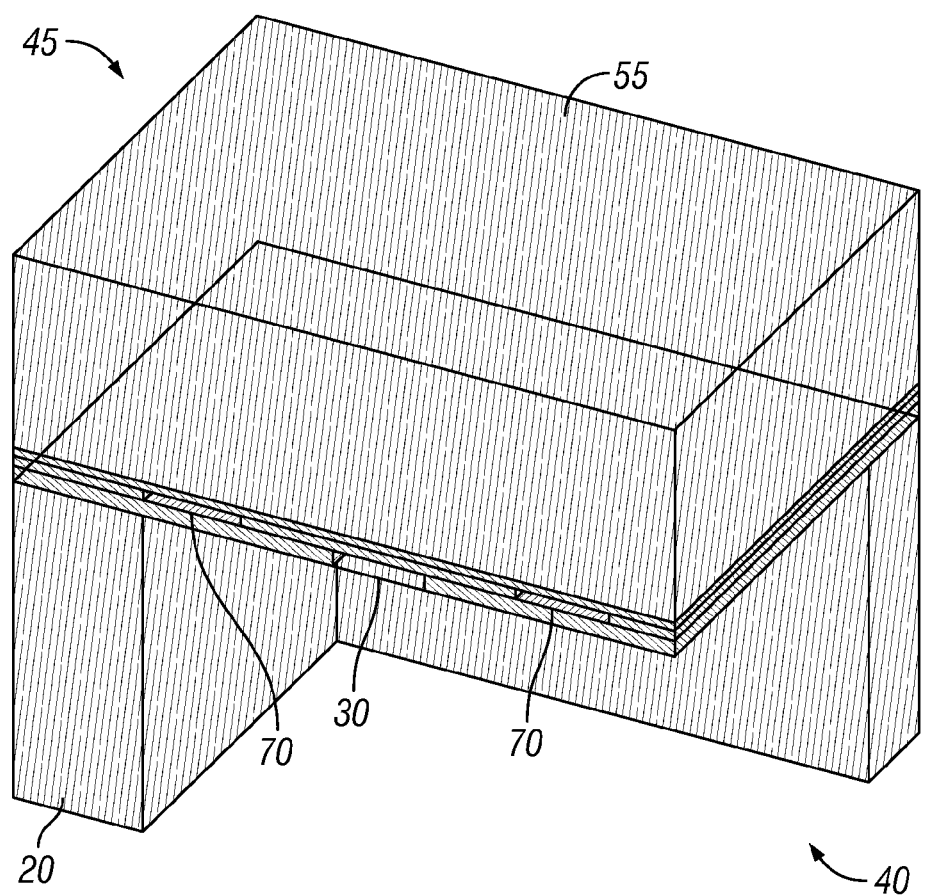
Figure 3F:
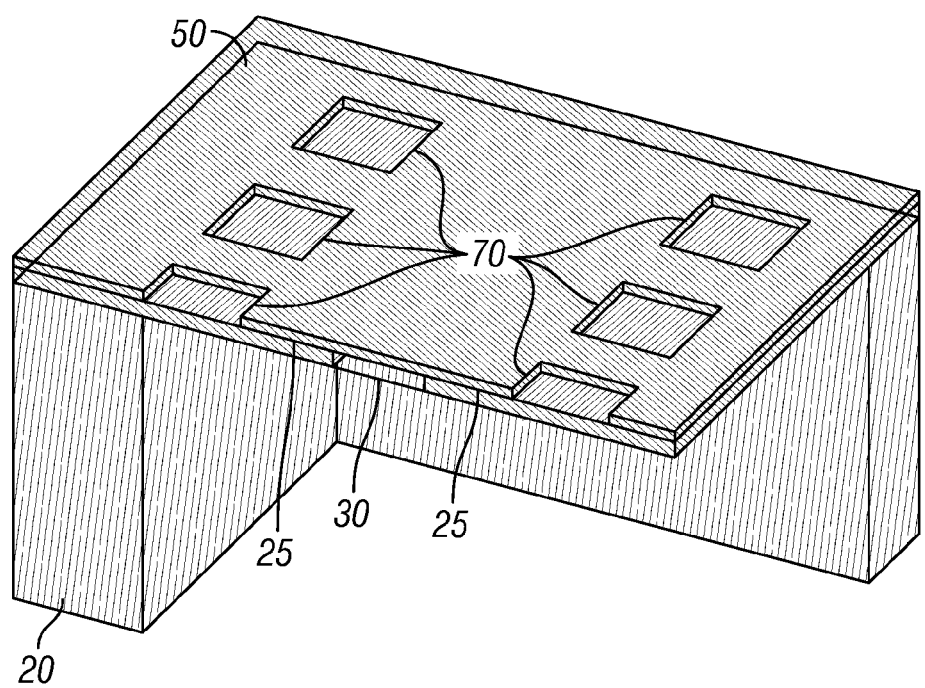

The structure wafer and the top cover are bonded together by a technique such as anodic bonding or Si—Si direct bonding or intermediate layer aided bonding, as shown in FIGS. 1(c), 3D, and 3E, and the support wafer of top cover is removed (as shown in FIGS. 1(f) and 3F). Finally, the individual nanochannel delivery devices are obtained by dicing the wafer, and cleaning.

In another exemplary embodiment manufactured according to this protocol, while keeping the bottom silicon substrate is the same 4 inch SOI wafer with a 30 µm device layer and a 500 µm bulk layer as that mentioned in above embodiment, the top layer is a 10 µm thick glass film. The 10 um thick glass film is manufactured by thinning a thicker glass layer. To make this thin film, a 100 um to 500 um thick glass wafer is bonded to the structural silicon substrate. A planarization technique such as backgrinding, or lapping, or CMP, or chemical etching, or dry etching is then applied to thin the glass layer until the designed thickness such 10 um is reached. The outlets are then patterned on the thinned glass film, and etched down to the underneath silicon surface to open the outlets. In this exemplary structure, the inlet and outlet microchannels are 5 µm by 5 µm, and the in-plane dimension of each nanochannel is 5 µm by 5 µm. The space between adjacent openings (e.g., the distance between adjacent nanochannels) is 2 µm. The inlet macrochannel under the support network is 200 µm by 200 µm up through the 500 µm thick bulk layer.

Referring specifically now to FIGS. 2A-2E and 3A-3F, a more detailed view of the features of nanochannel delivery device 100 is provided. Referring initially to FIG. 2A, an SOI wafer 10 comprises a top layer 15 over a substrate 20 and separated by an oxide layer 35. As shown in FIG. 2B, a series of nanochannels 25 are formed using a pattern mask in top layer 15. One or more inlet microchannels 30 is formed using a pattern mask in each nanochannel 25, as shown in FIG. 2C, exposing an oxide layer 35 between the substrate 20 and the top layer 15. For purposes of clarity not all features, for example inlet microchannels 30, are labeled in the figures.

Figure 2E:
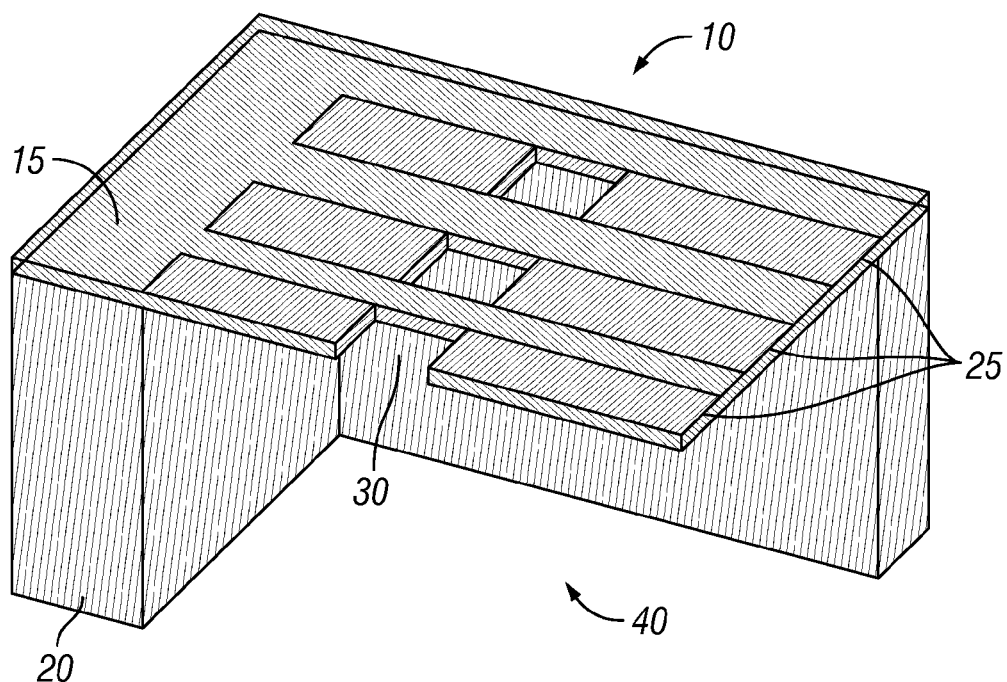

As shown in FIG. 2D, a portion of substrate 20 is removed using a pattern mask from below the oxide layer 35. Oxide layer 35 is then removed (as shown in FIG. 2E), and inlet microchannels 30 are formed to allow passage of material through the substrate 20 and top layer 15. At this stage, the lower portion 40 of nanochannel delivery device 100 is complete.

Referring now to FIGS. 3A-3F, the fabrication of the upper portion 45 of nanochannel delivery device 100 begins with a sacrificial layer 50 deposited on a support substrate 55. In addition, an additional layer 60 (e.g., spin-on-glass, sputtered glass, e-beam evaporated glass, ITO-glass sandwich, silicon, polymer, etc.) may be used in processes utilizing a lift-off technique, as shown in FIG. 3B. Exit microchannels 70 are formed in sacrificial layer (and additional layer 60, if utilized) as shown in FIG. 3C.

Figure 3G:
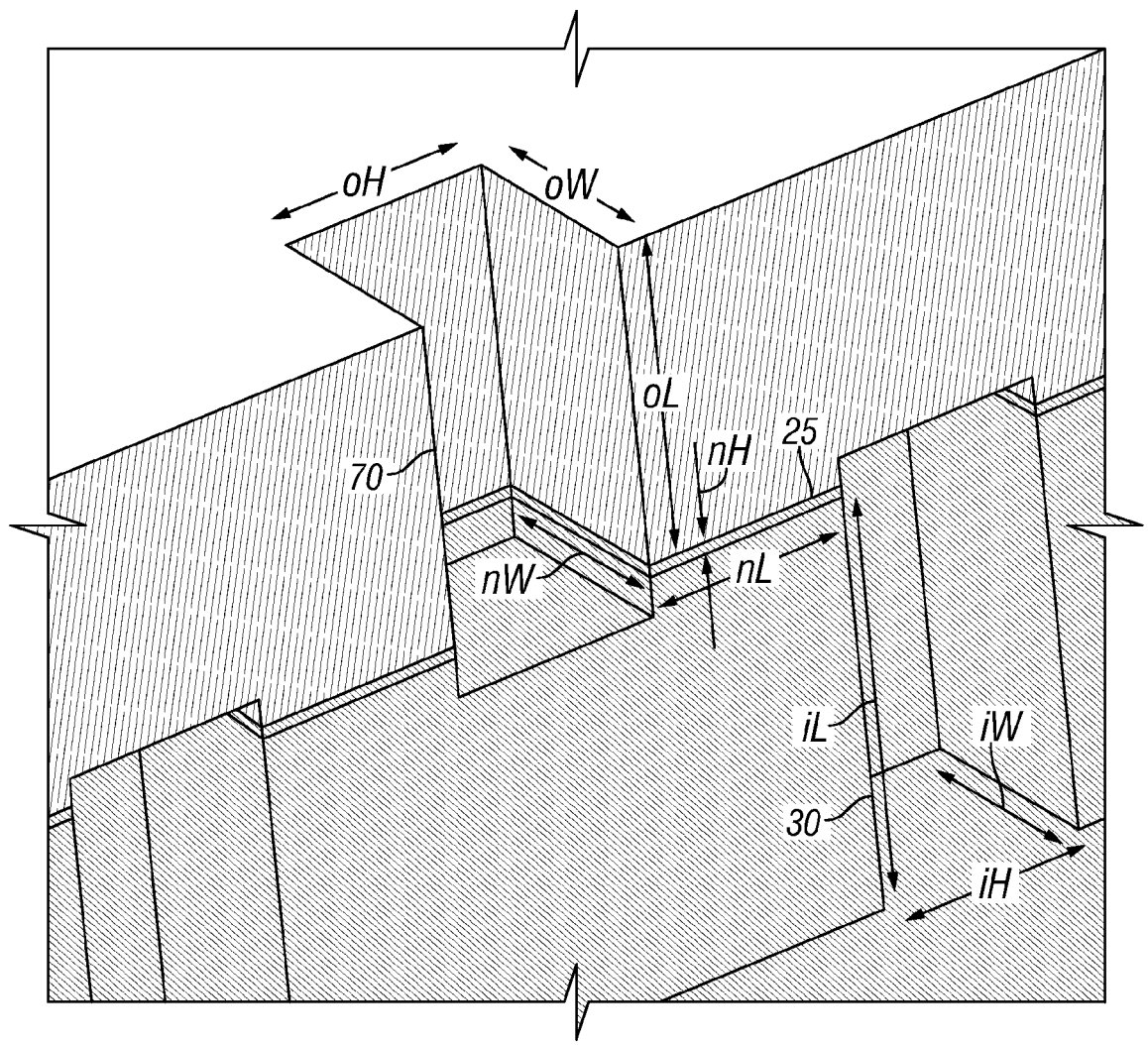
FIG. 3G is a partial perspective view of a nanochannel delivery device with representative dimensions labeled.

At this stage, upper portion 45 is ready to be bonded to lower portion 40 of nanochannel delivery device 100. It is understood, the designations "upper" and "lower" are used only for purposes of clarification in the description of the figures, and do not dictate the relationship of components during use of the device. As shown in FIGS. 3D and 3E, upper portion 45 and lower portion 40 are bonded together (through, e.g., anodic bonding or Si—Si direct bonding or intermediate layer aided bonding). Support substrate 55 is removed from upper portion 45, and nanochannel delivery device 100 is completed, as shown in FIGS. 3F and 3G. The embodiment shown in FIG. 3G comprises optional tapered surfaces in the transitions between outlet microchannels 70 and nanochannels 25, as well as between nanochannels 25 and inlet microchannels 30.

As shown in FIG. 3G, nanochannels 25 lie in a plane parallel to the primary plane of nanochannel delivery device 100 (e.g., the plane defined by the larger dimensions [in this example, L and W] of nanochannel delivery device 100). Such a configuration allows for the length of nanochannel 25 (e.g., approximately the distance between adjacent outlet 70 and inlet 30) and the height and width of the nanochannel to be varied without varying the length L, width W, and thickness T of nanochannel delivery device 100. The thickness T of nanochannel delivery device 100 can therefore be based on other criteria (such as mechanical integrity) rather than the need to control the flow of a substance being delivered via nanochannel delivery device 100.

The embodiments shown in FIGS. 3A-3G also provide for each outlet 70 to be in fluid communication with any inlet 30 via a single nanochannel 25. Such a configuration can provide for greater control over the diffusion of a substance being delivered via nanochannel delivery device 100. For example, the diffusion rate through nanochannel delivery device 100 is more closely related to the dimensions of nanochannel 25, as compared to configurations that have numerous nanochannels in fluid communication with a single extended inlet. In such configurations, the inlet (rather than the nanochannel) may become a restriction on flow and limit the ability to control the flow by varying the dimensions of the nanochannel.

As shown in the detailed view of FIG. 3G (not to scale), nanochannel 25 comprises a length nL, a width nW and a height nH. Outlet microchannel 70 comprises a length oL, a width oW, and a height oH. In addition, inlet microchannel 30 comprises a length iL, a width iW and a height iH. As shown in FIG. 3G, the "length" of each channel is measured along the path that a molecule would travel as it moves from inlet microchannel 30, through nanochannel 25, and out through outlet microchannel 70. In certain embodiments oL=4 um, oW=5 um, oH=5 um while nH=50 nm, nW=4 um, and nL=5 um and oL=30 um, oW=5 um, oH=5 um.

In certain embodiments, the ratio of oL/nL or iL/nL can be 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 20, 30, 40 50, 60, 70, 80, 90, or 100.

Protocol 2: Multilayered Structure with Bonded Capping Layer

In a second embodiment, a multilayered nanochannel structure can be fabricated by modifying the above-described protocol 1. This embodiment comprises the following steps. Starting with a SOI (silicon on insulator) silicon wafer, a silicon dioxide layer (with a thickness that is well-controlled) is deposited by thermal oxidation. The thickness of the oxidation layer can be used to define the height of nanochannels. As an alternative, the bottom substrate can also be silicon wafer instead of SOI if the etching process rates are well characterized. The nanochannel areas can be patterned on the oxide layer using photolithography process.

The silicon oxide on non-nanochannel areas can be selectively removed but not affect the oxide on nanochannel area. (See FIG. 4(*a*)). A polysilicon structure layer can be deposited on the top of oxide nanochannel spacing layer. (see FIG. 4(*b*)). A second defined thickness oxide layer can be deposited again, and the nanochannel areas can be patterned on the oxide layer using photolithography process. The silicon oxide on non-nanochannel areas can be selectively removed but do not affect the oxide on nanochannel area. (See FIG. 4(*c*)). This process finishes the second layer of nanochannels. The previous two steps can be repeated to achieve desired number of layers.

As an alternative to the previous steps, the silicon oxide nanochannel spacing layer and multilayer structure layer may also use other materials. For example, an aluminum film as nanochannel spacing layer, and evaporated glass film as multilayer structure layers.

A first mask layer suitable for deep silicon etching can be deposited. The mask layer should be able to be patterned, and have high selectivity to silicon during deep silicon etching process. Depending on the technique for deep silicon etching, a layer of silicon oxide, photoresist, or metal film may be used.

The inlet microchannels are patterned on the first mask layer, and a second mask layer is deposited on the top of first mask layer. The inlet microchannels are patterned on the both first and second mask layers. The outlet microchannels are etched down to a certain depth close to oxide layer of the SOI wafer, and the second mask layer is stripped to expose the first mask layer. The outlet microchannel is etched through multiple layers of the nanochannel spacing layer and structure layer. A combination of wet etching and DRIE may be applied. This will also etch the inlet down to the insulator layer of SOI wafer. (See FIG. 4(*d*)). If a silicon wafer is used, the etching depth is determined by etching rate and time. Then the inlet macrochannels on the back are laid out and etched to the oxide layer of SOI wafer (see FIG. 4(*e*)), and the oxide on the exposed areas is cleaned. (See FIG. 4(*f*)).

To fabricate the top cover of the nanochannel delivery devices, starting with a support wafer (e.g., a silicon wafer), a sacrificial layer is deposited. (See FIG. 4(*h*)). This sacrificial layer is selected so that it can be removed in a solution that is safe for silicon and top cover materials. The top cover of the nanochannel delivery device is deposited on the supporting wafer and the inlet microchannels are etched. A lift off technique may be applied for certain cases. (See FIG. 4(*i,j*)). The materials may include, for example, spin-on-glass, sputtered glass, e-beam evaporated glass, ITO-glass sandwich, silicon, etc. The materials should be able to bond to silicon by some means. For instance, a transparent glass layer can be deposited by e-beam evaporation. A spin-on-glass layer may also usable. Depending on the surface quality, a planarization may be needed. The structure wafer from the previous step and the top cover can be bonded together by a technique such as anodic bonding or Si—Si direct bonding or intermediate layer aid bonding. (See FIG. 4(*k*)). The support wafer of top cover can be removed (See FIG. 4(*l*)), and the devices obtained by dicing the wafer and cleaning.

Protocol 3: Monolithically Fabricated Capping Layer

As a third embodiment, a nanochannel structure can be fabricated monolithically (e.g., without bonding) and optionally utilizing CMP in the process. This exemplary microfabrication protocol comprises the following steps as shown in FIGS. 5A-5H.

Specific dimensions are provided for purposes of illustration only, and it is understood that other exemplary embodiments may comprise different dimensions. In this embodiment, the top layer is approximately 2 μm of deposited silicon nitride. This embodiment also comprises a bottom wafer that is a 8 inch SOI wafer with a 30 μm device layer, and a 725 μm bulk layer, so that the supporting layer under the nanochannels has 30 μm thickness. In this exemplary structure, the openings for the inlet and outlet microchannels are 3 μm by 5 μm, and the in-plane dimension of each nanochannel is 3 μm by 5 μm. The space between adjacent microchannel openings is 2 μm. As in previously-described embodiments, the inlet macrochannel under the support network is approximately 200 μm by 200 μm up through the 725 μm thick bulk layer.

Starting with an SOI (silicon on insulator) wafer 210, a nanochannel spacing layer 220 (with a thickness that is well controlled, for example, ±5% over the relevant portion of SOI wafer 210) is deposited. The thickness of spacing layer 220 can be used to define the height of the nanochannels. This spacing layer 220 is a sacrificial layer, and the material will be removed in a subsequent step, so the silicon surface immediately under it is the "floor" of the eventually formed nanochannels. The spacing material should have a high wet etch selectivity to other materials in the nanochannel delivery device (nDD). As an example, a thin film of tungsten, germanium, or silicon oxide can be used for the nanochannel spacing layer 220.

Figure 5A:
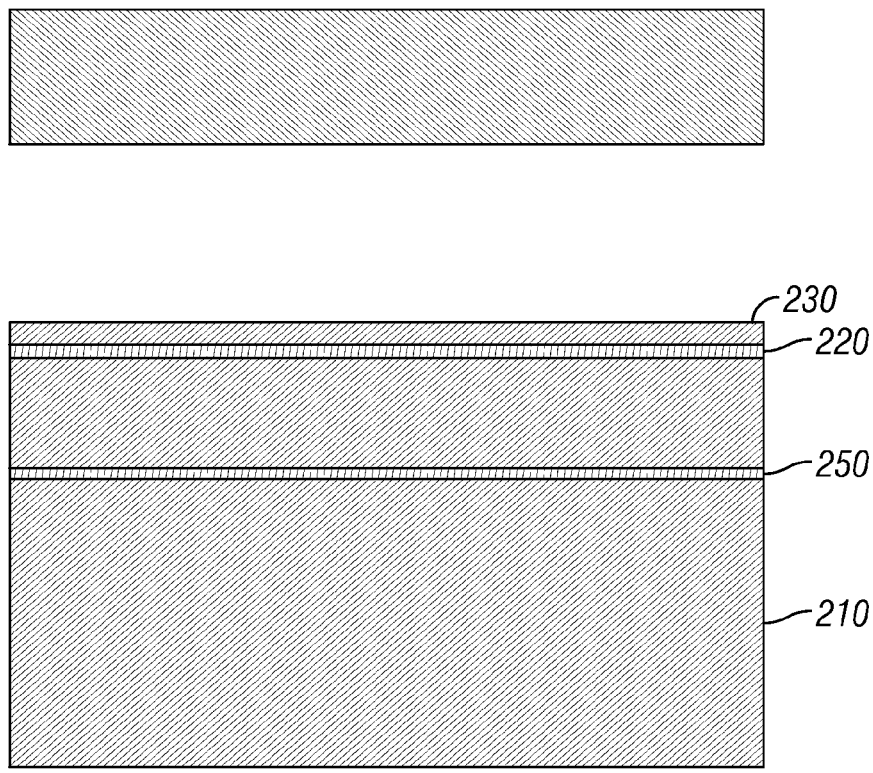

As shown in FIG. 5A, a capping layer 230 is deposited over the nanochannel spacing layer 220. Capping layer 230 will ultimately be the "ceiling" of the nanochannels. Silicon nitride, silicon oxide, silicon carbide, or other material which has a high etch selectivity to the material for spacing layer 220 may be used for capping layer 230.

Figure 5B:
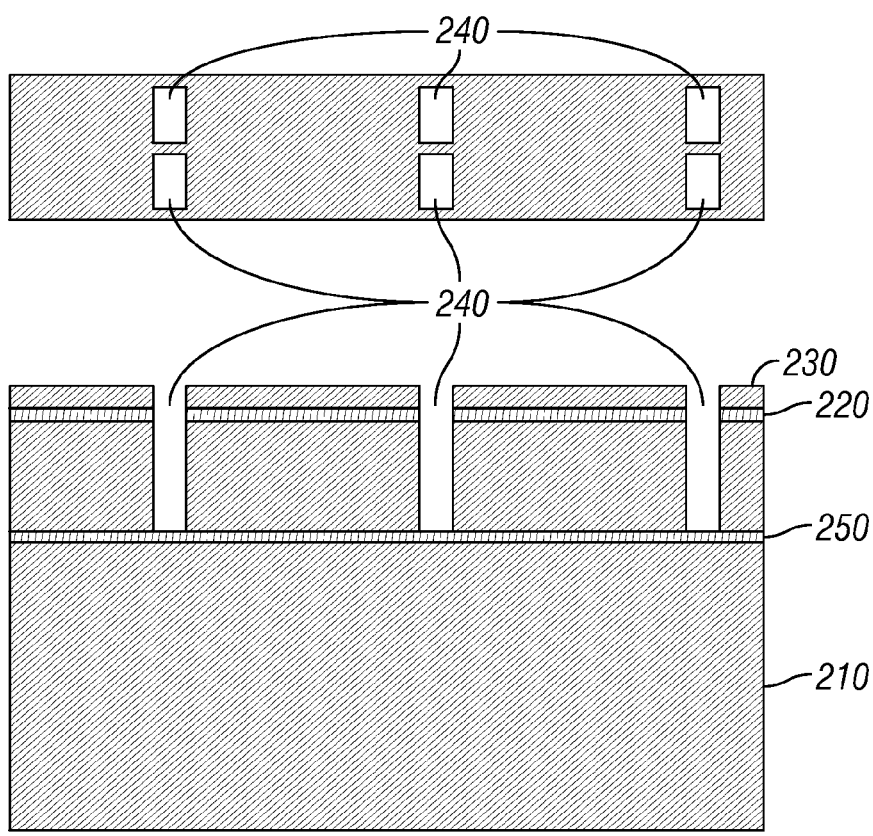

A mask layer (not shown) suitable for deep reactive-ion etching (DRIE) is deposited, and the inlet microchannels 240 are patterned on the mask layer using photolithography. As shown in FIG. 5B, the DRIE process(es) etch microchannels 240 through the capping layer 230 and spacing layer 220 and silicon down to the buried oxide layer 250 of SOI wafer 210. The mask layer can then be removed.

As shown in FIG. 5C, inlet microchannels 240 are filled with a fill material 260 that can be polished by CMP or etched. Non-limiting examples of fill material 260 include copper, tungsten, polysilicon, or phosphosilicate glass, each deposited by techniques known in the art. Fill material 260 should have a wet etch with high selectivity to silicon and the material of capping layer 230. In this exemplary embodiment, fill material 260 only needs to fill in the top of inlet microchannels 240. A CMP or etch back process can be used to remove the excess fill material 260 that extends above or outside of inlet microchannels 240. The surface of the remaining fill material 260 should be above the level of spacing layer 220.

Referring now to FIG. 5D, additional material may be deposited onto capping layer 230. The areas of capping layer 230 and spacing layer 220 above and between the inlet microchannels 240 can be patterned using a photolithography process. The spacing layer 220 and capping layer 230 outside of the inlet nanochannels 240 (e.g., regions 221 and 231) can be etched to or slightly below the silicon surface.

Figure 5E:
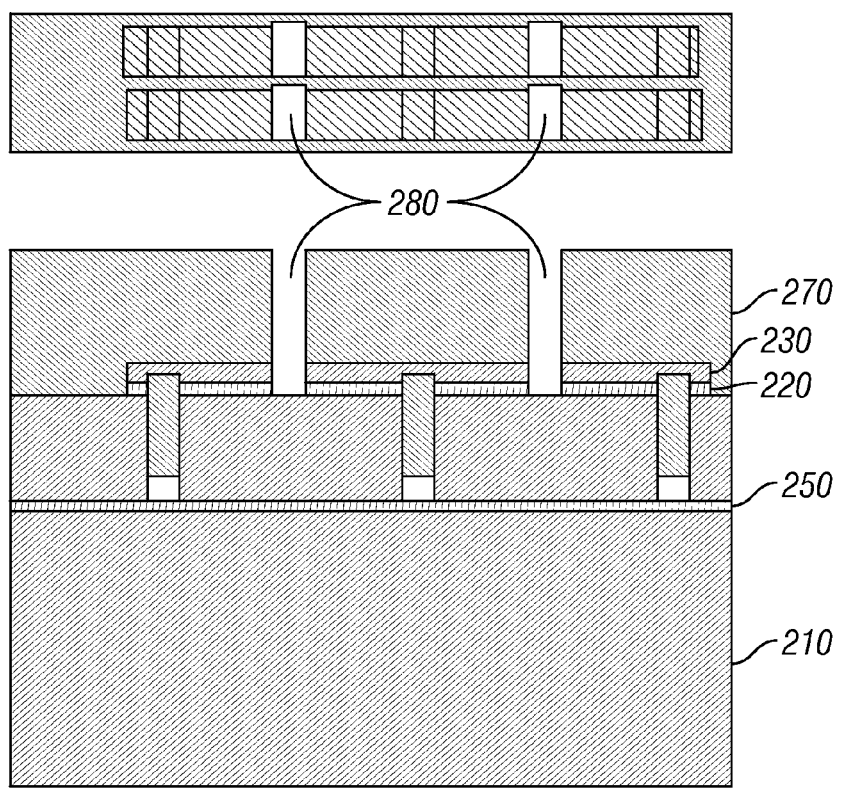
Figure 5F:
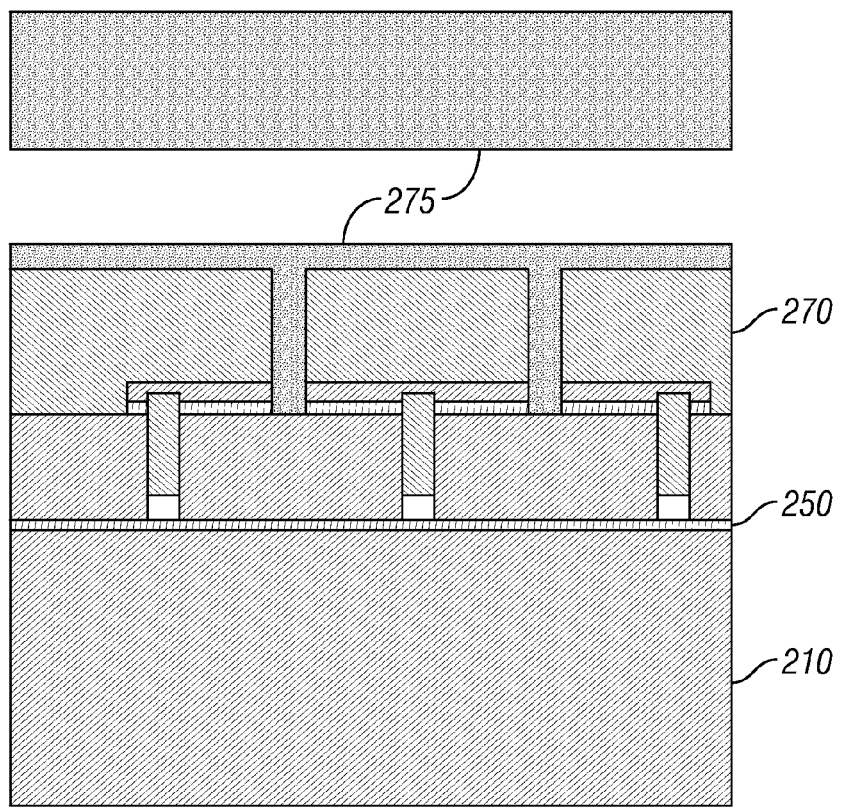

Referring now to FIG. 5E, a final capping layer 270 is deposited over the entire surface of wafer 210 to provide structural rigidity and seal the sidewalls of the nanochannel areas. Using a photolithography process, outlet microchannels 280 can be patterned and etched through capping layers 230, 270 and optionally through spacing layer 220 into silicon 210 for additional process latitude. As shown in FIG. 5F, a protective layer 275 is deposited over capping layer 270 and outlet microchannels 280.

Figure 5G:
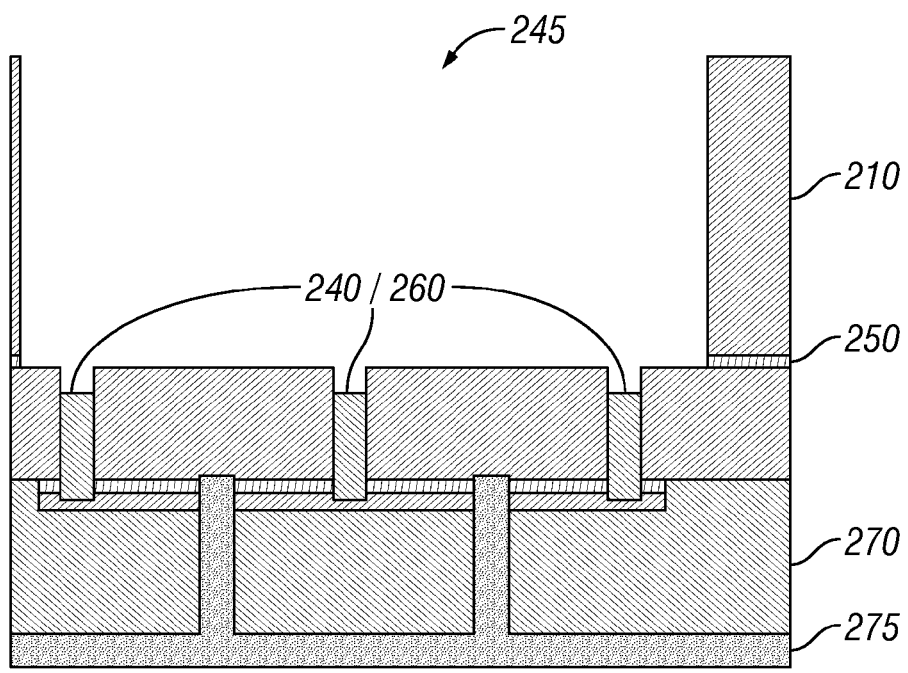
Figure 5H:
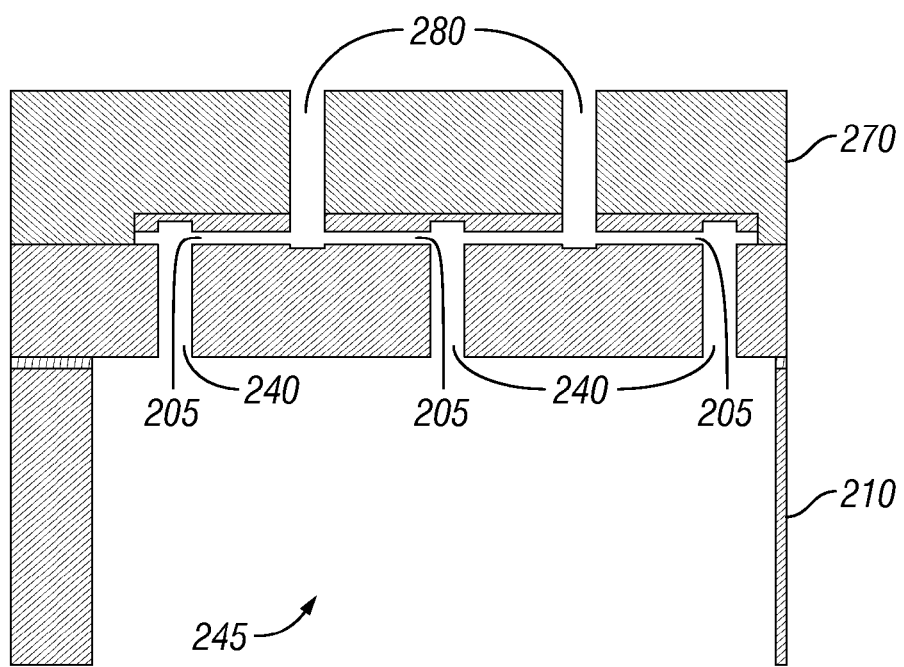

Referring now to FIG. 5G, wafer 210 can then be inverted and large openings for inlet macrochannels 245 on the back of wafer 210 can be formed by DRIE down to the buried oxide layer 250 of wafer 210. As shown in FIG. 5H, sacrificial and protective layers used during processing (e.g. spacing layer 220, fill material 260, capping layer 270, and portions of oxide layer 250) are removed by appropriate processes known in the art. As shown in FIG. 5H, when spacing layer 220 is removed, nanochannels 205 are formed. The wafers can then be diced to get individual nanochannel delivery devices.

As illustrated in this embodiment, nanochannels 205 are in direct fluid communication with inlet microchannels 240 and outlet microchannels 280. Specifically, inlet microchannels 240 and nanochannels 205 are directly connected so that a fluid exiting an inlet microchannel will immediately enter the nanochannel without flowing through an intermediate body.

As a variant of this protocol, and in analogy to protocol 2 above, a multilayered structure can be built by repeated application of the monolithic top layer process. A plurality of capping layer 230 and spacing layer 220 pairs can be deposited. The inlet microchannels can be etched through all layers down to the buried oxide and filled with fill material 260 and polished as above. The final capping layer 270 can be applied and outlet microchannels 280 etched as above.
Protocol 4: Varying the Length of Nanochannels In certain embodiments, Protocol 1 can be modified to make a nanochannel delivery device with different a nanochannel length while keep other features unchanged. An exemplary microfabrication protocol comprises the following steps.

Starting with a SOI (silicon on insulator) wafer, a hard mask layer such as silicon nitride film or LTO (low temperature oxidation) film that will protect the underneath silicon during thermal oxidation process is deposited. If silicon nitride is used, a silicon dioxide pad layer may be deposited before nitride deposition. As an alternative, the bottom substrate can also be silicon wafer instead of SOI if the etching process rates are well characterized.

Figure 6A:
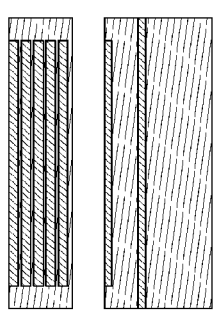
FIGS. 6A-6J are schematic views of a manufacturing process according to an exemplary embodiment.

The nanochannel areas can be patterned on the mask layer using photolithography process. (See FIG. 6(a)), and the mask materials on nanochannel areas are selectively removed but do not affect underneath silicon. A combination of dry etching, and short time wet etching may be applied for this purpose. A silicon dioxide film (with a well-controlled thickness) is deposited on the bare silicon area by thermal oxidation. The thickness of the oxidation layer defines the height of nanochannels, and the mask layer and oxide is stripped.

Figure 6B:
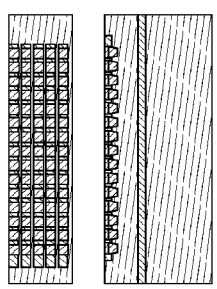

A mask layer suitable for potassium hydroxide (KOH) wet etching is deposited, such as silicon nitride. A new mask is designed to lay-out both inlet microchannels and outlet microchannels on the same layer, and the nanochannel length is defined by the spacing between adjacent inlet and outlet microchannels. The mask layer is patterned using the new mask by standard photolithography process. The mask materials on open areas are selectively removed. Then a KOH wet etching is applied to form openings with the slope wall, and the mask layer is stripped. (See FIG. 6(b)).

A mask layer suitable for deep silicon etching can be deposited. The mask layer should be able to be patterned, and have a high selectivity to silicon during deep silicon etching process. Depending on the technique for deep silicon etching, a layer of silicon oxide, photoresist, metal film, or other suitable material may be used.

Figure 6C:
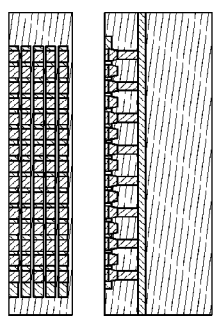

The outlet microchannels are patterned on the mask layer and the outlet micro channels are etched down to the oxide layer of the SOI wafer by a suitable technique, for example a deep RIE or ICP technique. (See FIG. 6(c)). If a silicon wafer is used, the etching depth can be determined by etching rate and time.

Figure 6D:
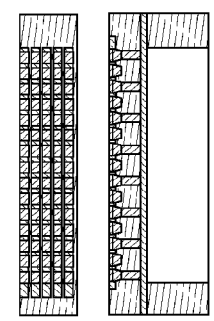
Figure 6E:
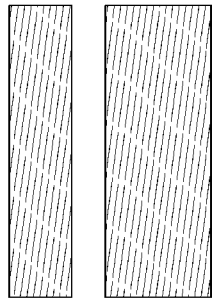
Figure 6F:
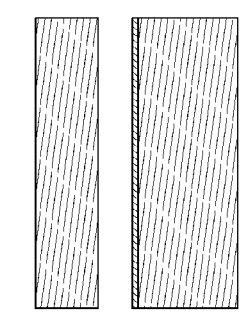
Figure 6G:
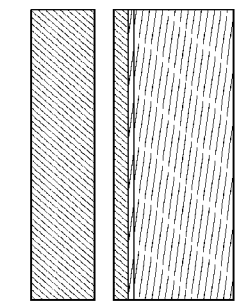
Figure 6H:
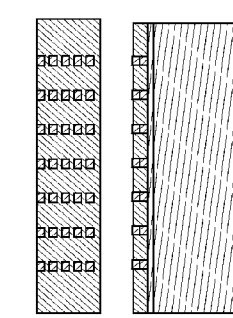
Figure 6I:
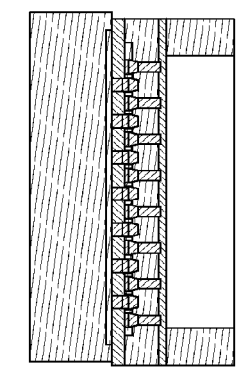
Figure 6J:
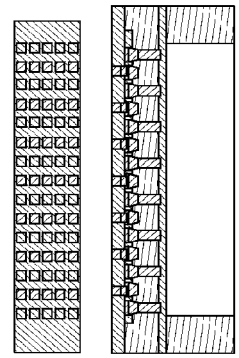

The inlet macrochannels from the back are laid out and etched to the oxide layer of the SOI wafer, and the exposed oxide areas are cleaned by HF solution. (See FIG. 6(d)). To fabricate the top cover of the nanochannel delivery devices, starting with a support wafer (e.g., silicon wafer), a sacrificial layer is deposited. (See FIG. 6(e, f)). This sacrificial layer (e.g. ITO), is selected so that it can be removed in a solution that is safe for silicon and top cover materials.

The top cover of the nanochannel delivery devices is deposited on the sacrificial layer. (See FIG. 6(g)), and the outlets are patterned on the structure. (See FIG. 6(h)). As an alternative, a lift-off technique may be applied for the cases of sputtered glass or e-beam evaporated glass. In certain embodiments, the materials may be spin-on-glass, sputtered glass, e-beam evaporated glass, ITO-glass sandwich, silicon, polymer, etc. The materials should be able to bond to silicon by certain means. For instance of glass, anodic bonding can be applied. A spin-on-glass layer may also applicable. Depending on the surface quality, a planarization process may be needed.

The structure wafer from step (6) and the top cover can be bonded together by a technique such as anodic bonding or Si—Si direct bonding or intermediate layer aided bonding. (See FIG. 6(i)). The support wafer of top cover is removed (See FIG. 6(j)), and the devices are obtained by dicing the wafer, and cleaning.

Figure 8B:
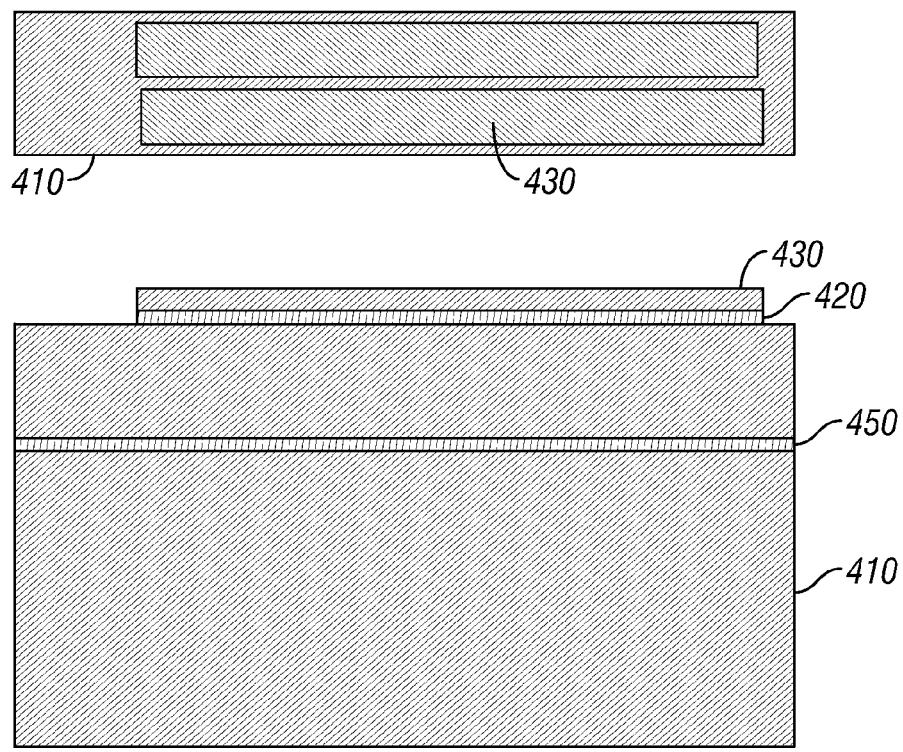

If the preferred length of nanochannel is less than 500 nm, a nanofabrication technique such as e-beam or nanoimprint may be applied. Isotropic silicon etching technique may also be applied. A schematic structure view of a short nanochannel delivery device is shown in FIG. 7. As shown in FIG. 7, inlet microchannel 340 has a portion 341 that is flared or tapered proximal to nanochannel 305. Similarly, outlet microchannel 380 has a portion 381 that is flared or tapered proximal to nanochannel 305. Nanochannel 305 is therefore shortened as a result of portions 341 and 381.
Protocol 5: Hybrid Monolithic-Bonded Capping Layer As a fifth embodiment, a nanochannel structure can be fabricated without the use of a CMP process, while utilizing bonding as a non-critical step in the capping layer fabrication. This exemplary microfabrication protocol comprises the following steps as seen in FIGS. 8A-8P.

Referring initially to FIG. 8A, starting with an SOI (silicon on insulator) substrate wafer 410, a nanochannel spacing layer 420 (with a thickness that is well-controlled, for example, ±5% over the relevant portion of SOI substrate wafer 410) is deposited. The thickness of spacing layer 420 can be used to define the height of the nanochannels. This spacing layer 420 is a sacrificial layer, and the material will be removed in a subsequent step, so the silicon surface immediately under it is the "floor" of the eventually formed nanochannels. The spacing material should have a high wet etch selectivity to all other materials in the nanochannel delivery device. As an example, a thin film of tungsten, germanium, or silicon oxide can be used for nanochannel spacing layer 420.

A capping layer 430 is deposited over nanochannel spacing layer 420. Capping layer 430 will ultimately be the "ceiling" of the nanochannels. Silicon nitride, silicon oxide, silicon carbide, or other material which has a high wet etch selectivity to the material for spacing layer 420 may be used for capping layer 430. The nanochannel areas can be patterned on spacing layer 420 and capping layer 430 using a photolithography process. As shown in FIG. 8B, spacing layer 420 and capping layer 430 on non-nanochannel areas 432 and 433 are etched to or slightly below the silicon surface of silicon wafer 410.

Figure 8C:
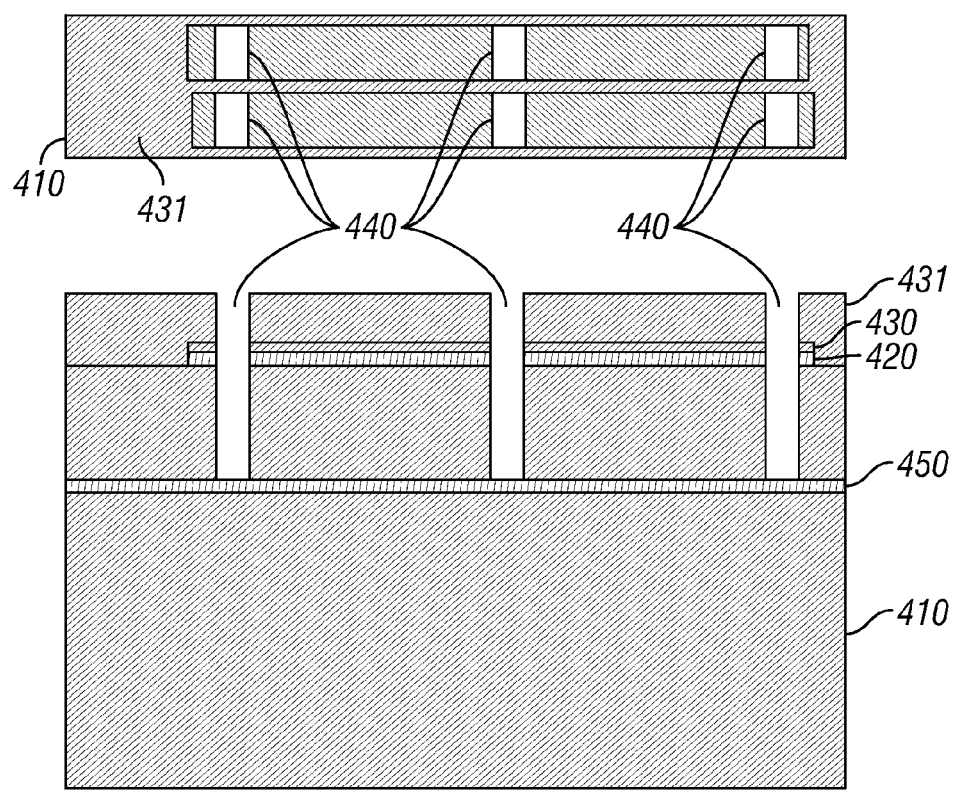

Referring now to FIG. 8C, additional capping material 431 is deposited, and optionally planarized by CMP to provide a flat surface. Inlet microchannels 440 are patterned on the mask layer (not shown) using photolithography. The DRIE process(es) etch inlet microchannels 440 through the capping layer 430 and spacing layer 420 and silicon down to a buried oxide layer 450 of SOI substrate wafer 410. The mask layer is removed and additional appropriate surface layers useful for bonding can be deposited on this surface, as needed.

Figure 8D:
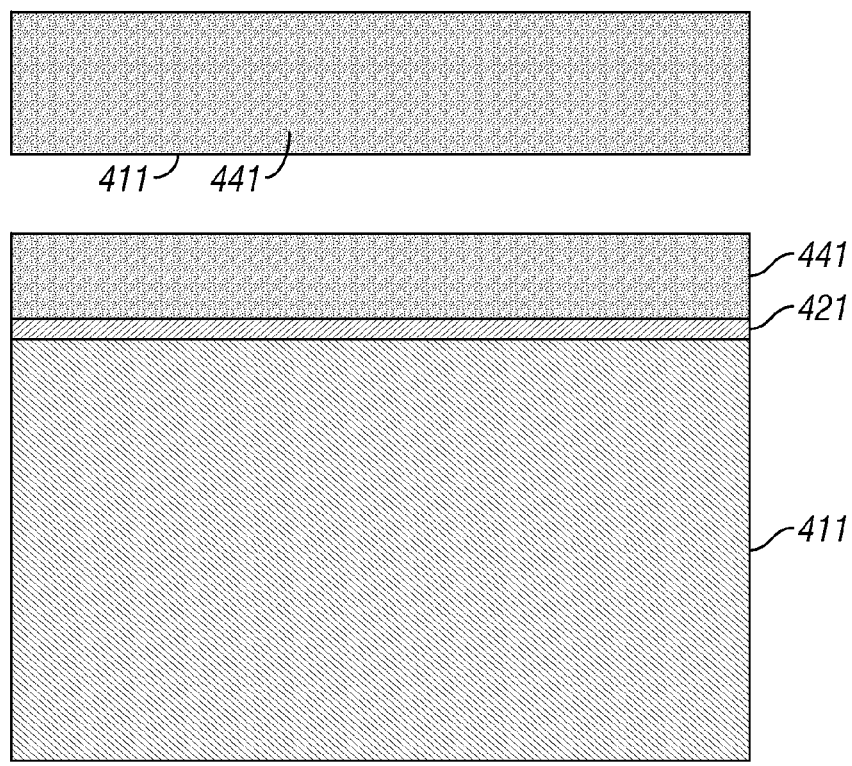

Referring now to FIG. 8D, on another silicon substrate (e.g. a capping wafer 411), a layer 421 (comprising, for example, silicon nitride or silicon oxide) can be deposited. On top of layer 421, a bonding layer 441 is deposited. The material for bonding layer 441 can be chosen so as to adhere well to the material on the surface of wafer 410 (e.g. capping material 431). The material for bonding layer 441 can also be designed so that any surface particles can be absorbed into bonding layer 441 to prevent any delamination between capping wafer 410 and substrate wafer 411 after bonding. Alternatively, a highly clean process before and during bonding can be used without this requirement. Exemplary materials for bonding layer 441 include polymeric materials, silicon oxide, and copper. Before the application of bonding layer 441, optionally, a material with a very high etch rate, "the release layer" 421, can also be applied with an additional silicon nitride or silicon oxide layer (not shown) on top of this release layer. Layer 421 can comprise a material with a high selectivity to other materials in the nanochannel delivery device.

Figure 8E:
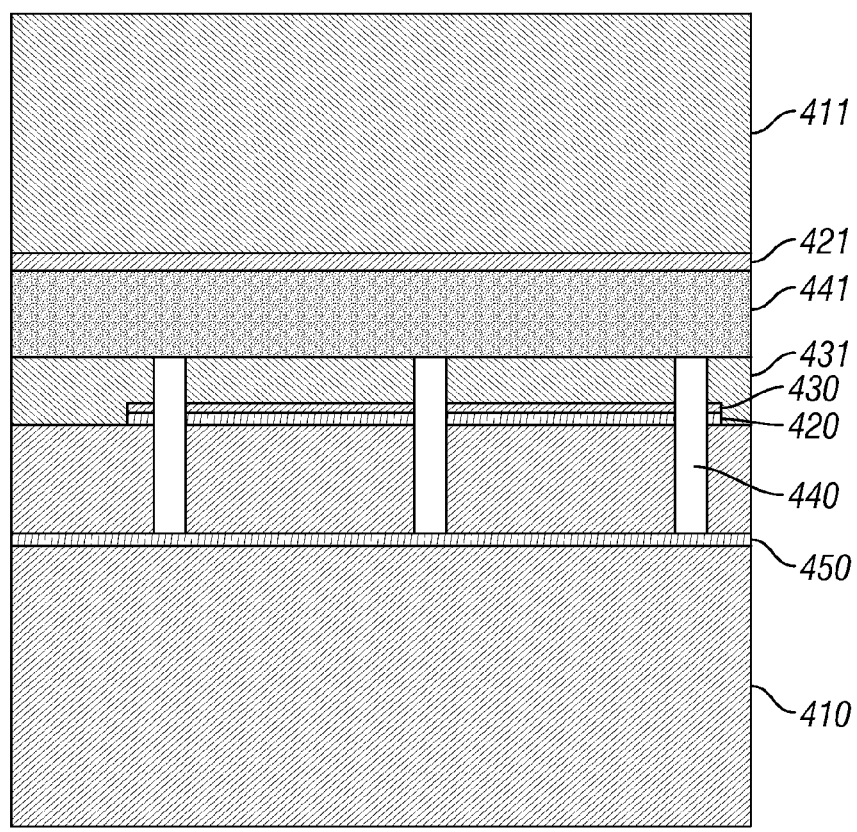

Referring now to FIG. 8E, capping wafer 411 and substrate wafer 410 are then bonded onto each other. In certain embodiments, the bonding can be polymer-silicon nitride bond, such as Benzocyclobutene (BCB)-silicon nitride, copper-copper thermocompression bond or oxide-to-oxide fusion bond, each with appropriate pre- and post-bond treatments known to those skilled in the art.

Figure 8F:
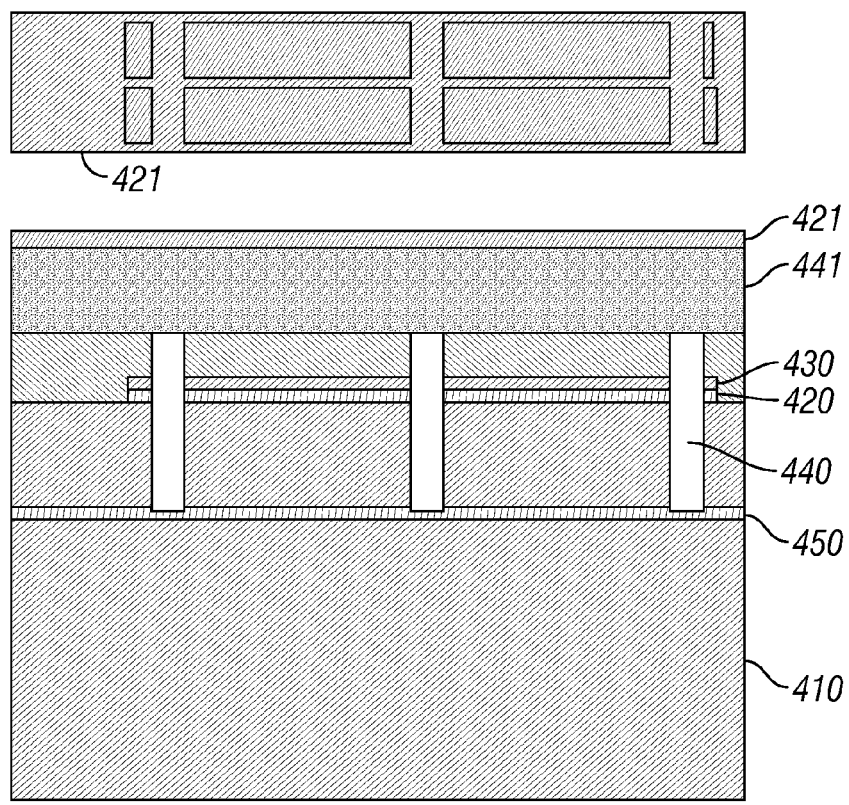

Referring now to FIG. 8F, the silicon portion of capping wafer 411 is then removed through a suitable process, e.g. mechanical thinning, a chemical etch, or a combination of both. In the case of the optionally added "release layer" 421, the release layer can be selectively removed to cause separation of the silicon capping wafer 411 from substrate wafer 410.

Figure 8G:
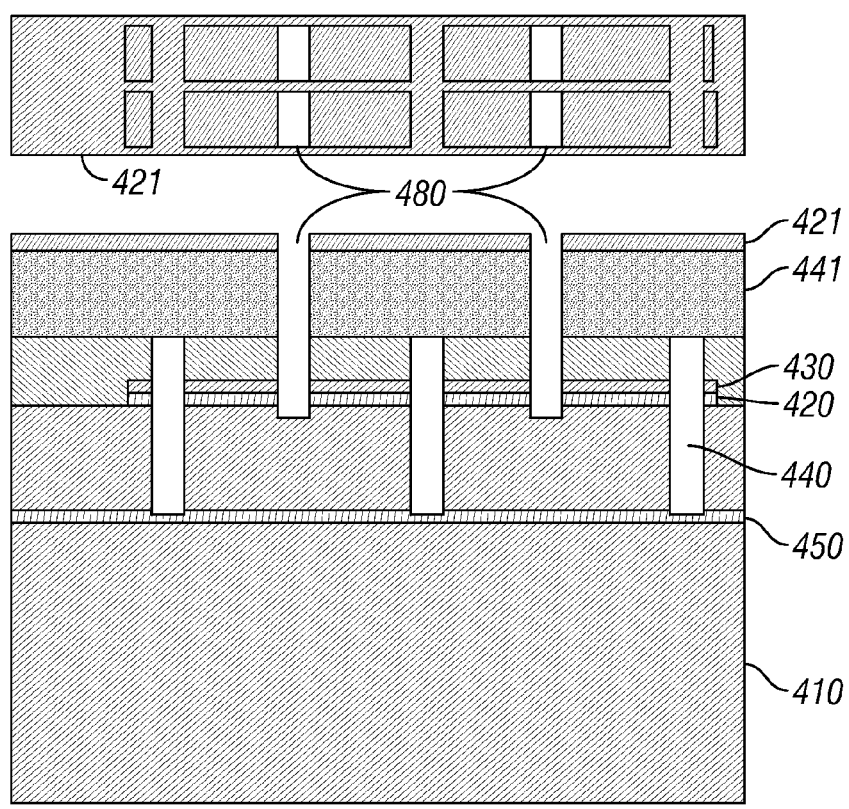

Referring now to FIG. 8G, using a photolithography process, outlet microchannels 480 can be patterned and etched through optional release layer 421, bonding layer 441, capping material 431, capping layer 430, and optionally through spacing layer 420 into the silicon for additional process latitude.

Figure 8H:
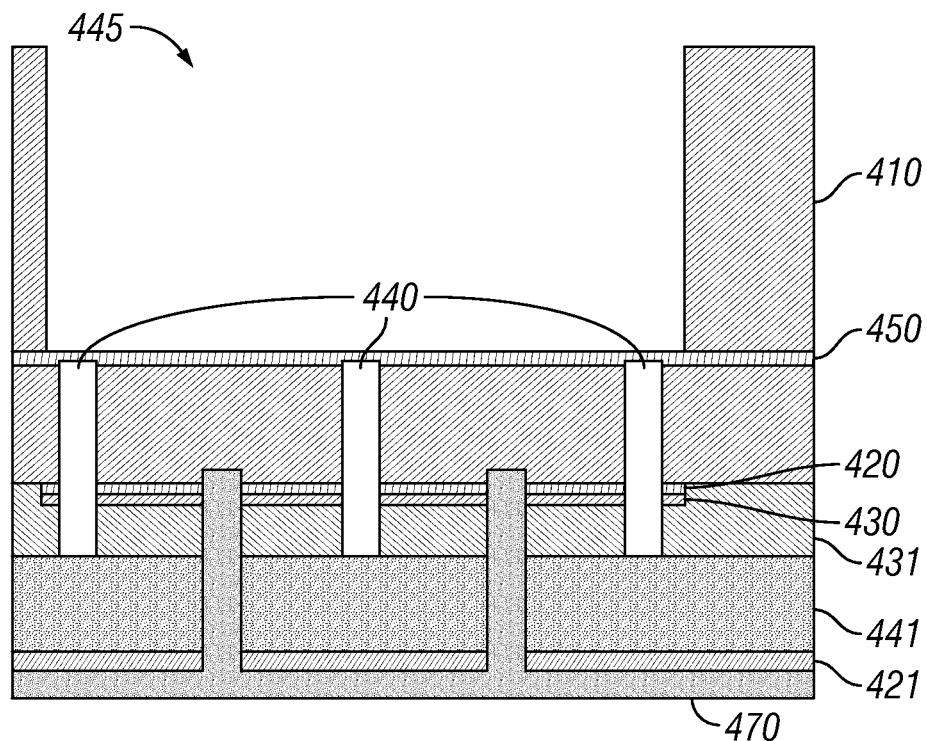

Referring now to FIG. 8H, a protective capping layer 470 is deposited over the surface of substrate wafer 410. Wafer 410 (with layer 421 and bonding layer 441 from wafer 411) is then inverted and inlet macrochannels 445 on the back of wafer 410 can be formed by DRIE down to the buried oxide layer 450 of wafer 410.

Figure 8I:
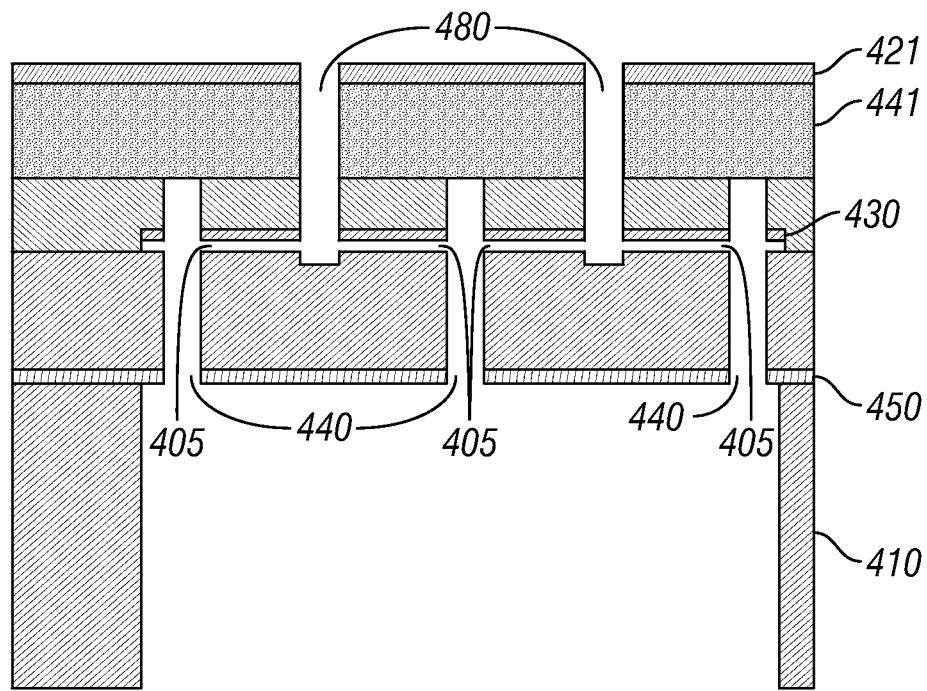

Referring now to FIG. 8I, sacrificial layers (e.g. spacing layer 420, capping layer 470, and portions of oxide layer 450) are removed by appropriate processes known in the art. As shown in FIG. 8I, when spacing layer 420 is removed, nanochannels 405 are formed. As illustrated in this embodiment, nanochannels 405 are in direct fluid communication with inlet microchannels 440 and outlet microchannels 480.

Figure 8J:
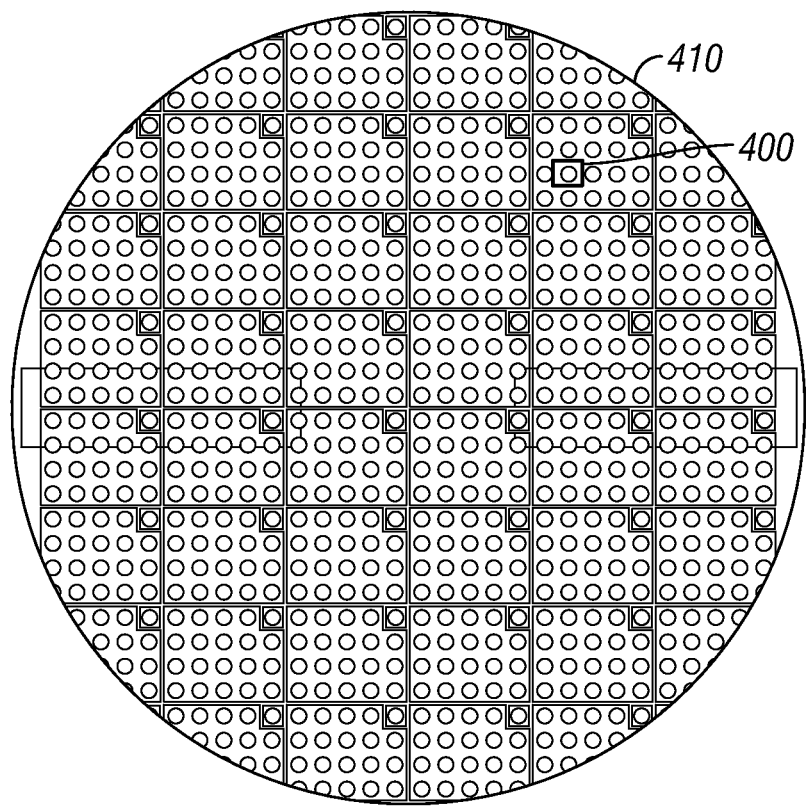
FIGS. 8J-8P are orthogonal and perspective views of exemplary embodiments during various stages of the manufacturing process.
Figure 8K:
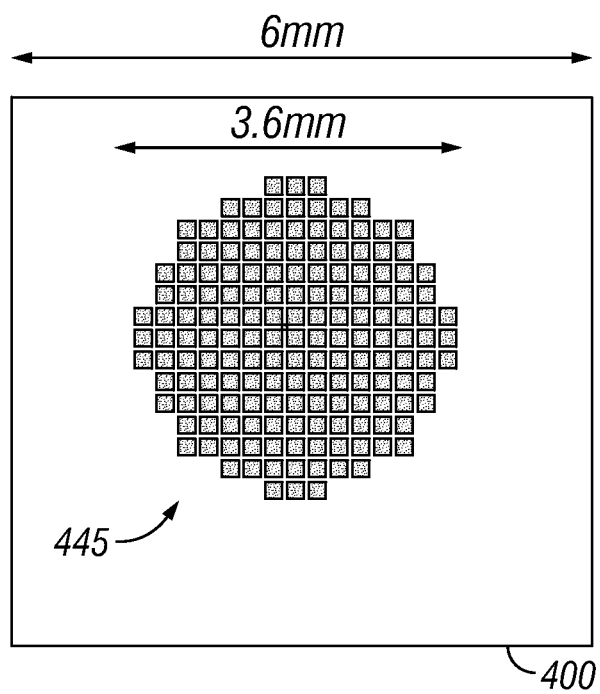

Referring now to FIG. 8J, a top view of the entire wafer 410 is illustrated. As shown in this view, wafer 410 (prior to dicing) comprises several nanochannel delivery devices 400 (only one of which is identified in the figure). Wafer 410 can be diced to separate the individual nanochannel delivery devices 400 from each other. A detailed view of an individual nanochannel delivery device 400 with exemplary dimensions is illustrated in FIG. 8K. In this view, a plurality of inlet macrochannels 445 are visible on one side of nanochannel delivery device 400. This exemplary embodiment of nanochannel delivery device 400 is approximately 6.0 mm square, and the inlet macrochannels form a generally circular shape approximately 3.6 mm in diameter. It is understood that while wafer 410 of Protocol 5 is illustrated in FIG. 8J, other protocols will also yield wafers that comprise multiple nanochannel delivery devices, and can be diced or separated into the individual devices. It is also understood that other exemplary embodiments may comprise different dimensions than those shown in FIG. 8K. In some embodiments, the wafer 410 may remain whole, effectively forming a nanochannel delivery device with dimensions similar to that of a silicon wafer, for example, approximately 500 to 750 micrometers in thickness and 100, 150, 200, 300, 450, or 675 mm in diameter.

Figure 8L:
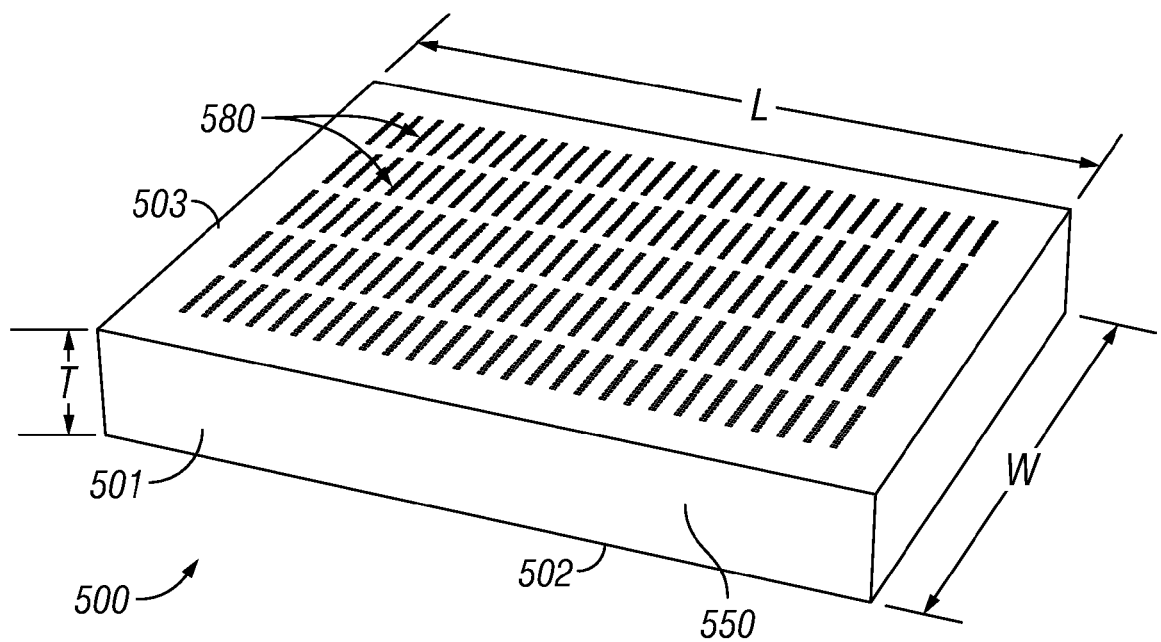
Figure 8M:
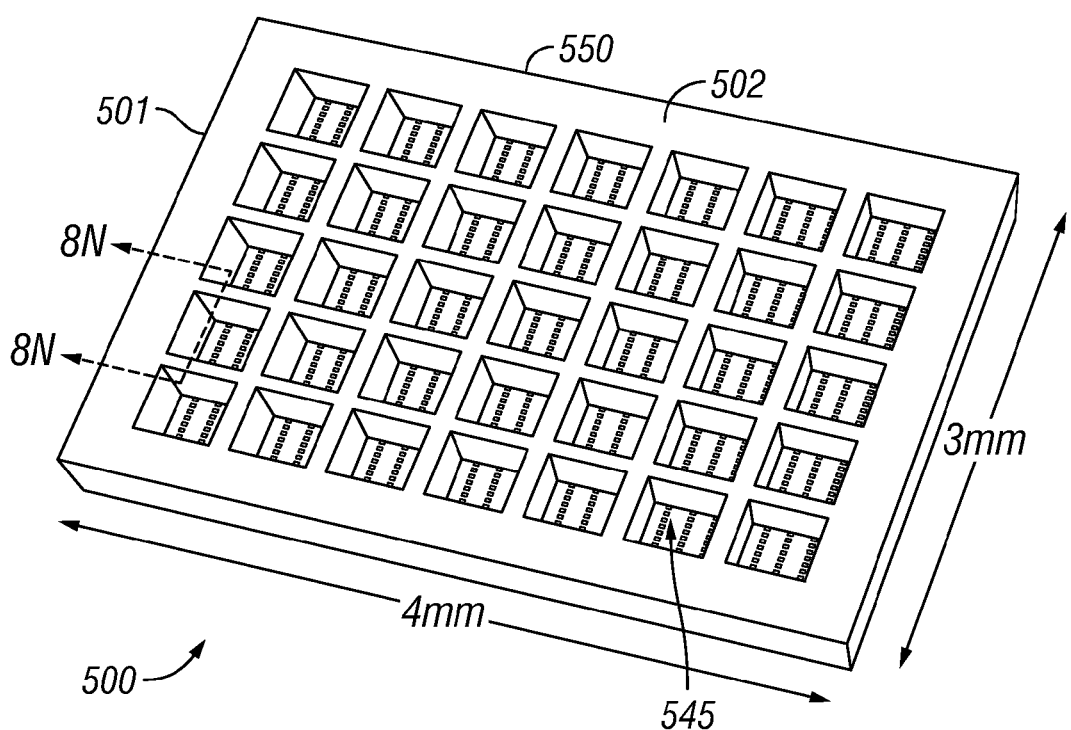
Figure 8N:
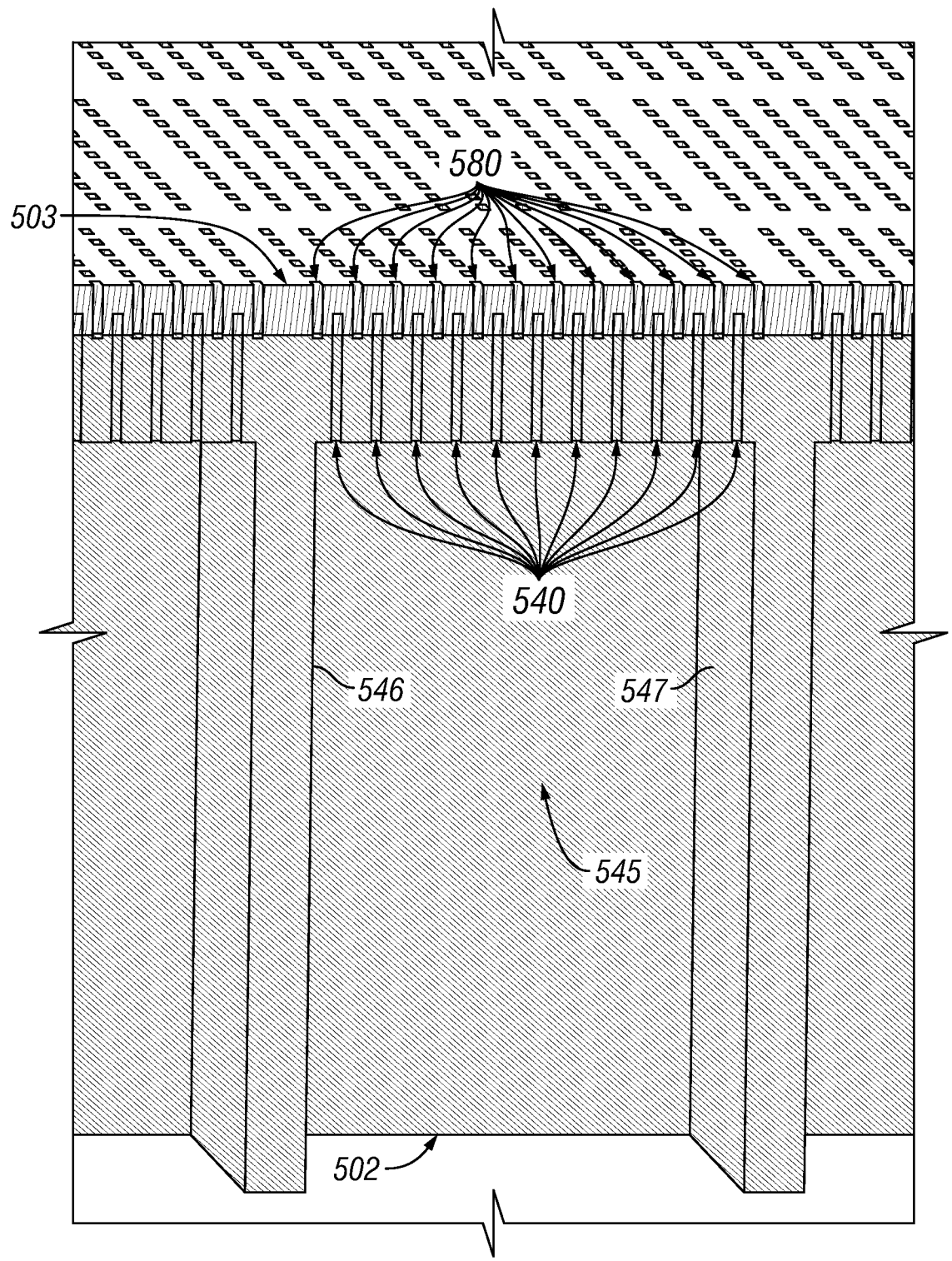
Figure 8O:
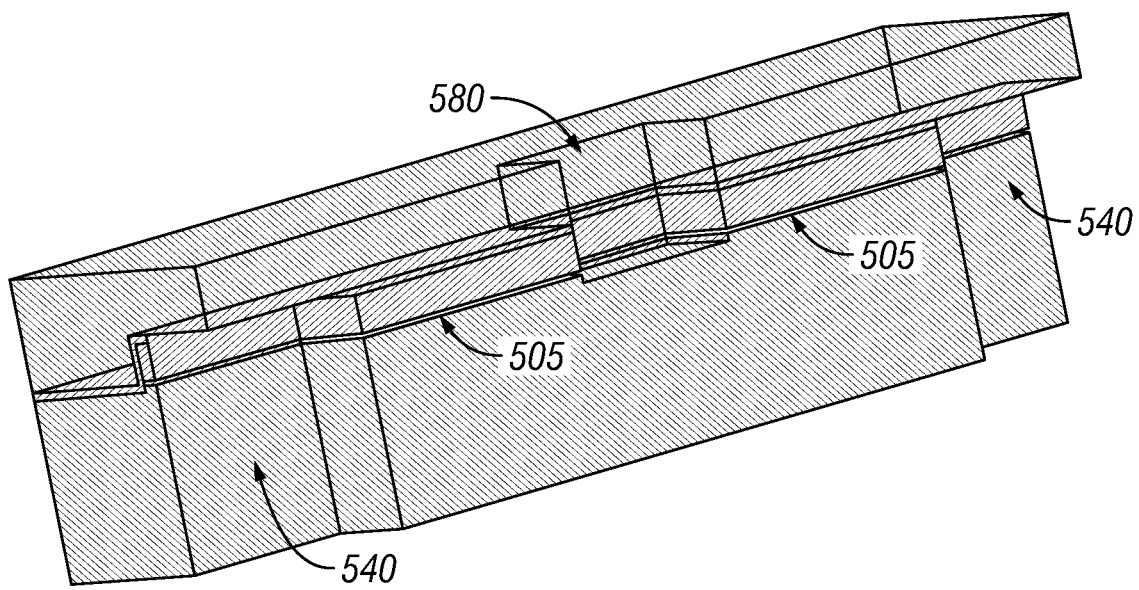
Figure 8P:
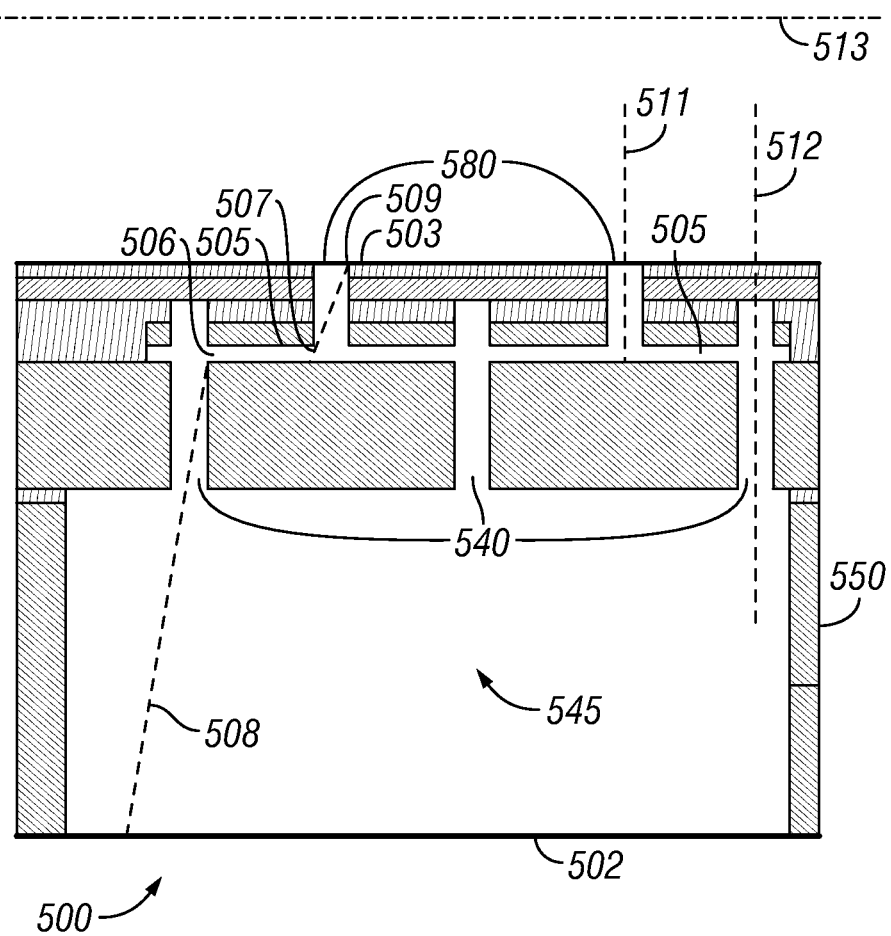

For example, referring to FIGS. 8L and 8M a nanochannel delivery device 500 is shown comprising a body 501 that is substantially planar and has a rectangular shape with a thickness "T", a length "L" that is 4 mm and a width "W" that is 3 mm. The thickness "T" may be varied, but in certain embodiments is approximately 550-700 μm, and is less than either length L or width W. Length L and width W define the primary plane of nanochannel delivery device 500. As shown in the figures, body 501 has an inlet surface 502 on one side and an outlet surface 503 on the opposite side. Inlet surface 502 and outlet surface 503 are generally parallel to each other and parallel to the primary plane of nanochannel delivery device 500. Visible in FIG. 8M are a plurality of inlet macrochannels 545 (only one of which is identified in the figure). FIG. 8N provides a perspective view of a partial cross-section of nanochannel delivery device 500 taken along line 8N-8N in FIG. 8M. The portion illustrated in FIG. 8N comprises a single inlet macrochannel 545 and multiple inlet microchannels 540 and outlet microchannels 580. As shown in FIGS. 8L-8N, inlet microchannels 540 and outlet microchannels 580 are formed so that individual inlet and outlet microchannels are perpendicular to the primary plane of nanochannel delivery device 500 (e.g., the length of the microchannels is measured along a line that is perpendicular to the primary plane of the device). In addition, the plurality of inlet microchannels 540 and outlet microchannels 580 form overlapping arrays so that individual inlet microchannels 580 are distributed between individual outlet microchannels 580, and vice versa. Referring now to FIG. 8 As shown in the detailed view of FIG. 8O, each nanochannel 505 is in direct fluid communication with an inlet microchannel 540 and an outlet microchannel 580.

Referring now to FIG. 8P, a detailed section view of a section of nanochannel delivery device 500 is illustrated. In this view, three inlet nanochannels 540 are visible, along with a pair of outlet microchannels 580 and a pair of nanochannels 505. As shown, nanochannel 505 comprises an inlet end 506 and an outlet end 507. In this embodiment, a first linear axis 508 extends between inlet end 506 and inlet surface 502. Also visible in FIG. 8P, a second linear axis 509 extends between outlet end 507 and outlet surface 503.

Also shown in FIG. 8P, inlet microchannel 540 comprises a primary axis 512 and outlet microchannel 580 comprises a primary axis 511. As shown in this embodiment, primary axis 511 and primary axis 512 are perpendicular to a plane 513 that is parallel to a substantially planar body 550 of nanochannel delivery device 500. In FIG. 8P, only a portion of substantially planar body 550 is shown. A complete view of substantially planar body 550 is visible in FIGS. 8L and 8M.

Figure 9:
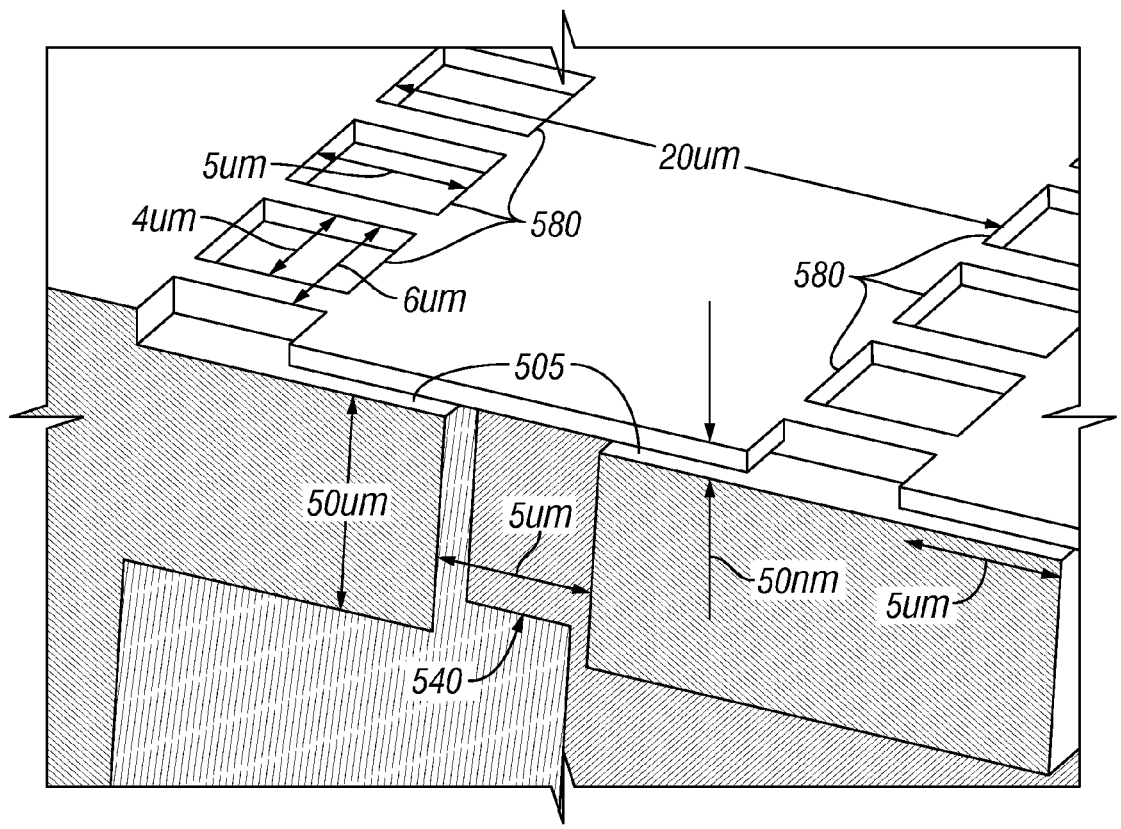
FIG. 9 is a perspective view of a nanochannel delivery device according to an exemplary embodiment.

Referring now to FIG. 9, specific dimensions for an exemplary embodiment of a nanochannel delivery device manufactured according to the above protocol are provided. It is understood that these dimensions are illustrative of the specific embodiment shown, and that other embodiments may incorporate different dimensions.

Figure 10:
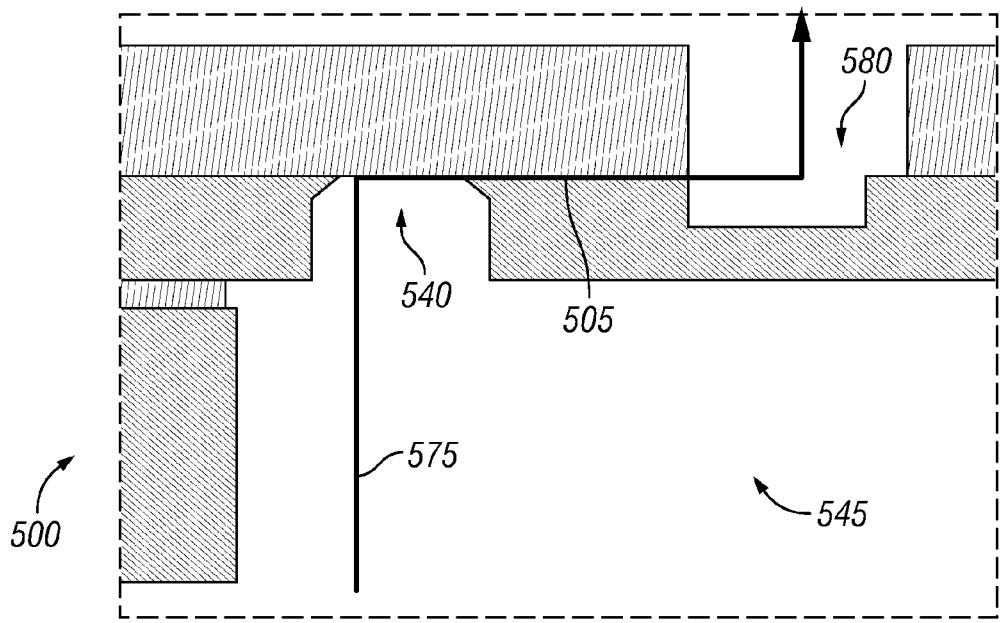
FIG. 10 is a cross-sectional side view of a schematic of an exemplary embodiment of a nanochannel delivery device.

Referring now to FIG. 10, a partial cross-section of nanochannel delivery device 500 illustrates the diffusion path 575 for a molecule passing through nanochannel delivery device 500. It is understood that nanochannel delivery device 500 may be oriented in any direction during use. As shown in FIG. 10, flow path 105 requires a maximum of two changes in direction between the point where the molecule enters nanochannel delivery device 500 and the point at which the molecule exits nanochannel delivery device 500. For example, the molecule enters nanochannel delivery device 500 and is initially located within inlet macrochannel 545. The molecule then enters inlet microchannel 540. In the embodiment shown, flow path 575 turns at a 90 degree angle to the right as the molecule enters the nanochannel 505 that is in direct fluid communication with inlet microchannel 540. After the molecule exits the nanochannel 505, the flow path turns again (this time, a 90 degree turn to the left) as it enters the outlet microchannel 580, which is also in direct fluid communication with the nanochannel 505. Therefore, flow path 575 requires a maximum of two changes in direction as the molecule diffuses through nanochannel delivery device 500. While a molecule may undergo more than two changes in direction as it passes through nanochannel delivery device 500, it is only required to make two changes in direction.

Example

Protocol 1: Bonded Capping Layer

The following example is provided as an illustration of one non-limiting embodiment of a method of manufacturing a nanochannel delivery device according to Protocol 1 (described above). This example is provided for illustration purposes only and is not intended to limit the scope of the invention described herein.

Processing begins with a double polished 4" SOI wafer (available from Silicon Quest). The wafer comprises a device layer that is 30 um thick, <100> orientation P-type, Boron doped, and a 1-10 Ohm-cm surface resistivity, a buried oxide layer that is 0.4 um thick and a handle layer that is 500 um thick, P-type, Boron doped, and 1-10 Ohm-cm surface resistivity. The wafer was cleaned in a fresh Piranha solution (3:1 98% sulfuric acid: 30% hydrogen peroxide, over 100 C) for 10 min, and spun dried. A 50 nm pad oxide layer was then thermally grown on the surface. Then a 100 nm low-stress nitride was deposited on the pad oxide layer by low-pressure chemical vapor deposition (LPCVD). The 5 um wide nanochannel patterns were transferred from the photo mask onto the silicon nitride layer by standard photolithography using an EVG 620 aligner. The exposed nitride area was removed by CF4 RIE.

After the photoresist was stripped, the pad oxide was cleaned by dipping in 1:10 HF water solution. Then the wafer was placed in a thermal oxide furnace to grow sacrificial oxide. The thickness of this sacrificial oxide determined the height of nanochannels, i.e. height of nanochannel=0.46*Thickness of Oxide. In this example, a 39 nm oxide was grown for 18 nm nanochannels. Then the nitride and oxide were removed in dilute HF solution. A 3 um thick low temperature oxide (LTO) layer was then deposited on the surface by LPCVD. Then the backside of wafer was protected by 3 um spun-on Futurrex negative photoresist. The LTO on front side was removed in a buffered oxide etch (BOE) solution, and the wafer was cleaned in piranha solution.

A 500 nm LTO film was deposited on the wafer using LPCVD. The 5 um×5 um inlet microchannel patterns were transferred to the LTO film on the device side of wafer using standard lithography on an EVG 620 aligner, and LTO were etched using CF4 RIE. Then the 200 um×200 um inlet macrochannel patterns were transferred onto the backside of the wafer, and RIE was done.

Figure 11:
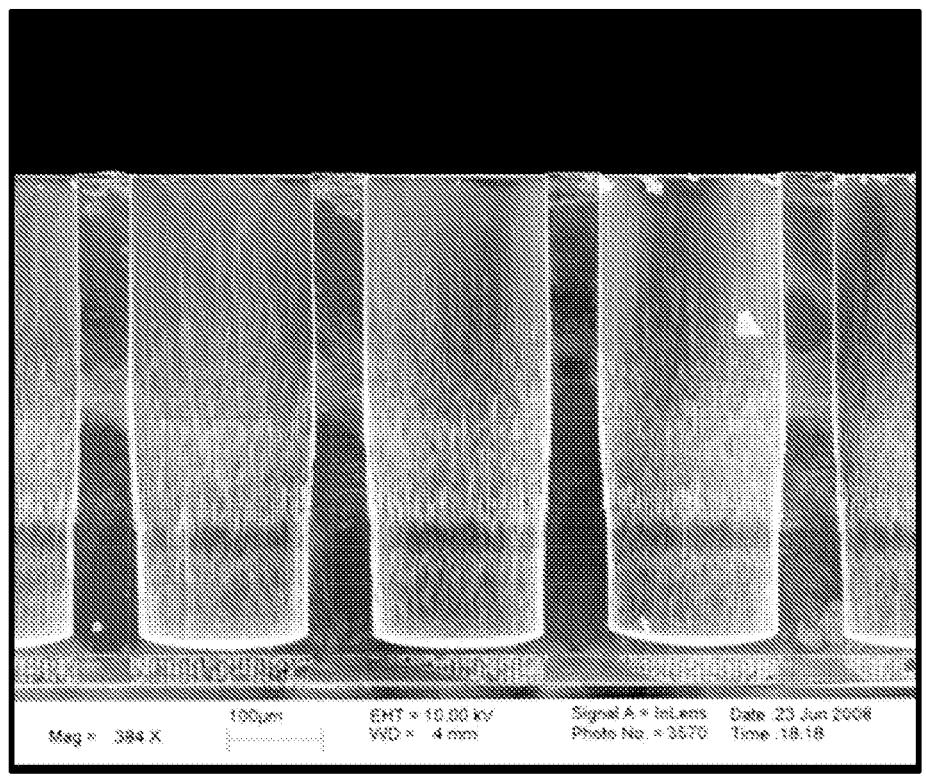
FIG. 11 is a scanning electron microscope image of a portion of a nanochannel delivery device according to an exemplary embodiment.

After cleaning out the photoresist, deep silicon etching of inlet microchannels was done using an Oerlikon DSE etcher. The etching was stopped on the buried oxide layer. The wafer was flipped over, and attached onto a handle wafer using thermal grease (AI Technology). The 190 um×190 um inlet macrochannels were then etched on the Oerlikon DSE etcher, and stopped on the oxide layer. FIG. 11 shows a SEM image of deep etched 190 um openings. The wafer was detached from the handle wafer, and cleaned. The wafer was dipped in BOE for 5 min to open the buried oxide layer, and spun dried. Then mask LTO films on both sides of wafer were removed in HF water solution.

Figure 12:
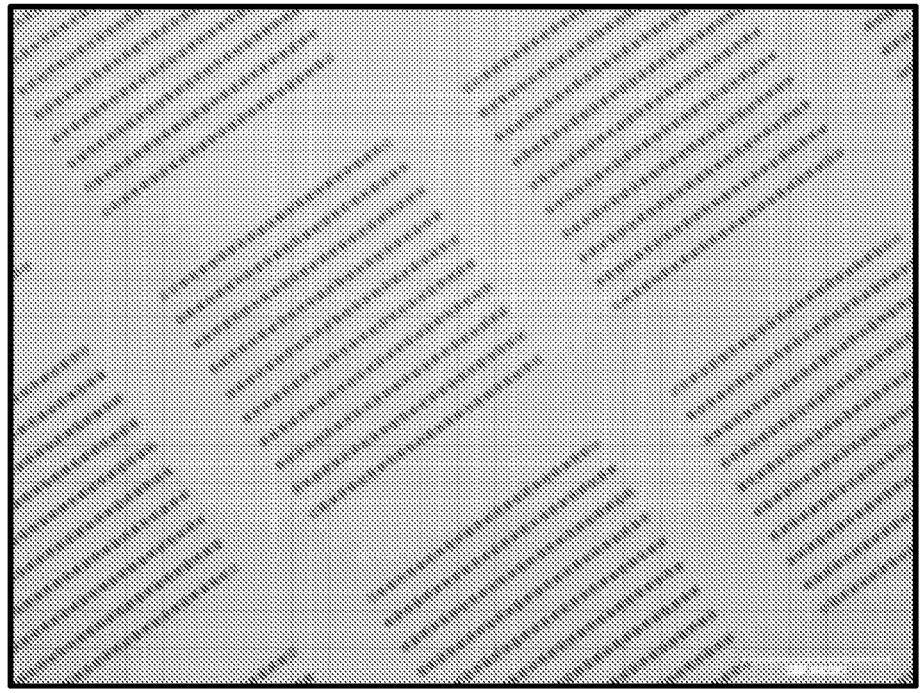
FIG. 12 is an optical image of a bonded wafer of a nanochannel delivery device according to an exemplary embodiment.

A 500 um thick double side polished Pyrex 7740 glass wafer was bonded onto the silicon substrate as a nanochannel cap by anodic bonding using an EVG 520 bonder. The anodic binding was performed at 800 volts, and 325° C. for 10 min. FIG. 12 shows an optical image of the bonded wafer. The bonded wafer pair was adhered on a wafer holder using wax, and backlapping was applied to thin the glass down to 30 um, and then CMP polished to a final thickness of 5-10 um (by Valley Design Corp).

Figure 13:
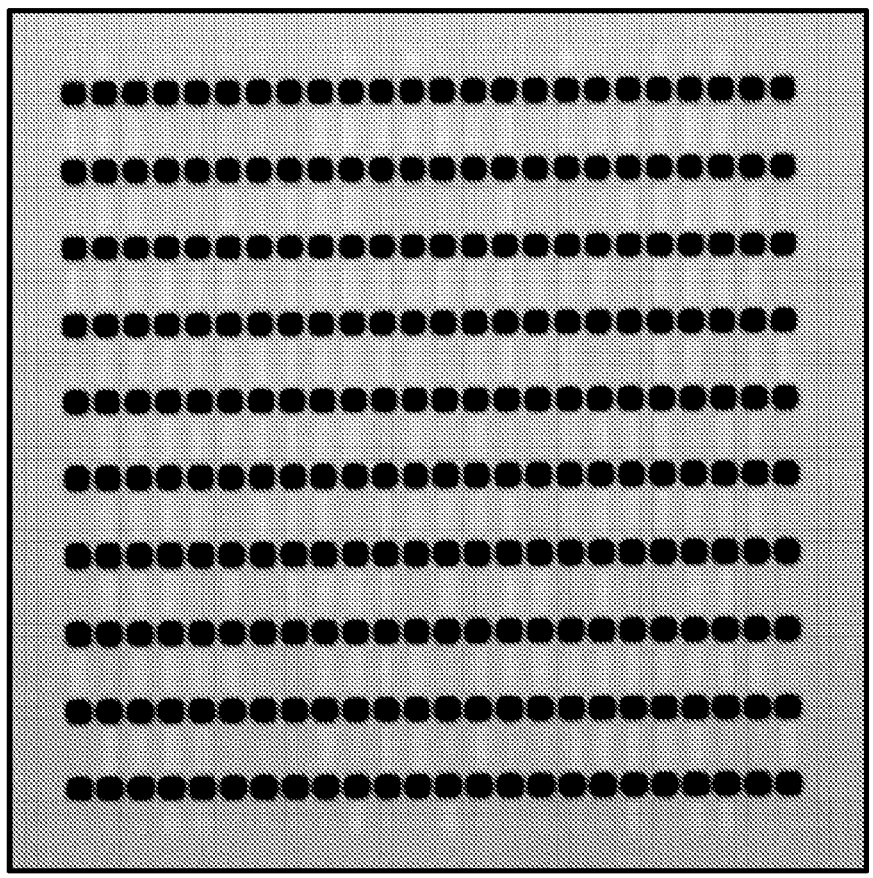
FIG. 13 is an optical image of a front surface of a nanochannel delivery device according to an exemplary embodiment after polishing.

FIG. 13 shows an optical image of the front surface after polishing. The contrast indicates that nanochannels are open. The 5 um×5 um outlet microchannels were formed by CF4/Ar RIE using Ni film as mask layer. To do so, a copper seed layer was firstly deposited on the glass surface. The 5 um×5 um outlet microchannel patterns were transferred to the copper film using standard lithography on an EVG 620 aligner, and were wet etched. Then Ni was electroplated onto the patterned copper film. The CF4/Ar RIE was used to etch the inlet microchannels into the glass film to reach the silicon surface. After stripping the mask layer, the wafer was cleaned, and diced using DAD321 Dicing Saw (Disco). The fabricated devices are 6 mm×6 mm overall dimension. There are 161 in total 190 um×190 um openings arranged in a 3.6 mm diameter circle. Each such opening is connected to 501 in total 5 um×5 um inlet channels, and the inlet channels are connected to nanochannel and outlet channels.

Example

Protocol 3: Monolithically Fabricated Capping Layer

The following example is provided as an illustration of one non-limiting embodiment of a method of manufacturing a nanochannel delivery device according to Protocol 3 (described above). This example is provided for illustration purposes only and is not intended to limit the scope of the invention described herein.

Processing begins with a double-side polished Silicon On Insulator (SOI) wafer using a 690 um thick base wafer with a top silicon layer thickness of 30 um and a buried oxide thickness of 2 um. This wafer is cleaned with a piranha solution (3:1 98% Sulfuric acid:30% Hydrogen peroxide, over 100 C) to remove any organic and metal contamination. A smooth (typically <5 A rms), uniform (typically <2% non-uniformity,) tungsten metal layer is sputtered on this wafer, using a physical vapor deposition (PVD) process at a temperature of 100 C. The thickness of this tungsten layer is selected to be the height of the nanochannel layer, for example 5 nm.

The nanochannel space layer is then covered by a plasma enhanced chemical vapor deposition (PECVD) silicon nitride ("SiN1") with low stress (380 C, appropriate stoichiometry), with a target thickness of 500 nm and a non-uniformity of less than 2%. Positive resist is then spun on, with a thickness of 2 um. The inlet microchannels are exposed in this resist, with the sizes varying from 1 um to over 5 um, as needed. Using this resist, the applied silicon nitride is etched through, along with tungsten, using a conventional C4F8 etch chemistry with appropriate plasma powers, and other reactive and inert gases.

Figure 14:
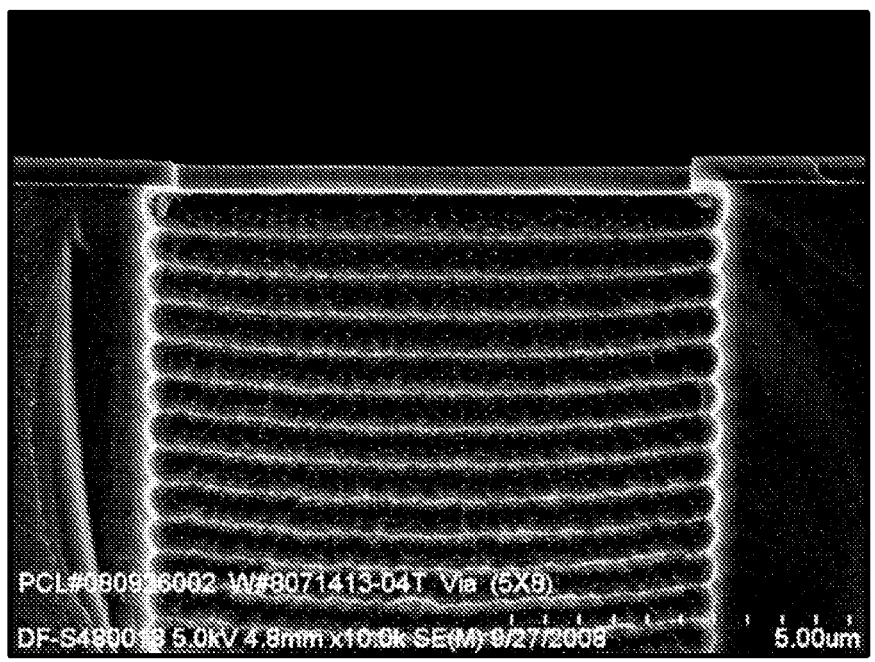
FIG. 14 is a scanning electron microscope image of a portion of a nanochannel delivery device according to an exemplary embodiment.

The etch in this process is timed to be deep enough that it goes through the tungsten layer also, which takes a few minutes. Another etch is performed, still using the resist as the mask, to etch a deep via in the silicon that is deep enough to go into the buried oxide. A 5 dep/5 etch per cycle Bosch etch is used in this step since the etch automatically terminates at, and is highly selective to, the buried oxide. A small overetch of 10-20% of the most critical structure is provided to compensate for the non-uniformity of the process. The remaining resist is then removed using an oxygen plasma and the wafers are additionally cleaned of all polymer residues using an appropriate wet chemistry FIG. 14 presents an example of a device at this stage of process.

Figure 15:
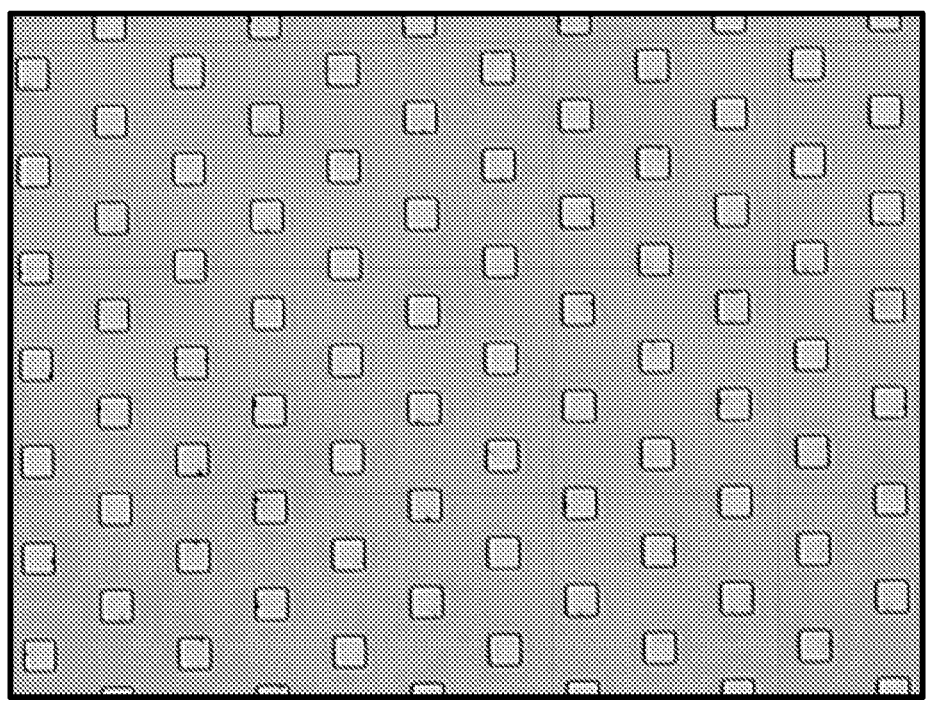
FIG. 15 is an optical image of a portion of a nanochannel delivery device according to an exemplary embodiment after polishing.

The next module consists of filling or capping these inlet microchannels. This can be accomplished by plugging the inlets with copper. A TiN barrier layer is deposited by sputter, with a thickness of 300 A. A copper seed layer, with a nominal thickness of about 4000 A is deposited through a PVD sputter process. A low current (2 A, 10-15 minutes) electroplating process is used to fill or plug the inlet microchannels. The excess copper overburden is then polished away using a pad/slurry combination, under moderate pressure/speed (2-4 psi, 30-90 rpm) process. In this same process, the TiN in the non-microchannel area (field) is also completely removed. Finally, the inlet microchannel process is hardened with a short bake anneal at 150-250 C, for about 30 minutes, and the surface is cleaned. FIG. 15 presents a top view of the device after filling with copper.

A thin silicon nitride ("SiN2") layer of about 50 nm is deposited by PECVD to cap the copper. The nanochannel lines are then exposed in resist (1.3 um) using photolithography and the silicon nitride (SiN1 as well as SiN2) layers are etched, along with the tungsten nanochannel material, with the etch proceeding a few tens of nanometers into the silicon.

Figure 16:
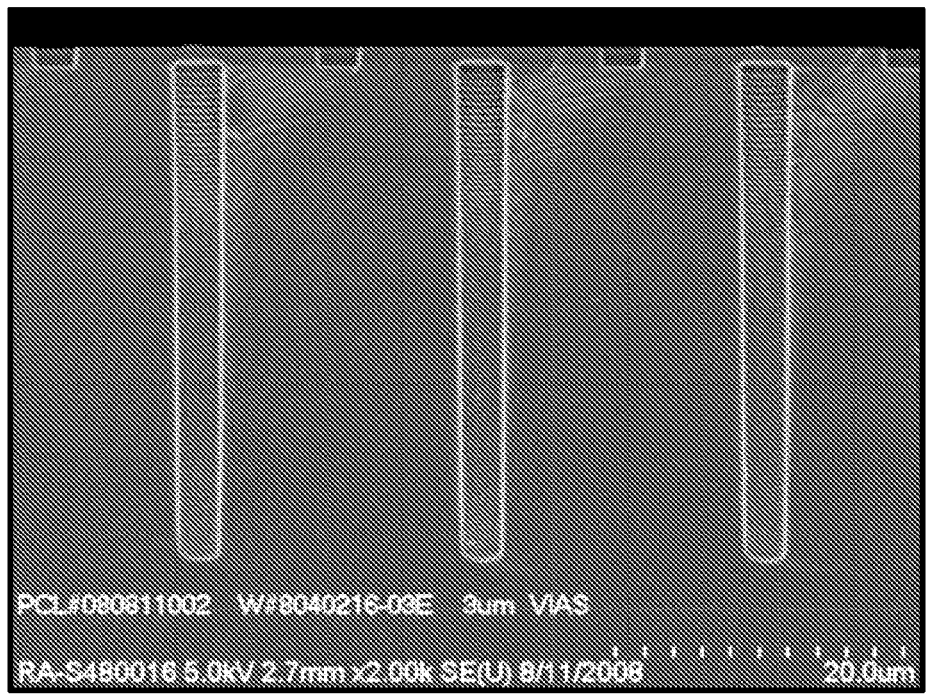
FIG. 16 is scanning electron microscope image of a portion of a nanochannel delivery device according to an exemplary embodiment.

A thicker, tensile silicon nitride ("SiN3") is then deposited, of a thickness of about 1-1.5 um. The tensile stress of this layer is chosen so as to make the overall dielectric stack slightly tensile by about 20 MPa. The outlet microchannels are then exposed on a resist layer (of nominal thickness 2 um) and a further etch of all silicon nitride layers (SiN1, SiN2, SiN3) along with the W nanochannel layer are etched so that the bottom of the outlet microchannels end in the device silicon. The resist is stripped after this stage. FIG. 16 presents a cross-section of a device at this stage of processing.

An appropriate protection layer is applied to the surface—Ti/TiN (250/300A), Tungsten (5000 A) followed by Phospho silicate Glass (PSG) of thickness of 1 um, which can be used as both an HF protectant as well as a surface protectant. The wafer is then turned upside down and a thick resist (10 um) is spun on. Using the front side alignment marks, macrochannels are exposed on the backside. The macrochannels are etched all the way through the wafer (about 700 um) using a Bosch DRIE process. This process lands on the buried oxide, which forms an effective etch stop. FIG. 17 presents a cross-section of a test device at this stage of processing. This buried oxide is then removed by a plasma etch.

A series of wet etches are done to remove all the sacrificial materials. A short buffered HF etch, for about 5 minutes, is done to remove any residual oxide (of the buried oxide), as well as to remove the PSG layer. The wafers are then wet-etched in an SC-1 solution (hot Ammonium hydroxide—hydrogen peroxide mixture) for about 10 minutes to remove the TiN barrier at the top surface as well as at the bottom of the inlet microchannels. The wafers are subjected to a piranha etch for about 20 minutes to remove the copper in the inlet microchannels. This is followed by another SC-1 etch to remove all the TiN from the sidewalls of the inlet microchannels. Finally, the Tungsten is removed from the nanochannels by placing the wafers in wafer hydrogen peroxide for 2 hours, followed by a rinse with DI water. The wafers are then cleaned with Iso-Propyl Alcohol (IPA) to displace the water with IPA, and the wafers are allowed to dry.

Material Selection

Regardless of the protocol used to manufacture the nanochannel delivery device, the materials used during the manufacturing process should be selected to successfully remove sacrificial materials while leaving the non-sacrificial materials. As shown in FIG. 18, the selection of a nanochannel "placeholder" (e.g., the sacrificial material used to fill the space of the nanochannel) and nanochannel "ceiling" and "floor" materials (e.g., the substrate and capping layers) should be coordinated with the selection of a solvent or etchant. Examples of suitable solvents and etchants that can be used to remove sacrificial materials while leaving the substrate and capping layers are shown in FIG. 18. It is understood that other combinations of materials may be utilized as well.

Post Wafer Processing

During post wafer processing, each wafer is attached to a tape-ring with an adhesive tape. A UV release tape is preferred since it has better adhesion. Since both surfaces of the wafer have critical device structures, UV tape is attached to both top and bottom surfaces. The wafers are then diced into individual die and cleaned. The tapeframe is then exposed to a UV light source to decrease the adhesion of the tape to the surface. The dice are individually picked and placed into a bare-die holder using an automated pick and place sorter tool. The tape on the top surface of the die is subsequently peeled off manually. The dice are then individually placed in a final clean container and cleaned with acetone with a final rinse of IPA to promote channel drying. A die is attached by epoxy or other fixing method to a capsule mating surface.

Capsule Configurations

Figure 19:
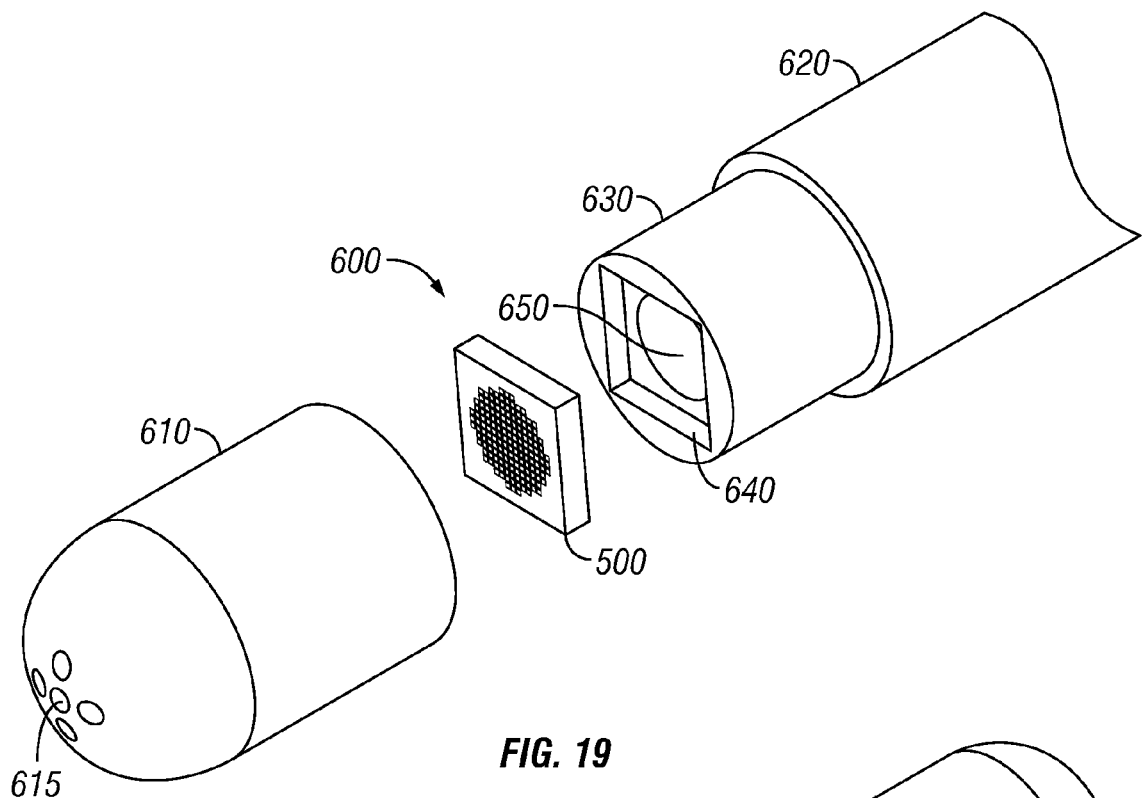
FIG. 19 is an exploded perspective view of a capsule and a nanochannel delivery device according to an exemplary embodiment.
Figure 20:
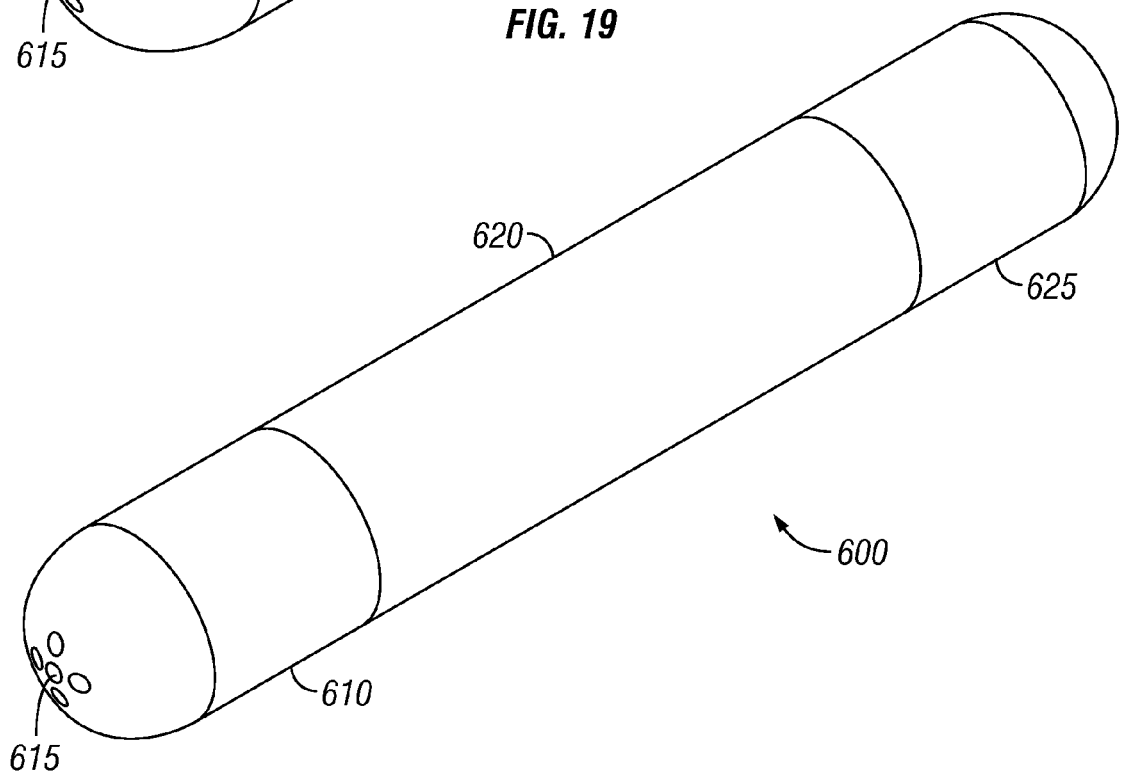
FIG. 20 is an assembled perspective view of the embodiment of FIG. 19.

Referring now to FIGS. 19 and 20, nanochannel delivery device 500 may form part of a larger assembly, e.g., a capsule 600 that may be used to administer drugs or other therapeutic agents to a patient. FIG. 19 shows a detailed view of one end of capsule 600 in an exploded view, while FIG. 20 illustrates an assembled view of capsule 600. It is understood that in other embodiments, nanochannel delivery device 500 may be used in other applications where it is desired to precisely control the diffusion or passage of small amounts of any substance.

In the embodiment shown in FIGS. 19 and 20, capsule 600 comprises a generally cylindrical body 620 having an end portion 630 configured to receive a first cap 610 and a second cap 625. In this embodiment, nanochannel delivery device 500 is installed in a plane that is perpendicular to the primary axis of capsule 600 (e.g., an axis that is parallel to the length of cylindrical body 620 and concentric with cylindrical body 620). End portion 630 also comprises a recessed portion 640 configured to receive nanochannel delivery device 500. In certain embodiments, a glue or other boding agent may be used to secure nanochannel delivery device 500 in recessed portion 640. When assembled, nanochannel delivery device 500 can be inserted into recessed portion 640, and first cap 610 may be fitted onto end portion 630.

During use, drugs (or any other substance administered via capsule 600) can pass from cylindrical body 620 to nanochannel delivery device via an inner volume 650 contained within cylindrical body 620. After diffusing through nanochannel delivery device 500 and into first cap 610, the administered substances can exit cap 610 via exit ports 615. In exemplary embodiments, the dimensions of exit ports 615 (and other aspects of capsule 610, such as inner volume 650 and cap 610) are large enough so that these features do not restrict the diffusion of the administered substance from capsule 600. As a result, the diffusion of the administered substance can be more precisely controlled by selecting the dimensions of nanochannel delivery device 500, particularly the dimensions of nanochannels 505. Cap 610 may also provide dimensional rigidity and protect nanochannel delivery device 500 from mechanical damage and the incursion of biological tissue structures after implantation.

In certain embodiments, inner volume 650 is configured to minimize capture points for air bubbles. For example, inner volume 650 may comprise radiused corners and surfaces that are not angled in a manner (when capsule 600 is installed) which could trap air bubbles.

Figure 21:
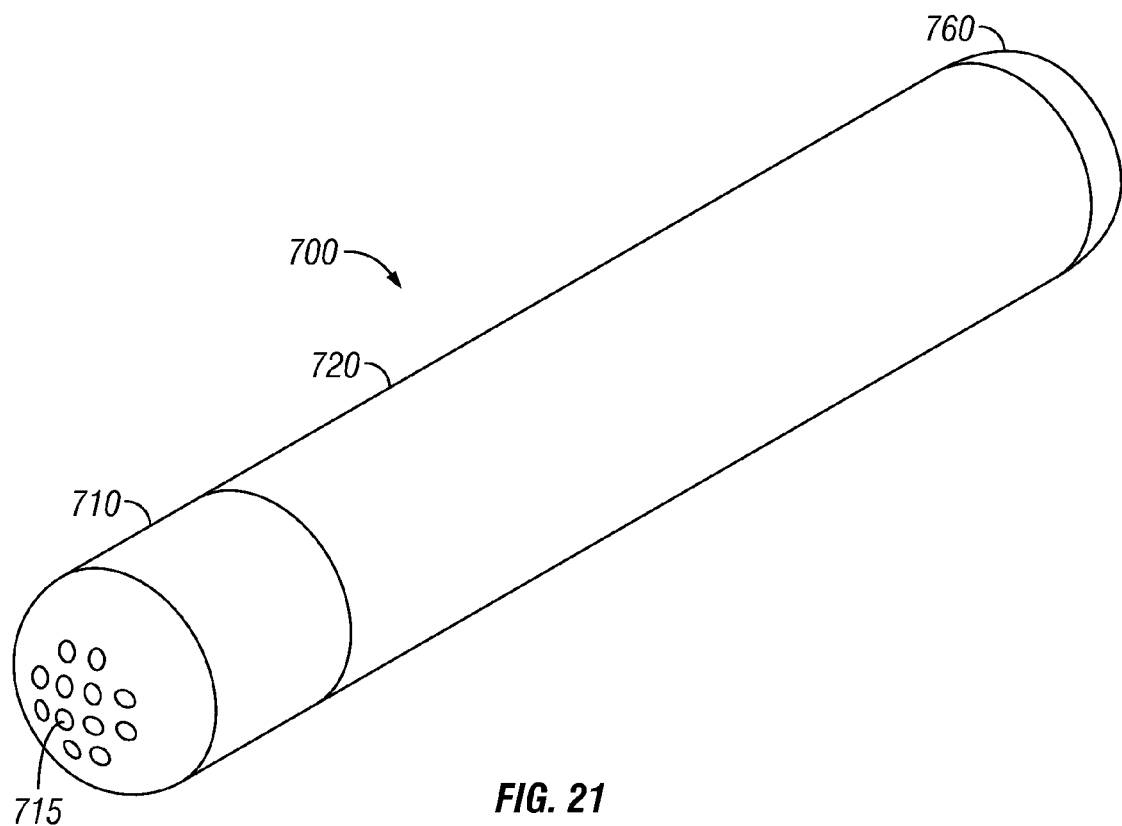
FIG. 21 is an assembled perspective view of a capsule according to an exemplary embodiment.
Figure 22:
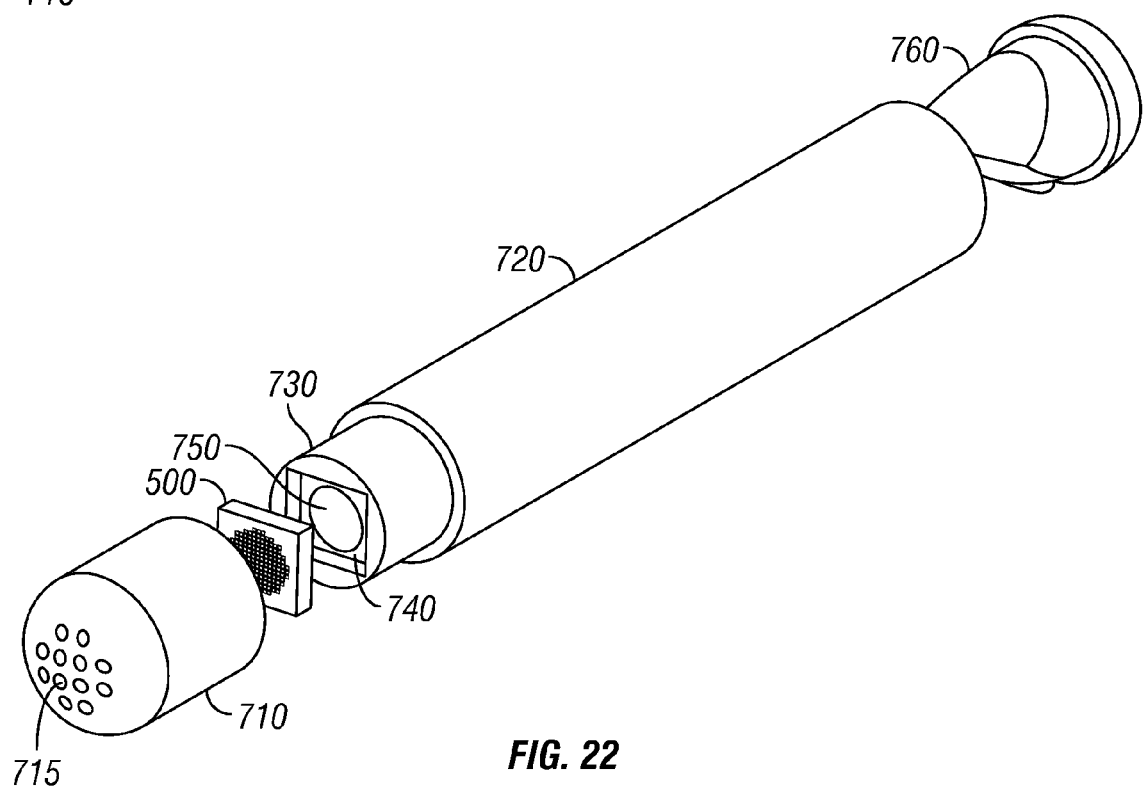
FIG. 22 is an exploded perspective view of the embodiment of FIG. 21.

Referring now to FIGS. 21 and 22, capsule 700 is similar to the previously-described capsule 600. However, in this embodiment capsule 700 is fitted with a septum 760 on the end of cylindrical body 720 that is distal from end portion 630. Septum 760 comprises a self-sealing material (e.g., silicone rubber) that permits injection of a therapeutic agent into inner volume 750 of cylindrical body 720. In certain embodiments, a therapeutic agent can be injected with a hypodermic needle just prior to implantation of capsule 700.

Figure 23:
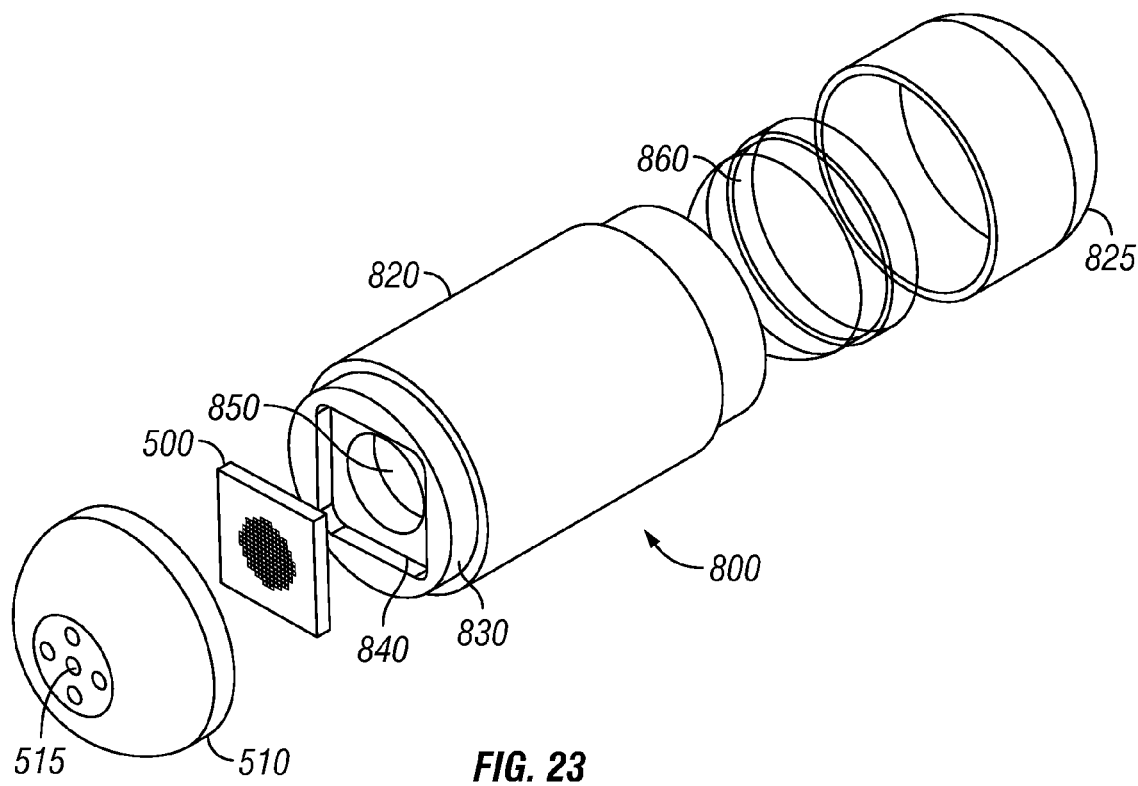
FIG. 23 is an exploded perspective view of a capsule and a nanochannel delivery device according to an exemplary embodiment.

Referring now to FIG. 23, a capsule 800 comprises components equivalent to previously-described embodiments. However, this embodiment comprises a cap 825 that covers septum 860. Cap 825 may comprise an orifice (not visible in the perspective view of FIG. 21) configured to guide a needle or other device used to penetrate septum 860 and inject a therapeutic agent into inner volume 850 of cylindrical body 820.

Figure 24:
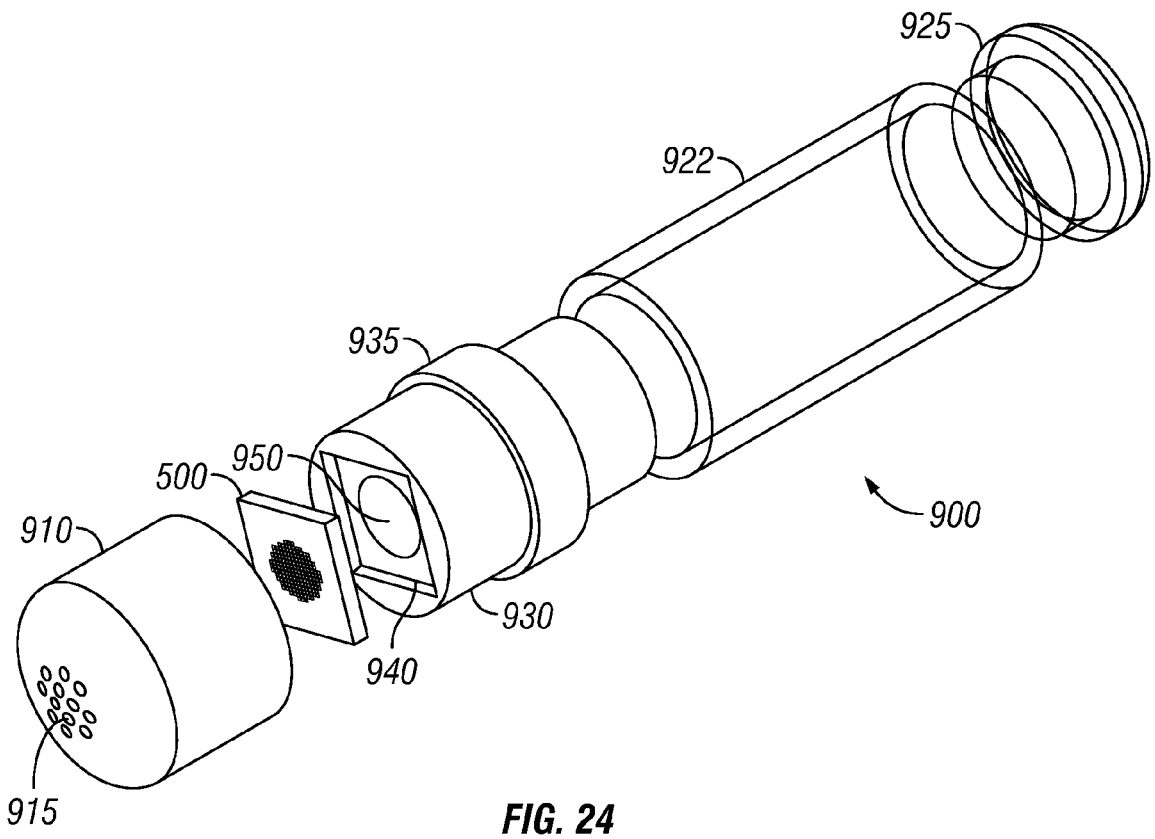
FIG. 24 is an exploded perspective view of a capsule and a nanochannel delivery device according to an exemplary embodiment.

Referring now to FIG. 24, a capsule 900 comprises a cylindrical body 922 coupled to a separate end component 935 and a cap 925. In this embodiment, cylindrical body 922 can be replaced with another cylindrical body having a different length in order to vary the internal volume of capsule 900 (and the amount of therapeutic agent that capsule 900 can contain). Similar to previous embodiments, end component 935 comprises an end portion 930 configured to receive cap 910. End component 935 also comprises a recessed portion 940 configured to receive nanochannel delivery device 500.

Figure 25:
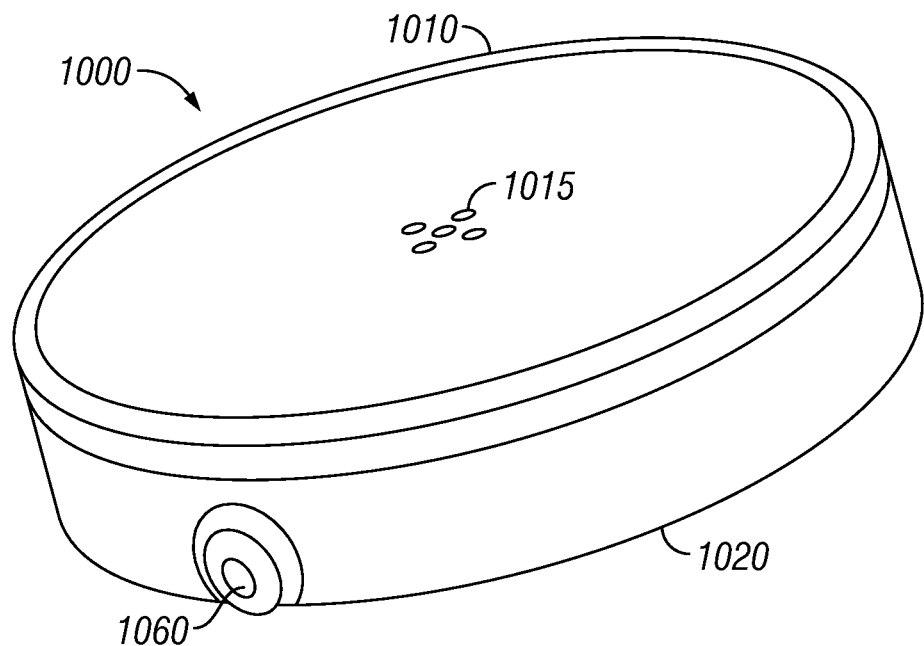
FIG. 25 is an assembled perspective view of a capsule according to an exemplary embodiment.
Figure 26:
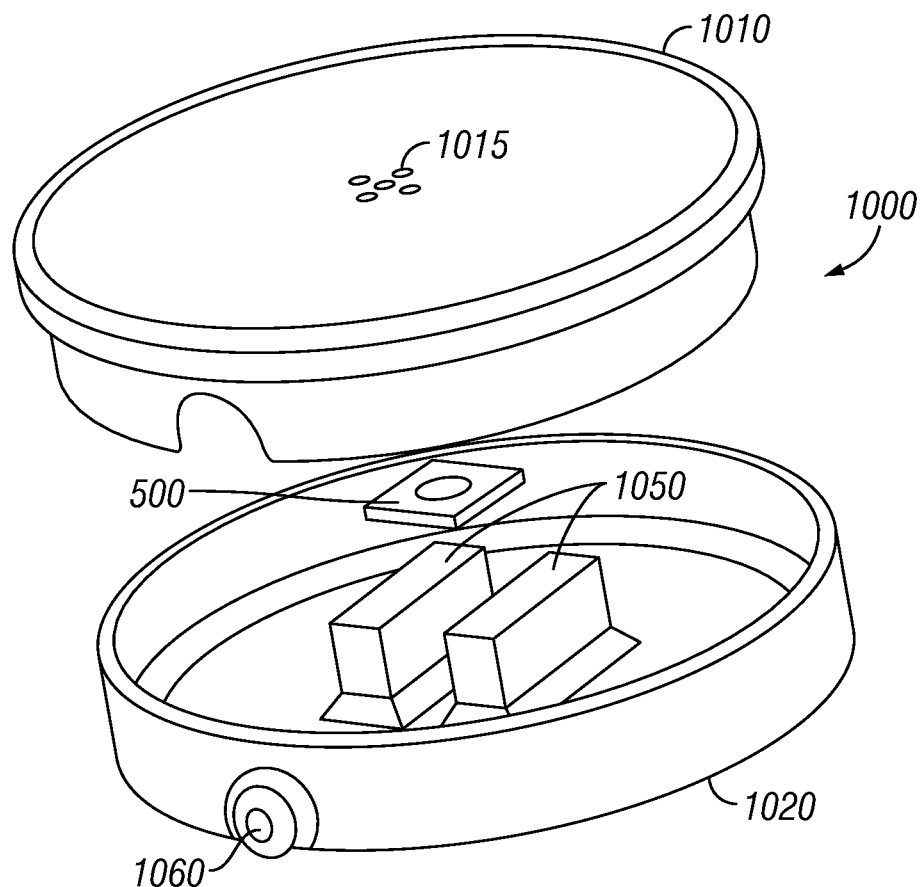
FIG. 26 is an exploded perspective view of the embodiment of FIG. 25.

Referring now to FIGS. 25 and 26, a capsule 1000 comprises a disc-shaped body 1020 with a cap 1010 comprising a series of exit ports 1015. In this embodiment, disc-shaped body 1020 comprises a septum 1060 through which a therapeutic agent may be injected. As shown in the exploded view of FIG. 26, supports 1050 can be used to hold nanochannel delivery device 500 proximal to exit ports 1015. In this manner, a therapeutic agent contained within capsule 1000 is forced to pass through nanochannel delivery device 500 proximal before exiting capsule 1000.

Figure 27:
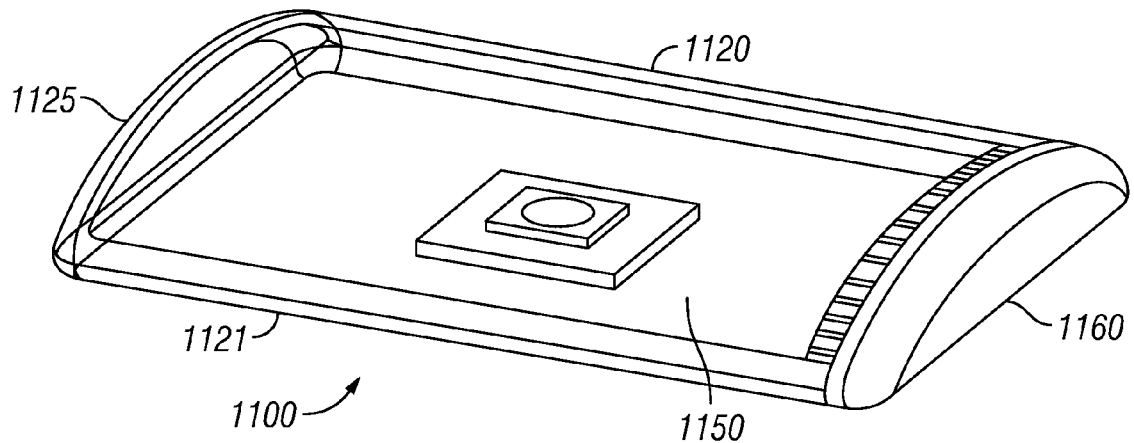
FIG. 27 is an assembled perspective view of a capsule according to an exemplary embodiment.
Figure 28:
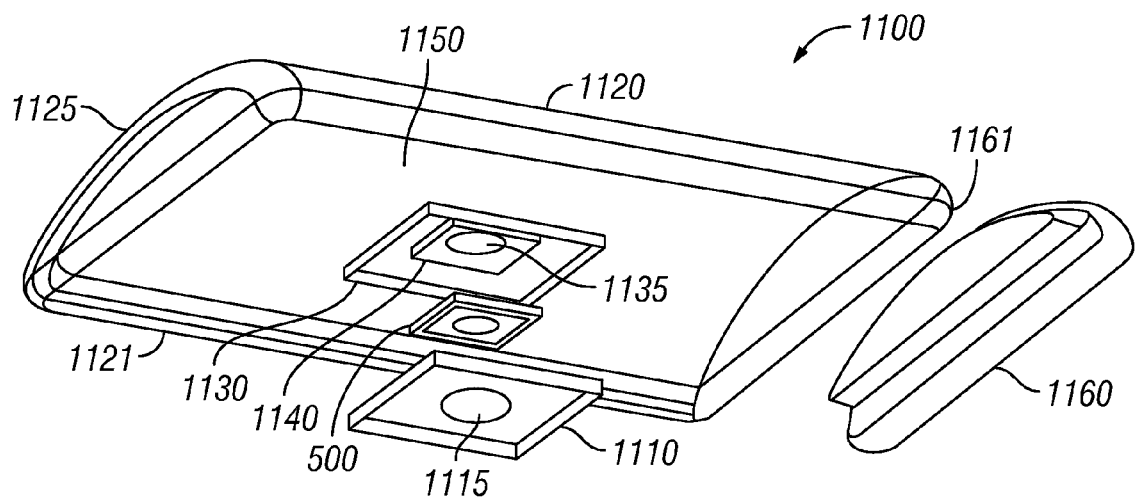
FIG. 28 is an exploded perspective view of the embodiment of FIG. 27.

In the embodiment shown in FIGS. 27 and 28, a capsule 1100 comprises a rectangular planar surface 1121 and an arched surface 1120. Capsule 1100 also comprises a closed end 1125 and a septum 1160 that can be inserted into an open end 1161. In the embodiment shown, septum 1160 covers the entire open end 1161. In other embodiments, a septum may cover part of an open end, and a cap may cover the remaining portions. Similar to previously-described embodiments, septum 1160 is self-sealing and can be punctured with a needle to insert a therapeutic agent. Capsule 1100 also comprises a first recessed portion 1140 configured to receive nanochannel delivery device 500, and a second recessed portion 1130 configured to receive a cap 1110 comprising exit ports 1115. An aperture 1135 extends through recessed portion 1140 into an inner volume 1150 bounded by rectangular planar surface 1121, arched surface 1120, closed end 1125 and septum 1160. In this embodiment, a therapeutic agent can be contained within inner volume 1150 and dispensed through aperture 1135, nanochannel delivery device 500, and exit ports 1115.

Figure 29:
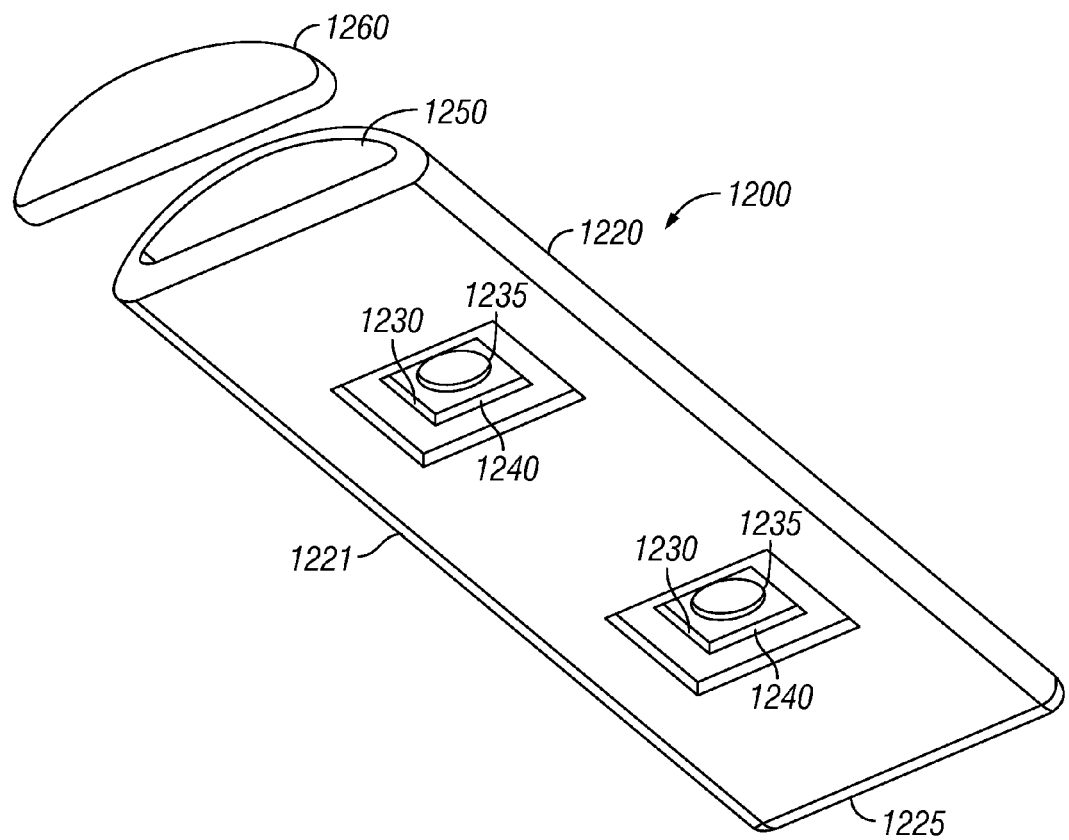
FIG. 29 is a perspective view of a capsule according to an exemplary embodiment.

Referring now to FIG. 29, another embodiment of a capsule 1200 is generally equivalent to capsule 1100, but comprises features that accommodate two nanochannel delivery devices (not shown). In this embodiment, capsule 1200 comprises a rectangular planar surface 1221, arched surface 1220, closed end 1225 and septum 1260. Capsule 1200 also comprises a pair of first recessed portion 1240 each configured to receive nanochannel delivery device (not shown), and a second pair of recessed portions 1230 each configured to receive a cap with exit ports (not shown). Each recessed portion 1240 comprises an aperture 1235 that provides fluid communication between inner volume 1250 and the environment surrounding capsule 1200.

In certain embodiments, inner volume 1250 comprises separate, internal reservoirs in which each reservoir is in fluid communication with a single aperture 1235. The internal reservoirs may be separated by inner walls within aperture 1235. In such embodiments, each reservoir may be filled with a separate therapeutic agent. Each nanochannel device can be configured to provide the preferred dosage of each individual therapeutic agent.

Figure 30:
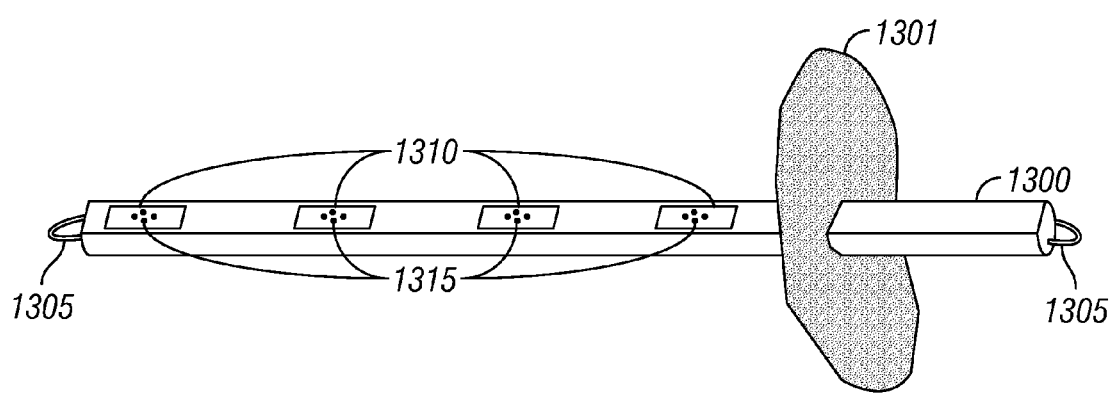
FIG. 30 is a perspective view of a capsule according to an exemplary embodiment in an installed location.

Referring now to FIG. 30, another embodiment of a capsule 1300 is shown in an installed position so that it partially extends beneath an epidermal surface 1301 of a patient into which capsule 1300 has been inserted. Capsule 1300 comprises multiple covers 1310 with exit ports 1315. Beneath each cover 1310, a nanochannel delivery device is inserted over an aperture that is in fluid communication with an inner volume of capsule 1300 (similar to the embodiments described in FIGS. 27-29). The inner volume of capsule 1300 may be divided into separate compartments so that each nanochannel delivery device can be used to administer a specific and distinct therapeutic agent. Capsule 1300 also comprises an anchor member 1305 configured to serve as a point at which a suture (not shown) can be attached to capsule 1300 when it is installed. Anchor member 1305 may also be coupled to a string or other device (not shown) used to remove or retrieve capsule 1300.

Figure 31:
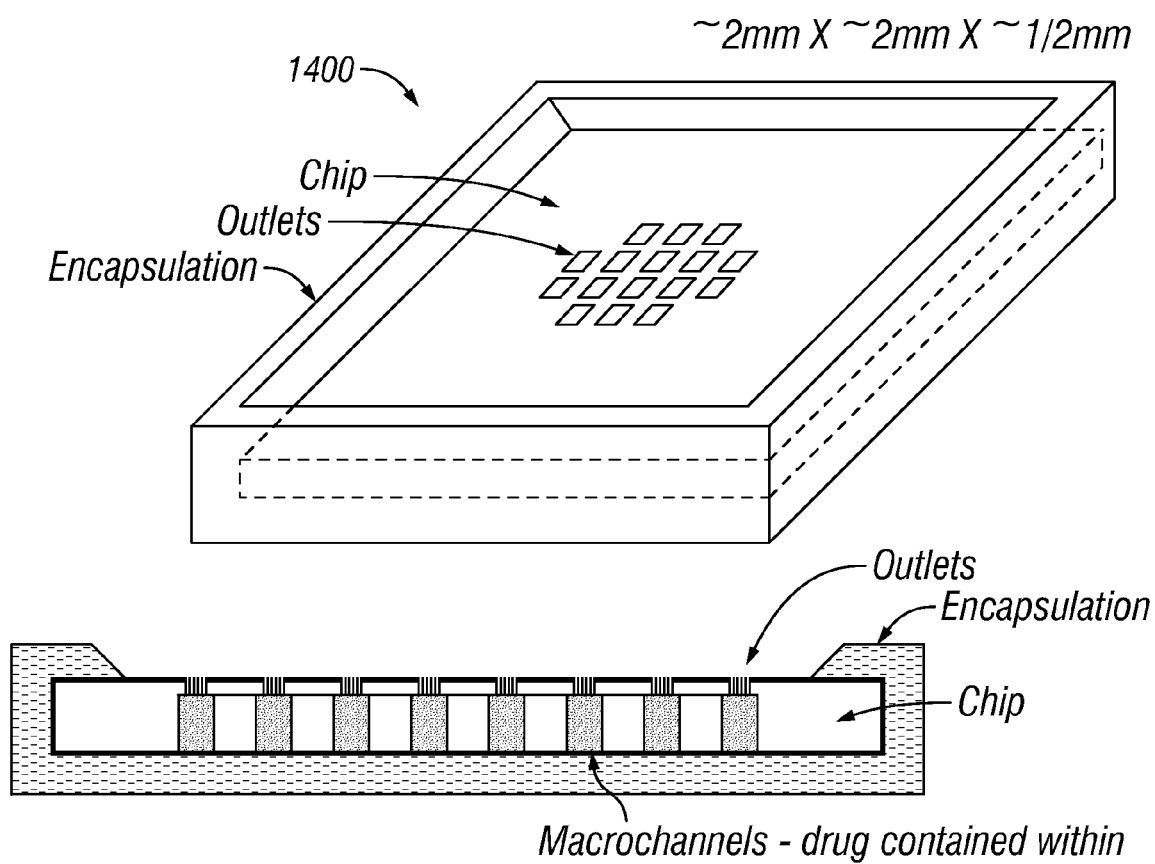
FIG. 31 is a perspective view and a section view of a capsule according to an exemplary embodiment.

Referring now to FIG. 31, another embodiment of a capsule 1400 is shown. This capsule is a minimal covering of the back and sides of the nanochannel device, such that the "reservoir" for a contained drug is limited to the volume of the macrochannels on the back of the chip (e.g., the nanochannel delivery device), which is about 4.5 mm$^3$ for the embodiment shown in FIG. 8K. This embodiment can be made particularly small, for example 2 mm×2 mm×0.5 mm, and is, therefore, especially suited for implantation with very high potency drugs into sensitive locations, e.g., glaucoma medication into the inner portion of the eye.

Exemplary embodiments of the previously-described capsules can be sized so that the capsule may be implanted subcutaneously. In specific embodiments, the capsule may have a diameter of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6.0, 7.0, 8.0, 9.0, 10.0, 11.0, 12.0, 13.0, 14.0, 15.0, 16.0, 17.0, 18.0, 19.0 or 20.0 mm. In other embodiments, the capsule may be greater than 20.0 mm in diameter.

In certain embodiments, the capsule may have a thickness of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0 mm. In other embodiments, the capsule may have a thickness greater than 10.0 mm.

In specific embodiments, a capsule may have a width of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mm. In other embodiments, the capsule may have a width greater than 100 mm.

In specific embodiments, a capsule may have a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 mm. In other embodiments, the capsule may have a length greater than 200 mm.

It is noted that the various embodiments of capsules described in this disclosure comprise a cross-section that is nominally constant along the length of the capsule. Such an optional configuration can facilitate sliding removal from a surgical site within the body without damage to surrounding tissue.

In exemplary embodiments a capsule may comprise suitable materials such as stainless steel, titanium, polyetheretherkeytone, polysulfone, and other plastics and metals. In certain embodiments, a capsule may comprise coating(s) on the interior to provide an optimal environment for a therapeutic substance and/or coating(s) on the exterior to prevent deleterious tissue encapsulation. In specific embodiments, the capsule may comprise color coding to indicate the model of the capsule or a particular characteristic (e.g., the therapeutic agent, rate of administering the agent, the capacity of the capsule, etc.). In certain embodiments, a capsule may comprise a translucent or transparent portion or component (e.g. a cap) to facilitate observation of the quantity of therapeutic agent contained within the capsule. For example, a translucent or transparent cap covering the nanochannel delivery device can allow a person to confirm the capsule is full by orienting the capsule so that the nanochannel delivery device is positioned towards the top of the capsule. A needle (or other loading device) can then penetrate the septum and the therapeutic agent can be injected into the capsule. When liquid appears on the top of the nanochannel delivery device (as viewed through the cap), the person filling the capsule will have an indication that the capsule is full.

In exemplary embodiments, a capsule may be used to administer one or more of the following substances: adrenergic agent; adrenocortical steroid; adrenocortical suppressant; aldosterone; alkylating agent; antagonist; amino acid; anabolic; analeptic; analgesic; anesthetic; anorexogenic; anti-acne agent; anti-adrenergic; anti-allergic; anti-alopecia agent; anti-amebic; anti-anemic; anti-anginal; antiangiogenic, anti-anxiety; anti-arthritic; anti-asthmatic; anti-atherosclerotic; antibacterial; antibiotic; anticancer; anticholinergic; anticoagulant; anticonvulsant; antidepressant; antidiabetic; antidiarrheal; antidiuretic; anti-dyskinetic; antiemetic; anti-epileptic; antifibrinolytic; antifungal; anti-hemorrhagic; antihistamine; anti-hypercalcemic, anti-hypercholesterolaemic; anti-hyperlipidaemic; anti-hypertensive; anti-hypertriglyceridemic; anti-hypotensive; anti-infective; anti-inflammatory; anti-ischemic; antimicrobial; antimigraine; antimitotic; antimycotic; anti-nauseant; anti-neoplastic;

anti-neutropenic; anti-obesity agent; anti-osteoporotic, antiparasitic; antiproliferative; antipsychotic; antiretroviral; anti-resorptives; anti-rheumatic; anti-seborrheic; antisecretory; antispasmodic; antisclerotic; antithrombotic; antitumor; anti-ulcerative; antiviral; appetite suppressant; bisphosphonate; blood glucose regulator; bronchodilator; cardiovascular agent; central nervous system agent; contraceptive; cholinergic; concentration aid; depressant; diagnostic aid; diuretic; DNA-containing agent, dopaminergic agent; estrogen receptor agonist; fertility agent; fibrinolytic; fluorescent agent; free oxygen radical scavenger; gastric acid supressant; gastrointestinal motility effector; glucocorticoid; glutamatergic agent; hair growth stimulant; hemostatic; histamine H2 receptor antagonist; hormone; hypocholesterolemic; hypoglycemic; hypolipidemic; hypotensive; imaging agent; immunizing agent; immunomodulator; immunostimulant; immunosuppressant; interleukin, keratolytic; LHRH agonist; mood regulator; mucolytic; mydriatic; nasal decongestant; neuromuscular blocking agent; neuroprotective; NMDA antagonist; non-hormonal sterol derivative; nootropic agent; parasympathomimetic agent; plasminogen activator; platelet activating factor antagonist; platelet aggregation inhibitor; platinum-containing agent, psychotropic; radioactive agent; raf antagonist, RNA-containing agent, scabicide; sclerosing agent; sedative; sedative-hypnotic; selective adenosine A1 antagonist; selective estrogen receptor modulator, serotonin antagonist; serotonin inhibitor; serotonin receptor antagonist; steroid; stimulant; thrombic agent; thyroid hormone; thyroid inhibitor; thyromimetic; tranquilizer; vasoconstrictor; vasodilator; wound healing agent; xanthine oxidase inhibitor; and the like; Abacavir, Abacavir sulfate, abatacept, Acarbose, Acetaminophen, Aciclovir, Adalimumab, Adapalene, Alendronate, Alendronate sodium, Alfuzosin, aliskiren, allopurinol, alvimopan, ambrisentan, Aminocaproic acid, Amitriptyline hydrochloride, amlodipine, amlodipine besylate, amoxicillin, amoxicilline, Amphetamine, Anastrozole, Aripiprazole, armodafinil, Atazanavir, atenolol, Atomoxetine, atorvastatin calcium, atorvastatin, Atropine sulfate, Azelastine, azithromycin, Balsalazide, Benazepril, bendamustine hydrochloride, Benzepril hydrochloride, bevacizumab, Bicalutamide, Bimatoprost, Bisoprolol, Bisoprolol fumarate, Bosentan, Botulin toxin, Budesonide, Buformin, Buprenorphine, Bupropion, bupropion hydrobromide, Bupropion Hydrochloride, Cabergoline, Calcipotriol, calcitriol, candesartan cilexetil, Capecitabine, Captopril, carbidopa, carisoprodol, Carvedilol, Caspofungin, Cefdinir, Cefoperazone, Cefotiam, cefprozil, Cefuroxime, Celecoxib, cephalaxin, Certolizumab Pegol, Cetirizine, Cetrizine hydrochloride, Cetuximab, Chlorpromazine hydrochloride, Chlorpheniramine maleate, ciclesonide, Cilastatin, cimetidine, Cinacalcet, Ciprofloxacin, citalopram hydrobromide, Clarithromycin, Clindamycin, Clindamycin, clindamycin hydrochloride, Clomipramine hydrochloride, Clonidine hydrochloride, clopidogrel, Clopidogrel bisulfate, Cloxacillin Sodium, Co-Amoxiclav, Codeine phosphate, Colchicines, Colesevelam, cyclobenzaprine hydrochloride, Cyclophosphamide, Cyclosporine, darbepoetin alfa, Darifenacin, DCRM 197 protein, Desloratadine, desloratidine, Desmopressin sulfate, Desoximetasone, dexamethasone, Diclofenac, Diethylcarbamazine citrate, difluprednate, diphenhydramine, Dipyridamole, DL-methionine, Docetaxel, Donepezil, doripenem, Dorzolamide, Doxazosin, doxazosin mesylate, doxycydine, Drospirenone, Duloxetine, Dutasteride, eculizumab, Efavirenz, Emtricitabine, Enalapril, enalapril maleate, Enoxaparin Sodium, Eprosartan, Erlotinib, Erythromycin, Erythropoietin, Escitalopram, esomeprazole, estradiol, Estrogen, Eszopiclone, etanercept, Ethembutol hydrochloride, Ethosuximide, ethynl estradiol, etonogestrel, etoricoxib, etravirine, Exenatide, Ezetimibe, Ezetimibe, Factor VII, famotidine, Famotidine, Fenofibrate, Fenofibrate, Fentanyl, Fentanyl citrate, Ferrous sulfate, Fexofenadine, fexofenadine hydrochloride, Filgrastim, Finasteride, fluconazole, Fluoxetine hydrochloride, Fluticasone, Fluvastatin, folic acid, Follitropin alfa, Follitropin beta, Formoterol, Fosinopril sodium, Gabapentin, Gabapentin, Gemcitabine, glargine insulin, Glatiramer, glimepride, Goserelin, histrelin acetate, Human growth hormone, Hydralazine hydrochloride, Hydrocodone bitartrate, Hydroxyurea, Hydroxyzine hydrochloride, Ibandronate, Imatinib, Imiglucerase, Imipenem, imiquimod, Indinavir sulfate, infliximab, Interferon beta-1a, Ipratropium, Irbesartan, Irinotecan, Isoniazid, Isosorbide moninitrate, ixabepilone, ketamine, ketoconazole, Ketorolac, Lactobionate, Lamivudine, Lamivudine, Lamotrigine, lanreotide acetate, Lansoprazole, lapatinib, laropiprant, Latanoprost, Letrozole, Leuprolide, Levalbuterol, Levamisole hydrochloride, Levetiracetam, levocetirizine dihydrochloride, levodopa, Levofloxacin, levonorgestrel, Levothyroxine, levothyroxine sodium, Lidocaine, Linezolid, Lisdexamfetamine Dimesylate, Lisinopril, Lispro insulin, Lopinavir, Loratadine, lorazepam, Losartan potassium, maraviroc, Marinol, meclizine hydrochloride, Meloxicam, Memantine, Meropenem, metaxalone, metformin, Metformin Hydrochloride, methadone, methoxy polyethylene glycol-epoetin beta, Methylphenidate, Methylphenidate hydrochloride, Metoprolol, Metoprolol tartrate, metronidazole, Metronidazole, miglitol, Minocycline, Minocycline hydrochloride, mirtazepine, Modafinil, Mometasone, montelukast, Montelukast sodium, Morphine, Moxifloxacin, Mycophenolate mofetil, Naloxone, Naproxen sodium, natalizumab, Neostigmine bromide, Niacin, Nicotinamide, Nifedipine, Nifurtimox, nilotinib hydrochloride monohydrate, nitrofurantoin, Nortriptyline hydrochloride, nystatin, olanzapine, Olanzepine, Olmesartan, olmesartan medoxomil, olopatadine hydrochloride, Omalizumab, Omega-3 acid ethyl esters, Omeprazole, Ondansetron, Orlistat, Oseltamivir, Oxaliplatin, Oxcarbazepine, Oxybytynin chloride, oxycodone hydrochloride, Paclitaxel, Palivizumab, Pantoprazole, paracetamol, Paroxetine, paroxetine hydrochloride, Pegylated interferon alfa-2a, Pemetrexed, Penicillamine, Penicillin V potassium, Phenformin, Phenyloin sodium, Pioglitazone, Piperacillin, Potassium chloride, Pramipexole, Pravastatin, Pravastatin sodium, prednisolone quetiapine fumerate, Pregabalin, Primaquine phosphate, Progesterone, Promethazine, Promethazine hydrochloride, Proponolol hydrochloride, Propoxyphene hydrochloride, pseudoephedrine, Pseudophedrine hydrochloride, Pyridostigmine bromide, Pyridoxine hydrochloride, Quetiapine, quetiapine fumarate, Quinapril hydrochloride, Rabeprazole, raloxifene, raltegravir, Ramipril, Ranitidine, Ranitidine hydrochloride, Recombinant factor VIII, retapamulin, Rimonabant, Risedronate, Risedronate sodium, risperidone, Ritonavir, rituximab, Rivastigmine, rivastigmine tartrate, Rizatriptan, Ropinirole, rosiglitazone, Rosiglitazone maleate, Rosuvastatin, Rotavirus vaccine, rotigotine, Salbutamol, Salbutamol sulfate, salmeterol, sapropterin dihydrochloride, Sertraline, sertraline hydrochloride, Sevelamer, Sevoflurane, Sildenafil, sildenafil citrate, simvastatin, Simvastatin, Sitagliptin, Sodium valproate, Solifenacin, Somatostatin, Somatropin, Stavudine, Sulfomethoxazole, Sumatriptan, Sumatriptan succinate, Tacrolimus, Tadalafil, tamoxifen citrate, Tamsulosin, tamsulosin hydrochloride, Tegaserod, Telmisartan, temazepam, Temozolomide, temsirolimus, Tenofovir, Terazosin Hydrochloride, Terbinafine, Teriparatide, testosterone, Tetracycline hydrochloride, Thalidomide, thymopentin, Timolol meleate, Tiotropium, tipranavir, Tolterodine, tolterodine tartrate, topiramate, topotecan, Tramadol, Tramadol hydrochloride, trastuzumab, trazodone hydrochloride, trimethoprim, Valaciclovir, Valacyclovir hydrochloride, Valproate semisodium, valsartan, Vancomycin, Vardenafil, Varenicline, venlafaxine, Venlafaxine hydrochloride, Verapamil Hydrochloride, vildagliptin, Voglibose, Voriconazole, Wafarin sodium acetylsalicylic acid, Zaleplon, Zidovudine, Ziprasidone, Zoledronate, Zolpidem, or pharmaceutically acceptable salts thereof; 16-alpha fluoroestradiol, 17-alpha dihydroequilenin, 17-alpha estradiol, 17-beta estradiol, 17-hydroxyprogesterone, 1-dodecpyrrolidinone, 22-oxacalcitriol, 3-isobutyl-gamma-butyric acid, 6-fluoroursodeoxycholic acid, 7-methoxytacrine, Abacavir, Abacavir sulfate, Abamectin, abanoquil, abatacept, abecarnil, abiraterone, Ablukast, Ablukast Sodium, Acadesine, acamprosate, Acarbose, Acebutolol, Acecamide Hydrochloride, Aceclidine, aceclofenae, Acedapsone, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Aciclovir, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, Adatanserin Hydrochloride, adafenoxate, Adalimumab, Adapalene, adatanserin, adecypenol, adecypenol, Adefovir, adelmidrol, ademetionine, Adenosine, Adinazolam, Adipheinine Hydrochloride, adiposin, Adozelesin, adrafinil, Adrenalone, Aiclometasone Dipropionate, airbutamine, alacepril, Alamecin, Alanine, Alaproclate, alaptide, Albendazole, albolabrin, Albuterol, Alclofenae, Alcloxa, aldecalmycin, Aldesleukin, Aldioxa, Aletamine Hydrochloride, Alendronate, Alendronate Sodium, alendronic acid, alentemol, Alentemol Hydrobromide, Aleuronium Chloride, Alexidine, alfacalcidol, Alfentanil Hydrochloride, alfuzosin, Algestone Acetonide, alglucerase, Aliflurane, alinastine, Alipamide, aliskiren, Allantoin, Allobarbital, Allopurinol, Alonimid, alosetron, Alosetron Hydrochloride, Alovudine, Alpertine, alphaidosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverinc Citrate, alvimopan, Alvircept Sudotox, Amadinone Acetate, Amantadine Hydrochloride, ambamustine, Ambomycin, ambrisentan, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amfiutizole, Amicycline, Amidephrine Mesylate, amidox, Amifloxacin, amifostine, Amilcacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, amlodipine besylate, Amobarbital Sodium, Amodiaquine, Amodiaquine Hydrochloride, Amorolfine, Amoxapine, Amoxicillin, Amphecloral, Amphetamine, Amphetamine Sulfate, Amphomycin, Amphoterin B, Ampicillin, ampiroxieam, Ampyzine Sulfate, Amquinate, Amrinone, amrubicin, Amsacrine, Amylase, amylin, amythiamicin, Anagestone Acetate, anagrelide, Anakinra, ananain, anaritide, Anaritide Acetate, Anastrozole, Anazolene Sodium, Ancrod, andrographolide, Androstenedione, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramy ci antiandrogen, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, Aripiprazole, armodafinil, arotinolol, Arpinocid, Arteflene, Artilide Fumarate, asimadoline, aspalatone, Asparaginase, Aspartic Acid, Aspartocin, asperfuran, Aspirin, aspoxicillin, Asprelin, Astemizole, Astromicin Sulfate, asulacrine, atamestane, Atazanavir, Atenolol, atevirdine, Atipamezole, Atiprosin Maleate, Atolide, Atomoxetine, atorvastatin, Atorvastatin Calcium, Atosiban, Atovaquone, atpenin B, Atracurium Besylate, atrimustine, atrinositol, Atropine, Atropine sulfate, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, Azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basic, Basifungin, Batanopride Hydrochloride, batebulast, Batelapine Maleate, Batimastat, beau vericin, Becanthone Hydrochloride, becaplermin, becliconazole, Beclomethasone Dipropionate, befloxatone, Beinserazide, Belfosdil, Belladonna, Beloxamide, Bemesetron, Bemitradine, Bemoradan, Benapryzine Hydrochloride, Benazepril, Benazepril Hydrochloride, Benazeprilat, Benda calol Mesylate, bendamustine hydrochloride, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzepril hydrochloride, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, betaalethine, betaclamycin B, Betamethasone, betamipron, betaxolol, Betaxolol Hydrochloride, Bethanechol Chloride, Bethanidine Sulfate, betulinic acid, bevacizumab, bevantolol, Bevantolol Hydrochloride, Bezafibrate, Bialamicol Hydrochloride, Biapenem, Bicalutamide, Bicifadine Hydrochloride, Biclodil Hydrochloride, Bidisomide, bifemelane, Bifonazole, bimakalim, Bimatoprost, bimithil, Bindarit, Biniramycin, binospirone, bioxalomycin, Bipenamol Hydrochloride, Biperiden, Biphenamine Hydrochloride, biriperone, bisantrene, bisaramil, bisaziridinylspermine, bis-benzimid zole A, bis-benzimidazole B, bisnafide, Bisobrin Lactate, Bisoprolol, Bisoprolol fumarate, Bispyrithione Magsulfex, bistramide D, bistramide K, bistratene A, Bithionolate Sodium, Bitolterol Mesylate, Bivalirudin, Bizelesin, Bleomycin Sulfate, boldine, Bolandiol Dipropionate, Bolasterone, Boldenone Undecylenate, Bolenol, Bolmantalate, bopindolol, Bosentan, Botulin toxin, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelain, bromfenac, Brominidione, Bromocriptine, Bromodiphenhydramine Hydrochloride, Bromoxanide, Bromperidol, Bromperidol Decanoate, Brompheniramine Maleate, Broperamole, Bropirimine, Brotizolam, Bucamide Maleate, bucindolol, Buclizine Hydrochloride, Bucromarone, Budesonide, budipine, budotitane, Buformin, Bumetanide, Bunaprolast, bunazosin, Bunolol Hydrochloride, Bupicomide, Bupivacaine Hydrochloride, Buprenorphine, Buprenorphine Hydrochloride, Bupropion, bupropion hydrobromide, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthioninc sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cabergoline, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, Cammonam Sodium, camonagrel, canary pox IL-2, candesartan, candesartan cilexetil, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Car bocysteine, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbol-Fuchsin, Carboplatin, Carboprost, carbovir, carboxamide-amino-triazo-le, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Camidazole, Caroxazone, carperitide, Carphenazine Maleate, Carprofen, Carsatrin Succinate, Cartazolate, carteolol, Carteolol Hydrochloride, Carubicin Hydrochloride, carvedilol, carvotroline, Carvotroline Hydrochloride, carzelesin, Caspofungin, castanospermine, caurumonam, cebaracetam, cecropin B, Cedefingol, Cefaclor, Cefadroxil, Cefamandole, Cefaparole, Cefatrizine, Cefazaflur Sodium, Cefazolin, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefinetazole, cefminlox, cefodizime, Cefonicid Sodium, Cefoperazone, Cefoperazone Sodium, Ceforanide, cefoselis, Cefotaxime Sodium, Cefotetan, cefotiam, Cefoxitin, cefozopran, Cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxooe, Cefuroxime, celastrol, Celecoxib, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceruletide, Ceronapril, Certolizumab Pegol, certoparin sodium, Cetaben Sodium, Cetalkonium Chloride, Cetamolol Hydrochloride, Cethuperazone, cetiedil, cetirizine, Cetophenicol, Cetraxate Hydrochloride, Cetrizine hydrochloride, cetrorelix, Cetuximab, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphe niramine Maleate, Chlorphenesin Carbamate, Chlorpheniramine maleate, Chlorpromazine, Chlorpromazine hydrochloride, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin, Cilastatin Sodium, Cilazapril, cilnidipine, Cilobamine Mesylate, cilobradine, Cilofungin, cilostazol, Cimaterol, Cimetidine, cimetropium bromide, Cinacalcet, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Ciot eronel, Cipamfylline, Ciprefadol Succinate, Ciprocinonide, Ciprofibrate, Ciprofloxacin, ciprostene, Ciramadol, Cirolemycin, C is platin, cisapride, cisatracurium besilate, Cisconazole, cis-porphyrin, cistinexine, citalopram, citalopram hydrobromide, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, clindamycin hydrochloride, Clioquinol, Clioxanide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Cloge stone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonidine hydrochloride, Clonitrate, Clonixeril, Clonixin, Clopamide, Clopenthixol, Cloperidone Hydrochloride, clopidogrel, Clopidogrel bisulfate, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortemine Hydrochloride, Closantel, Closiramine Aceturate, Clothiapine, Clothixamide Maleate Cloticasone Propionate, Clotrimazole, Cloxacillin Benzathine, Cloxacillin Sodium, Cloxyquin, Clozapine, Co-Amoxiclav, Cocaine, Coccidioidin, Codeine, Codeine phosphate, Codoxime, Colchicine, Colesevelam, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, complestatin, conagenin, Conorphone Hydrochloride, contignasterol, contortrostatin, Cormethasone Acetate, Corticorelin Ovine Tnflutate, Corticotropin, Cortisone Acetate, Cortivazol, Cortodoxone, cosalane, costatolide, Cosyntropin, cotinine, Coumadin, Coumermycin, crambescidin, Crilvastatin, crisnatol, Cromitrile Sodium, Cromolyn Sodium, Crotamiton, cryptophycin, cucumariosid, Cuprimyxin, curacin A, curdlan sulfate, curiosin, Cyclacillin, Cyclazocine, cyclazosin, Cyclindole, Cycliramine Maleate, Cyclizine, Cyclobendazole, cyclobenzaprine, cyclobenzaprine hydrochloride, cyclobut A, cyclobut G, cyclocapron, Cycloguanil Pamoate, Cycloheximide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cyponamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine ocfosfate, cytochalasin B, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, daphlnodorin A, dapiprazole, dapitant, Dapoxetine Hydrochloride, Dapsone, Daptomycin, darbepoetin alfa, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, DCRM 197 protein, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, Desloratadine, deslorelin, desmopressin, Desmopressin sulfate, desogestrel, Desonide, Desoximetasone, desoxoamiodarone, Desoxy-corticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichliorvos, Dichloralphenazone, Dichlorphenamide, Dicirenone, Diclofenac, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, Dimethyl Sulfoxide, dimethylhomospermine, dimethylprostaglandin A1, dimiracetam, Dimoxamine Hydrochloride, Dinoprost, Dinoprostone, Dioxadrol Hydrochloride, dioxamycin, diphenhydramine, Diphenhydramine Citrate, Diphenidol, Diphenoxylate Hydrochloride, diphenylspiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfuram, Ditekiren, Divalproex Sodium, Dizocilpine Maleate, DL-methionine, Dobutamine, docarpamine, Docebenone, Docetaxel, Doconazole, docosanol, dofetilide, dolasetron, Donepezil, doripenem, Dorzolamide, Doxazosin, doxazosin mesylate, doxycidine, Drospirenone, Duloxetine, Dutasteride, Ebastine, ebiratide, ebrotidine, ebselen, ecabapide, ecabet, ecadotril, ecdisteron, echicetin, echistatin, Echothiophate Iodide, Eclanamine Maleate, Eclazolast, ecomustine, Econazole, ecteinascidin 722, eculizumab, edaravone, Edatrexate, edelfosine, Edifolone Acetate, edobacomab, Edoxudine, edrecolomab, Edrophonium Chloride, edroxyprogesteone Acetate, Efavirenz, efegatran, eflornithine, efonidipine, egualcen, Elantrine, eleatonin, elemene, eletriptan, elgodipine, eliprodil, Elsamitrucin, eltenae, Elucaine, emailcalim, emedastine, Emetine Hydrochloride, emiglitate, Emilium Tosylate, emitefur, emoctakin, Emtricitabine, Enadoline Hydrochloride, Enailciren, enalapril, enalapril maleate, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, episteride, Eprosartan, eptastigmine, equilenin, Equilin, Erbulozole, erdosteine, Ergoloid Mesylates, Ergonovine Maleate, Ergotamine Tartrate, Erlotinib, ersentilide, Ersofermin, erythritol, Erythrityl Tetranitrate, Erythromycin, Erythropoetin, Escitalopram, Esmolol Hydrochloride, esomeprazole, Esorubicin Hydrochloride, Esproquin Hydrochloride, Estazolam, Estradiol, Estramustine, Estrazinol Hydrobromide, Estriol, Estrofurate, Estrogen, Estrone, Estropipate, esuprone, Eszopiclone, Etafedrine Hydrochloride, etanercept, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ethembutol hydrochloride, Ethinyl estradiol, Ethiodized Oil, Ethionamide, Ethonam Nitrate, Ethopropazine Hydrochloride, Ethosuximide, Ethosuximide, Ethotoin, Ethoxazene Hydrochloride, Ethybenztropine, Ethyl Chloride, Ethyl Dibunate, Ethylestrenol, Ethyndiol, Ethynerone, ethynl estradiol, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, etoricoxib, Etoxadrol Hydrochloride, Etozolin, etrabamine, etravirine, Etretinate, Etryptamine Acetate, Eucatropine Hydrochloride, Eugenol, Euprocin Hydrochloride, eveninomicin, Exametazime, examorelin, Exaprolol Hydrochloride, exemestane, Exenatide, Ezetimibe, Ezetimibe, Factor VII, fadrozole, faeriefungin, Famciclovir, Famotidine, Fampridine, fantofarone, Fantridone Hydrochloride, faropenem, fasidotril, fasudil, fazarabine, fedotozine, Felbamate, felbamate, Felbinac, Felodipine, Felypressin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, Fenofibrate, fenoldopam, Fenoprofen, Fenoterol, Fenpipalone, Fenprinast Hydrochloride, Fenprostalene, Fenquizone, fenretinide, fenspiride, fentanyl, Fentanyl Citrate, Fentiazac, Fenticlor, fenticonazole, Fenyripol Hydrochloride, fepradinol, ferpifosate sodium, ferristene, ferrixan, Ferrous Sulfate, Ferumoxides, ferumoxsil, Fetoxylate Hydrochloride, Fexofenadine, fexofenadine hydrochloride, Fezolamine Fumarate, Fiacitabine, Fialuridine, fibmoxef, Fibrinogen, Filgrastim, Filipin, Finasteride, fiorfenicol, fiorifenine, fiosatidil, fiumecinol, fiunarizine, fiuparoxan, fiupirtine, fiurithromycin, fiutrimazole, fiuvastatin, fiuvoxamine, Flavodilol Maleate, flavopiridol, Flavoxate Hydrochloride, Flazalone, flecamide, flerobuterol, Fleroxacin, flesinoxan, Flestolol Sulfate, Fletazepam, flezelastine, flobufen, Floctafenine, Flordipine, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose, Fludorex, Fludrocortisone Acetate, Flufenamic Acid, Flufenisal, Flumazenil, Flumequine, Flumeridone, Flumethasone, Flumetramide, Flumezapine, Fluminorex, Flumizole, Flumoxonide, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa, Fluorometholone, Fluorouracil, Fluotracen Hydrochloride, Fluoxetine, Fluoxetine hydrochloride, Fluoxymesterone, Fluperamide, Fluperolone Acetate, Fluphenazine Decanoate, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, Fluorocitabine, Fluorofamide, Fluorogestone Acetate, Fluorothyl, Fluoroxene, Fluspiperone, Fluspirilene, Fluticasone, Fluticasone Propionate, Flutroline, Fluvastatin, Fluvastatin Sodium, Fluzinamide, Folic Acid, Follicle regulatory protein, Folliculostatin, Follitropin alfa, Follitropin beta, Fomepizole, Fonazine Mesylate, forasartan, forfenimex, forfenirmex, formestane, formocortal, formoterol, Fosarilate, Fosazepam, Foscarnet Sodium, fosfomycin, Fosfonet Sodium, fosinopril, Fosinopril sodium, Fosinoprilat, fosphenyloin, Fosquidone, Fostedil, fostriecin, fotemustine, Fuchsin, Fumoxicillin, Fungimycin, Furaprofen, Furazolidone, Furazolium Chloride, Furegrelate Sodium, Furobufen, Furodazole, Furosemide, Fusidate Sodium, Fusidic Acid, Gabapentin, Gadobenate Dimeglumine, gadobenic acid, gadobutrol, Gadodiamide, gadolinium texaphyrin, Gadopentetate Dimeglumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glargine insulin, glaspimod, Glatiramer, glaucocalyxin A, Glemanserin, Gliamilide, Glibornuride, Glicetanile Sodium, Glifiumide, Glimepiride, Glipizide, Gloximonam, Glucagon, glutapyrone, Glutethimide, Glyburide, glycopine, glycopril, Glycopyrrolate, Glymidine Sodium, Glyoctamide, Glyparamide, Gold Au-198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, hatomamicin, hatomarubigin A, hatomarubigin B, hatomarubigin C, hatomarubigin D, Heparin Sodium, hepsulfam, heregulin, Hetacillin, Heterooium Bromide, Hexachlorophene:Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, histrelin acetate, Homatropine Hydrobromide, Hoquizil Hydrochloride, Human chorionic gonadotropin, Human growth hormone, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurea, Hydroxyzine Hydrochloride, Hymecromone, Hyoscyamine, hypericin, Ibafloxacin, Ibandronate, ibogaine, Ibopam, ibudilast, Ibufenac, Ibuprofen, Ibutilide Fumarate, Icatibant Acetate, Ichthammol, Icotidine, idarubicin, idoxifene, Idoxuridine, idramantone, Ifetroban, Ifosfamide, Ilepeimide, illimaquinone, ilmofosin, ilomastat, Ilonidap, iloperidone, iloprost, Imafen Hydrochloride, Imatinib, Imazodan Hydrochloride, imidapril, imidazenil, imidazoacridone, Imidecyl Iodine, Imidocarb Hydrochloride, Imidoline Hydrochloride, Imidurea, Imiglucerase, Imiloxan Hydrochloride, Imipenem, Imipramine Hydrochloride, imiquimod, Impromidine Hydrochloride, Indacrinone, Indapamide, Indecamide Hydrochloride, Indeloxazine Hydrochloride, Indigotindisulfonate Sodium, indinavir, Indinavir sulfate, Indocyanine Green, Indolapril Hydrochloride, Indolidan, indometacin, Indomethacin Sodium, Indoprofen, indoramin, Indorenate Hydrochloride, Indoxole, Indriline Hydrochloride, infliximab, inocoterone, inogatran, inolimomab, Inositol Niacinate, Insulin, Interferon beta-1a, Intrazole, Intriptyline Hydrochloride, iobenguane, Iobenzamic Acid, iobitridol, Iodine, iodoamiloride, iododoxorubicin, iofratol, iomeprol, iopentol, iopromide, iopyrol, iotriside, ioxilan, ipazilide, ipenoxazone, ipidacrine, Ipodate Calcium, ipomeanol, Ipratropium, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladin, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isofluorophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, ixabepilone, jasplakinolide, Jemefloxacin, Jesopitron, Josamycin, kahalalide F, Kalafungin, Kanamycin Sulfate, ketamine, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, Lactobionate, laennec, lafutidine, 1-alphahydroxyvitamin D2, lamellarin-N triacetate, lamifiban, Lamivudine, Lamotrigine, lanoconazole, Lanoxin, lanperisone, lanreotide, lanreotide acetate, Lansoprazole, lapatinib, laropiprant, latanoprost, lateritin, laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, leuprolide, Leuprolide Acetate, leuprorelin, Levalbuterol, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, levocetirizine, levocetirizine dihydrochloride, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizin, Lifibrate, Lifibrol, Linarotene, Lincomycin, Linezolid, Linogliride, Linopirdine, linotroban, linsidomine, lintitript, lintopride, Liothyronine I-125, liothyronine sodium, Liotrix, lirexapride, Lisdexamfetamine Dimesylate, lisinopril, Lispro insulin, lissoclinamide, Lixazinone Sulfate, lobaplatin, Lobenzarit Sodium, Lobucavir, locarmate Meglumine, locarmic Acid, locetamic Acid, lodamide, Lodelaben, lodipamide Meglumine, lodixanol, Iodoantipyrine I-131, Iodocholesterol I-131, Iodohippurate Sodium I-131, Iodopyracet I-125, Iodoquinol, Iodoxamate Meglumine, lodoxamide, Iodoxamie Acid, Lofemizole Hydrochloride, Lofentanil Oxalate, Lofepramine Hydrochloride, lofetamine Hydrochloride I-123, Lofexidine Hydrochloride, loglicic Acid, loglucol, loglucomide, loglycamic Acid, logulamide, lohexyl, lombricine, Lomefloxacin, lomerizine, lomethin I-125, Lometraline Hydrochloride, lometrexol, Lomofungin, Lomoxicam, Lomustine, Lonapalene, lonazolac, lonidamine, lopamidol, lopanoic Acid, Loperamide Hydrochloride, lophendylate, Lopinavir, loprocemic Acid, lopronic Acid, lopydol, lopydone, loracarbef, Lorajmine Hydrochloride, loratadine, Lorazepam, Lorbamate, Lorcamide Hydrochloride, Loreclezole, Loreinadol, lorglumide, Lormetazepam, Lornoxicam, lornoxicam, Lortalamine, Lorzafone, losartan, Losartan potassium, losefamic Acid, loseric Acid, losigamone, losoxantrone, losulamide Meglumine, Losulazine Hydrochloride, losumetic Acid, lotasul, loteprednol, lotetric Acid, lothalamate Sodium, lothalamic Acid, lotrolan, lotroxic Acid, lovastatin, loversol, loviride, loxagiate Sodium, loxaglate Meglumine, loxaglic Acid, Loxapine, Loxoribine, loxotrizoic Acid, lubeluzole, Lucanthone Hydrochloride, Lufironil, Lurosetron Mesylate, lurtotecan, lutetium, Lutrelin Acetate, luzindole, Lyapolate Sodium, Lycetamine, lydicamycin, Lydimycin, Lynestrenol, Lypressin, Lysine, lysofylline, lysostaphin, Maduramicin, Mafenide, magainin 2 amide, Magnesium Salicylate, Magnesium Sulfate, magnolol, maitansine, Malethamer, mallotoaponin, mallotochromene, Malotilate, malotilate, mangafodipir, manidipine, maniwamycin A, Mannitol, mannostatin A, manumycin E, manumycin F, mapinastine, Maprotiline, maraviroc, marimastat, Marinol, Masoprocol, maspin, massetolide, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, meclizine hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Meloxicam, Melphalan, Memantine, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Merisoprol, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, methadone, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, methoxy polyethylene glycol-epoetin beta, Methoxyflurane, Methsuximide, Methyclothiazide, Methyl Palmoxirate, Methylatropine Nitrate, Methylbenzethonium Chloride, Methyldopa, Methyldopate Hydrochloride, Methylene Blue, Methylergonovine Maleate, methylhistamine, methylinosine monophosphate, Methylphenidate, Methylprednisolone, Methyltestosterone, Methynodiol Diacelate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoprolol tartrate, Metouizine, metrifonate, Metrizamide, Metrizoate Sodium, Metronidazole, Meturedepa, Metyrapone, Metyrosine, Mexiletine Hydrochloride, Mexrenoate Potassium, Mezlocillin, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minocycline hydrochloride, Minoxidil, Mioflazine Hydrochloride, miokamycin, mipragoside, mirfentanil, mirimostim, Mirincamycin Hydrochloride, Mirisetron Maleate, Mirtazapine, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecamide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, montelukast, Montelukast Sodium, montirelin, mopidamol, moracizine, Morantel Tartrate, Moricizine, Morniflumate, Morphine, Morrhuate Sodium, mosapramine, mosapride, motilide, Motretinide, Moxalactam Disodium, Moxazocine, Moxifloxacin, moxiraprine, Moxnidazole, moxonidine, Mumps Skin Test Antigen, Muzolimine, mycaperoxide B, Mycophenolate mofetil, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Nalidixate Sodium, Nalidixic Acid, nalmefene, Nalmexone Hydrochloride, naloxone, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxen sodium, Naproxol, napsagatran, Naranol Hydrochloride, Narasin, naratriptan, nartograstim, nasaruplase, natalizumab, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, Neutramycin, Nevirapin Nexeridine Hydrochloride, Niacin, Nibroxane, Nicardipine Hydrochloride, Nicergoline, Niclosamide, Nicorandil, Nicotinamide, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, Nifurtimox, nilotinib, nilotinib hydrochloride monohydrate, nilutamide, Nilvadipine, Nimazone, Nimodipine, niperotidine, niravoline, Niridazole, nisamycin, Nisbuterol Mesylate, nisin, Nisobamate, Nisoldipine, Nisoxetin Nisterime Acetate, Nitarsone, nitazoxanide, nitecapone, Nitrafudam Hydrochloride, Nitralamine Hydrochloride, Nitramisole Hydrochloride, Nitrazepam, Nitrendipine, Nitrocydine, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfurane, Norfloxacin, Norgestimate, Norgestomet, Norgestrel, Nortriptyline Hydrochloride, Noscapine, Novobiocin Nylestriol, Nystatin, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Ofornine, okicenone, Olanzepine, Olmesartan, olmesartan medoxomil, olopatadine, olopatadine hydrochloride, olprinone, olsalazine, Olsalazine Sodium, Olvanil, Omalizumab, Omega-3 acid ethyl esters, omeprazole, onapristone, ondansetron, Ontazolast, Oocyte Opipramol Hydrochloride, oracin, Orconazole Nitrate, Orgotein, Orlislat, Ormaplatin, Ormetoprim, Ornidazole, Orpanoxin, Orphenadrine Citrate, osaterone, Oseltamivir, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenopropionate, Oxolinic Acid, Oxprenolol Hydrochloride, Oxtriphylline, Oxybutynin Chloride, Oxychlorosene, Oxycodone, oxycodone hydrochloride, Oxymetazoline Hydrochloride, oxymetholone, Oxymorphone Hydrochloride, Oxypertine, Oxyphenbutazone, Oxypurinol, Oxytetracycline, Oxytocin, ozagrel, Ozlinone, Paclitaxel, palauamine, Paldimycin, palinavir, Palivizumab, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, paracetamol, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, paroxetine hydrochloride, parthenolide, Partricin, Paulomycin, pazelliptine, Pazinaclone, Pazoxide, pazufloxacin, pefloxacin, pegaspargase, Pegorgotein, Pegylated interferon alfa-2a, Pelanserin Hydrochloride, peldesine, Peliomycipelretin, Pelrinone Hydrochloride, Pemedolac, Pemerid Nitrate, Pemetrexed, pemirolast, Pemoline, Penamecillin, Penbutolol Sulfate, Penciclovir, Penfluridol, Penicillamine, Penicillin G Benzathine, Penicillin G Potassium, Penicillin G Procaine, Penicillin G Sodium, Penicillin V Hydrabamine, Penicillin V Benzathine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfofamide, Perfosfamide, pergolide, Perhexyline Maleate, perillyl alcohol, Perindopril, perindoprilat, Perlapin Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenformin, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanylketoconazole, Phenylbutazone, Phenylephrine Hydrochloride, Phenylpropanolamine Hydrochloride, Phenylpropanolamine Polistirex, Phenyramidol Hydrochloride, Phenyloin, Phenyloin sodium, Physostigmine, picenadol, picibanil, Picotrin Diolamine, picroliv, picumeterol, pidotimod, Pifarnine, Pilocarpine, pilsicamide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin, Piperacillin Sodium, Piperamide Maleate, piperazinc, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretanide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Pivampicillin Hydrochloride, Pivopril, Pizotyline, placetin A, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramipexole, Pramiracetam Hydrochloride, Pramoxine Hydrochloride, Pranolium Chloride, Pravadoline Maleate, Pravastatin, Pravastatin sodium, Prazepam, Prazosin, Prazosin Hydrochloride, Prednazate, Prednicarbate, Prednimustine, Prednisolone, prednisolone quetiapine fumerate, Prednisone, Prednival, Pregabalin, Pregnenolone Succiniate, Prenalterol Hydrochloride, Prenylamine, Pridefine Hydrochloride, Prifelone, Prilocalne Hydrochloride, Prilosec, Primaquine Phosphate, Primidolol, Primidone, Prinivil, Prinomide Tromethamine, Prinoxodan, pritosufloxacin, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin (human), Proline, Prolintane Hydrochloride, Promazine Hydrochloride, Promethazine, Promethazine hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, propiram, propiram, propiverine, Propofol, Proponolol hydrochloride, Propoxycaine Hydrochloride, Propoxyphene Hydrochloride, Propranolol Hydrochloride, Propulsid, propylbis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, Protriptyline Hydrochloride, Proxazole, Proxazole Citrate, Proxicromil, Proxorphan Tartrate, prulifloxacin, pseudoephedrine, Pseudophedrine hydrochloride, Puromycin, Pyrabrom, Pyrantel Pamoate, Pyrazinamide, Pyrazofurin, pyrazoloacridine, Pyridostigmine Bromide, Pyridoxine hydrochloride, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, PyrroInitrin, Pyrvinium Pamoate, Quadazocine Mesylate, Quazepam, Quazinone, Quazodine, Quazolast, quetiapine, quetiapine fumarate, quiflapon, quinagolide, Quinaldine Blue, quinapril, Quinapril hydrochloride, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole, Rabeprazole Sodium, Racephenicol, Racepinephrine, Rafoxanide, Ralitoline, raloxifene, raltegravir, raltitrexed, ramatroban, Ramipril, Ramoplanin, ramosetron, ranelic acid, Ranimycin, Ranitidine, Ranitidine hydrochloride, ranolazine, Rauwolfia Serpentina, recainam, Recainam Hydrochloride, Reclazepam, Recombinant factor VIII, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retapamulin, retelliptine demethylated, reticulon, reviparin sodium, revizinone, rhenium etidronate, rhizoxin, R1 retinamide, Ribaminol, Ribavirin, Riboprine, ricasetron, Ridogrel, Rifabutin, Rifametane, Rifamexil, Rifamide, Rifampin, Rifapentine, Rifaximin, rilopirox, Riluzole, rimantadine, Rimcazole Hydrochloride, Rimexolone, Rimiterol Hydrobromide, Rimonabant, rimoprogin, riodipine, Rioprostil, Ripazepam, ripisartan, Risedronate, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rituximab, rivastigmine, rivastigmine tartrate, Rizatriptan, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, Ropinirole, Ropitoin Hydrochloride, ropivacaine, Ropizine, roquinimex, Rosaramicin, rosiglitazone, Rosiglitazone maleate, Rosoxacin, Rosuvastatin, Rotavirus vaccine, rotigotine, Rotoxamine, roxaitidine, Roxarsone, roxindole, roxithromycin, rubiginone B1, ruboxyl, rufloxacin, rupatidine, Rutamycin, ruzadolane, Sabeluzole, safingol, safironil, saintopin, salbutamol, Salbutamol sulfate, Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, sapropterin dihydrochloride, saquinavir, Sarafloxacin Hydrochloride, Saralasin Acetate, sarcophytol A, sargramostim, Sarmoxicillin, Sarpicillin, sarpogrelate, saruplase, saterinone, satigrel, satumomab pendetide, Scopafungin, Scopolamine Hydrobromide, Scrazaipine Hydrochloride, Secalciferol, Secobarbital, Seelzone, segiline, Seglitide Acetate, Selegiline Hydrochloride, Selenium Sulfide, Selenomethionine Se-75, Selfotel, sematilide, semduramicin, semotiadil, semustine, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, sertraline hydrochloride, S-ethynyluracil, setiptiline, Setoperone, Sevelamer, sevirumab, sevoflurane, sezolamide, Sibopirdine, Sibutramine Hydrochloride, Silandrone, Sildenafil, sildenafil citrate, silipide, silteplase, Silver Nitrate, simendan, Simtrazene, Simvastatin, Sincalide, Sinefungin, sinitrodil, sinnabidol, sipatrigine, sirolimus, Sisomicin, Sitagliptin, Sitogluside, sizofiran, sobuzoxane, Sodium Amylosulfate, Sodium Iodide I-123, Sodium Nitroprusside, Sodium Oxybate, sodium phenylacetate, Sodium Salicylate, Sodium valproate, Solifenacin, solverol, Solypertine Tartrate, Somalapor, Somantadine Hydrochloride, somatomedin B, somatomedin C, Somatostatin, somatrem, somatropin, Somenopor, Somidobove, Sorbinil, Sorivudine, sotalol, Soterenol Hydrochloride, Sparfloxacin, Sparfosate Sodium, sparfosic acid, Sparsomy, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, Strontium Chloride Sr-89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomethoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Sumatriptan succinate, Suncillin Sodium, Suproclone, Suprofen, suradista, suramin, Surfomer, Suricamide Maleate, Suritozole, Suronacrine Maleate, Suxemerid Sulfate, swainsonine, symakalim, Symclosene, Symetine Hydrochloride, Taciamine Hydrochloride, Tacrine Hydrochloride, Tacrolimus, Tadalafil, Talampicillin Hydrochloride, Taleranol, Talisomycin, tallimustine, Talmetacin, Talniflumate, Talopram Hydrochloride, Talosalate, Tametraline Hydrochloride, Tamoxifen, tamoxifen citrate, Tampramine Fumarate, Tamsulosin, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Teclozan, Tecogalan Sodium, Teecleukin, Teflurane, Tegafur, Tegaserod, Tegretol, Teicoplanin, telenzepine, tellurapyrylium, telmesteine, telmisartan, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, temsirolimus, Tenidap, Teniposide, Tenofovir, tenosal, tenoxicam, tepirindole, Tepoxalin, Teprotide, terazosin, Terazosin Hydrochloride, Terbinafine, Terbutaline Sulfate, Terconazole, terfenadine, terfiavoxate, terguride, Teriparatide, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetracycline hydrochloride, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thiithixene, Thimerfonate Sodium, Thimerosal, thiocoraline, thiofedrine, Thioguanine, thiomarinol, Thiopental Sodium, thioperamide, Thioridazine, Thiotepa, Thiphenamil Hydrochloride, Thiphencillin Potassium, Thiram, Thozalinone, Threonine, Thrombin, thrombopoietin, thymalfasin, thymopentin, thymotrinan, Thyromedan Hydrochloride, Thyroxine, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, Timolol meleate, Tinabinol, Timidazole, Tinzaparin Sodium, Tioconazole, Tiodazosin, Tiodonium Chloride, Tioperidone Hydrochloride, Tiopinac, Tiospirone Hydrochloride, Tiotidine, Tiotropium, tiotropium bromide, Tioxidazole, Tipentosin Hydrochloride, tipranavir, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tnmethobenzamide Hydrochloride, Tobramycin, Tocamide, Tocamphyl, Tofenacin Hydrochloride, Tolamolol, Tolazamide, Tolazoline Hydrochloride, Tolbutamide, Tolcapone, Tolciclate, Tolfamide, Tolgabide, Tolimidone, Tolindate, Tolmetin, Tolnaftate, Tolpovidone, Tolpyrramide, Tolrestat, Tolterodine, tolterodine tartrate, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor (TSCF), Tracazolate, trafermin, Tralonide, Tramadol, Tramadol Hydrochloride, Tramazoline Hydrochloride, trandolapril, Tranexamic Acid, Tranilast, Transcamide, trastuzumab, traxanox, Trazodone Hydrochloride, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethoprim, Trimetozine, Trimetrexate, Trimipramine, Trimoprostil, Trimoxamine Hydrochloride, Triolein, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine, tropisetron, trospectomycin, trovafloxacin, trovirdine, Tryptophan, Tuberculin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valacyclovir hydrochloride, Valine, Valnoctamide, Valproate semisodium, Valproic Acid, valsartan, vamicamide, vanadeine, Vancomycin, vaminolol, Vapiprost Hydrochloride, Vapreotide, Vardenafil, Varenicline, variolin B, Vasopressin, Vecuronium Bromide, velaresol, Velnacrine Maleate, venlafaxine, Venlafaxine hydrochloride, Veradoline Hydrochloride, veramine, Verapamil Hydrochloride, verdins, Verilop am Hydrochloride, Verlukast, Verofylline, veroxan, verteporfin, Vesnarinone, vexibinol, Vidarabine, vigabatrin, vildagliptin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Voglibose, Volazocine, voriconazole, vorozole, voxergolide, Wafarin, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, xylose, yangambin, zabicipril, zacopride, zafirlukast, Zalcitabine, Zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, Zoledronate, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin, and pharmaceutically acceptable salts thereof.

EXAMPLE 1

The capsule as described herein is used to administer leuprolide acetate for the treatment of prostate cancer. Leuprolide acetate (USP 31) is a synthetic nonapeptide agonist analog of luteinizing hormone-releasing factor (LNHR). The leuprolide acetate molecule is approximately 1209 Daltons in weight and two to three nanometers in size. It is soluble in aqueous media at a level of approximately 10 mg/mL. An existing method of administering leuprolide via extended release is disclosed in U.S. Pat. No. 5,728,396 filed Jan. 30, 1997 and incorporated herein by reference.

The nanochannel delivery device chip is installed in a capsule as described herein and filled with a 5 mg/mL leuprolide acetate solution (NDC number 0703-4014-18) for use in the treatment of prostate cancer. The capsule is sized to approximately 2.8 mL, so that the filled capsule contains approximately 14 mg of leuprolide acetate. If stronger concentrations of leuprolide acetate solution are used, the capsule volume may be correspondingly reduced. The capsule is implanted subcutaneously in the inner portion of the upper arm or upper leg or in the abdomen. The capsule is implanted, with optional use of a tissue separator, through a small incision in a clinical outpatient procedure and removed two to three months later through a small incision. For implant and explant, a small amount of anesthetic is used, for example, a 1% lidocaine injection at the site.

The micro- and nano-channel sizes of the nanochannel delivery device are chosen (for example, according to the model described in [Grattoni, A. Ferrari, M., Liu, X. Quality control method for micro-nano-channels silicon devices. U.S. Patent Application No. 61/049,287 (April 2008)]), to provide a release rate of about 120 μg/day can be obtained for about 90 days in certain embodiments.

In this example, the nanochannel delivery device configuration with this behavior uses a 6×6 mm chip size, with 161 macrochannels with openings of 190×190 μm each, and within each macrochannel approximately 23 rows of nanochannel structures, consisting of 10 each of inlet and outlet microchannels, connected through about 20 nanochannels according to the description herein. The inlets and outlets are approximately 5×5 μm in cross-section, with the inlets being about 30 μm long and the outlets being about 1.6 μm long, and the nanochannels are about 5 μm long and 5 μm wide and 13 nm high. Other configurations with different dimensions may be derived from the mathematical model that yield approximately the same release rate and duration in other examples.

EXAMPLE 2

The capsule and nanochannel delivery device are configured and implanted as described in Example 1. However, instead of administering leuprolide acetate, the capsule and nanochannel delivery device administer letrozole for the treatment of breast cancer. The limited success of chemotherapy for the treatment of breast cancer emphasizes the need of novel preventive strategies to minimize the cancer occurrence. Recent studies have highlighted that aromatase inhibitors are promising chemopreventive agents for breast cancer through inhibition of estrogen biosynthesis. In particular, research has suggested that letrozole is an ideal candidate for chemoprevention for women in high risk group such as BRCA1 positive. However, the low efficacy and the side effects associated with the conventional systemic administration of letrozole are limiting factors for its long term usage.

Breast cancer growth is highly dependent on estrogen, and thus inhibition of estrogen is highly effective for the prevention of breast tumor development. Recent studies have highlighted aromatase inhibitors such as anastrozole, letrozole, and exemestane, as promising molecules that can be used for chemoprevention of breast cancer. Aromatase mediates biosynthesis of estradiol, the most potent form of estrogen, from androgens by the cytochrome P450 enzyme complex (Aromatase). Aromatase is present in breast tissue and the nonsteroidal and steroidal aromatase inhibitors reduce circulating estrogen level to 1% to 10% of pretreatment levels, respectively. Therefore, inhibition of aromatase is an important approach for reducing growth-stimulatory effects of estrogens in estrogen-dependent breast cancer, which constitutes approximately 60-70% of breast cancer. Among the aromatase inhibitors, letrozole is a highly potent non-steroid inhibitor which inhibits approximately 99% of estrogen biosynthesis. Additionally, several studies and clinical trials on chemotherapy of metastatic breast cancer indicated higher efficacy with fewer side effects of letrozole when compared to Tamoxifen. Hence, research suggests letrozole as a candidate for the development of chemopreventive therapy for women at increased risk of breast cancer. However, the conventional oral administration of letrozole showed increased risk of heart problems and osteoporosis. The key for the success of chemoprevention for breast cancer relies on long term delivery of specific drugs while circumventing side effects. As opposed to the inefficient oral administration, a constant local release of chemopreventive agent (i.e. letrozole) in breast tissue could significantly reduce occurrence of breast tumor as well as systemic side effects. This shows promise for improvement in patient quality of life.

It is believed that the implantable nanochanneled devices according to the present disclosure will allow the constant and sustained local release of letrozole in breast tissues and significant reduction of estrogen dependent epithelial cell proliferation with minimum toxicities.

Prior clinical trials employed letrozole daily doses of 2.5 mg. It is believed that the constant local release of letrozole in breast tissues (utilizing nanochanneled devices according to the present disclosure) would require lower dosage if compared to oral delivery. In first analysis it is believed that a local daily release in the range 25 to 50 ug could be effective.

The achievement of an efficient chemopreventive therapy by the use of long-term, constant release implants for local administration of chemopreventive agents will have significant impact on the quality of life of women in the high risk group. It is believed that use of nanochannel delivery devices according to the present disclosure will lead to improved efficacy of therapy, as well as potential reduction of drug doses and reduction of side effects through true constant release. A reduction in the number of breast cancer occurrences due to effective preventive therapy would also have a positive economic impact on patients, their employers and insurers through lowered cost of treatment, fewer medical visits, and less work time lost.

The development of a reliable extended release implantable technology adds a new dimension to drug delivery for breast cancer. Tumor treatment and the suppression of metastasis and/or tumor recurrence are natural follow-on developments. Technology enhancements to the initial platform could support variable and programmed release, including remote, interactive control of the implanted device, further enabling capabilities to deploy multiple drugs simultaneously. In vivo refilling could also extend the functionality of the nanochannel device and also decrease adverse events associated with explanation. As a general drug delivery method, other indications may be identified, broadening the applicability of the innovation.

EXAMPLE 3

The capsule and nanochannel delivery device are configured and implanted in a patient as described in Example 1. However, instead of administering leuprolide acetate, the capsule and nanochannel delivery device administer lapatinib for the treatment of breast cancer.

EXAMPLE 4

The capsule and nanochannel delivery device are configured and implanted in a patient as described in Example 1. However, instead of administering leuprolide acetate, the capsule and nanochannel delivery device administer buprenorphine for the treatment of opiate dependency.

EXAMPLE 5

The capsule and nanochannel delivery device are configured and implanted in a patient as described in Example 1. However, instead of administering leuprolide acetate, the capsule and nanochannel delivery device administer interferon alpha implant for giant cell angioblastoma.

EXAMPLE 6

The capsule and nanochannel delivery device are configured and implanted in a patient as described in Example 1. However, instead of administering leuprolide acetate, the capsule and nanochannel delivery device administer zidovudine in an intravaginal treatment for preventing HIV being transmitted from a pregnant mother to a child.

As used herein, the term "direct fluid communication" is interpreted as fluid communication between two bodies that are directly connected, e.g. such that fluid may exit one body and immediately enter the second body without flowing through an intermediate body. For example, in the embodiment shown in FIGS. 3A-3G, outlet 70 is in direct fluid communication with nanochannel 25. However, outlet 70 is not in direct fluid communication with inlet 30, because fluid must flow through an intermediate body (nanochannel 25) after exiting inlet 30 and before entering outlet 70.

Furthermore, as used herein, the term "inlet" is interpreted as a chamber or reservoir within a nanochannel delivery device that initially retains a substance being delivered via the nanochannel delivery device. Similarly, an "outlet" is interpreted as a chamber or reservoir within a nanochannel delivery device that retains a substance immediately prior to the substance exiting the nanochannel delivery device.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

[1] Santen, R. J., Yue, W., Naftolin, F., Mor, G., Berstein, L. The potential of aromatase inhibitors in breast cancer prevention. *Endocrine-Related Cancer.* 6, 235-243 (1999).

[2] Goss, P. E., Strasser, K. Aromatase Inhibitors in the Treatment and Prevention of Breast Cancer. *J. Clin. Oncol.* 19, 881-894 (2001).

[3] Chlebowski, R. T. Reducing the Risk of Breast Cancer. *N. Engl. J. Med.,* 343, 191-198 (2000).

[4] Dowsett, M., Jones, A., Johnston, S. R., Jacobs, S., Trunet, P., Smith, I. E. In vivo measurement of aromatase inhibition by letrozole (CGS 20267) in postmenopausal patients with breast cancer. *Clin. Cancer Res.* 1, 1511-1515 (1995).

[5] Brueggemeier, R. W., Hackett, J. C., Diaz-Cruz, E. S. Aromatase Inhibitors in the Treatment of Breast Cancer. *Endocrine Reviews* 26, 331-345 (2005).

[6] Coates, A. S., Keshaviah, A., Thürlimann, B., et al. Five years of letrozole compared with tamoxifen as initial adjuvant therapy for postmenopausal women with endocrine-responsive early breast cancer: update of study BIG 1-98. *J. Clin. Oncol.* 25, 486-492 (2007).

[7] Goss, P. E., Ingle, J. N., Martino, S., et al. A randomized trial of letrozole in postmenopausal women after five years of tamoxifen therapy for early-stage breast cancer. *N. Engl. J. Med.* 349, 1793-1802 (2003).

[8] Garreau, J. R., Delamelena, T., Walts, D., Karamlou, K., Johnson, N. Side effects of aromatase inhibitors versus tamoxifen: the patients' perspective. *Am. J. Surg.* 192, 496-8 (2006).

[9] Luthra, R., Kirma, N., Jones, J., Tekmal, R. R. Use of letrozole as a chemopreventive agent in aromatase overexpressing transgenic mice. *The Journal of Steroid Biochemistry and Molecular Biology.* 86, 461-467 (2003).

[10] Harper-Wynne, C., Ross, G., Sacks, N., Salter, J., Nasiri, N., Iqbal, J., A'Hern, R., Dowsett, M. Effects of the aromatase inhibitor letrozole on normal breast epithelial cell proliferation and metabolic indices in postmenopausal women: a pilot study for breast cancer prevention. *Cancer Epidemiol. Biomarkers Prev.* 11, 614-21 (2002).

The invention claimed is:

1. A method of fabricating a nanochannel delivery device, the method comprising:
   providing first substrate;
   forming a plurality of nanochannels on the first substrate;
   filling in the plurality of nanochannels with a first sacrificial material;
   forming a plurality of inlet microchannels in the first substrate;
   filling in the plurality of inlet microchannels with a second sacrificial material;
   forming a capping layer that covers the plurality of nanochannels;

forming a plurality of outlet microchannels in the capping layer;

removing the first sacrificial material from the plurality of nanochannels; and removing the second sacrificial material from the plurality of inlet microchannels.

2. The method of claim 1, wherein an inlet microchannel of the plurality of inlet microchannels is arranged perpendicular to a primary plane of the first substrate.

3. The method of claim 1, wherein an outlet microchannel of the plurality of outlet microchannels is arranged perpendicular to a primary plane of the first substrate.

4. The method of claim 1, wherein an inlet microchannel of the plurality of inlet microchannels is in direct fluid communication with a nanochannel.

5. The method of claim 1, wherein an outlet microchannel of the plurality of outlet microchannels is in direct fluid communication with a nanochannel.

6. The method of claim 1, wherein the inlet and outlet microchannels are patterned using a photolithography process.

7. The method of claim 1, wherein each nanochannel is between approximately one and ten nanometers deep.

8. The method of claim 1, wherein each nanochannel is between approximately ten and twenty nanometers deep.

9. The method of claim 1, wherein the first sacrificial material is subsequently removed by selective etching.

10. The method of claim 1, wherein the first sacrificial material is tungsten.

11. The method of claim 1, wherein the second sacrificial material is filled into the plurality of inlet microchannels so that the second sacrificial material extends above the top of the plurality of inlet microchannels and is planarized by chemical-mechanical planarization (CMP).

12. The method of claim 1 wherein the capping layer is selected from silicon nitride, silicon oxide, silicon carbonitride, silicon carbide, and silicon.

13. The method of claim 1, wherein the capping layer comprises multiple depositions of materials comprising tensile and compressive stresses such that the net capping layer stress is tensile.

14. The method of claim 1, wherein the capping layer is between approximately 0.5 and 1.0 microns thick.

15. The method of claim 1, wherein the capping layer is between approximately 1.0 and 2.0 microns thick.

16. The method of claim 1, wherein the capping layer is between approximately 2.0 and 4.0 microns thick.

17. The method of claim 1, wherein the second sacrificial material is subsequently removed by selective etching.

18. The method of claim 17, wherein the second sacrificial material is selected from the group consisting of: tungsten, copper, doped glass, and undoped glass.

19. The method of claim 1, wherein the first substrate comprises a silicon-on-insulator wafer comprising an internal oxide layer.

20. The method of claim 19, wherein forming the plurality of inlet microchannels comprises etching material from the first substrate, and wherein the etching is terminated at the internal oxide layer.

21. The method of claim 20, wherein forming a plurality of inlet macrochannels comprises etching material from a back side of the first substrate, and wherein the etching is terminated at the internal oxide layer.

22. The method of claim 21, further comprising removing of the internal oxide layer after etching material to form the inlet microchannel and inlet macrochannels to open a pathway between the inlet microchannels and inlet macrochannels.

* * * * *